(12) United States Patent
Foody et al.

(10) Patent No.: US 10,487,282 B2
(45) Date of Patent: *Nov. 26, 2019

(54) METHOD AND SYSTEM FOR PROVIDING UPGRADED BIOGAS

(71) Applicant: Iogen Corporation, Ottawa (CA)

(72) Inventors: Brian Foody, Ottawa (CA); Patrick J. Foody, Ottawa (CA)

(73) Assignee: Iogen Corporation, Ottawa (CA)

( * ) Notice: Subject to any disclaimer, the term of this patent is extended or adjusted under 35 U.S.C. 154(b) by 0 days.

This patent is subject to a terminal disclaimer.

(21) Appl. No.: 15/970,591

(22) Filed: May 3, 2018

(65) Prior Publication Data
US 2018/0251694 A1    Sep. 6, 2018

Related U.S. Application Data

(63) Continuation of application No. 15/458,760, filed on Mar. 14, 2017, now Pat. No. 9,969,949.

(Continued)

(51) Int. Cl.
*B01D 53/047* (2006.01)
*B01D 53/22* (2006.01)
(Continued)

(52) U.S. Cl.
CPC ............ *C10L 3/104* (2013.01); *B01D 53/047* (2013.01); *B01D 53/22* (2013.01); *B01D 53/261* (2013.01);
(Continued)

(58) Field of Classification Search
CPC ................................................ C10L 3/104
See application file for complete search history.

(56) References Cited

U.S. PATENT DOCUMENTS

| 6,789,288 B2 | 9/2004 | Wijmans et al. |
| 8,158,378 B2 | 4/2012 | Mitariten |
| (Continued) | | |

FOREIGN PATENT DOCUMENTS

| EP | 2974781 | 1/2016 |
| WO | WO 2011150899 | 12/2011 |

OTHER PUBLICATIONS

Air Liquide, "MEDAL™ membrane systems for Biogas/Landfill gas" [Brochure], www.medal.airliquide.com/en/biogaz-systems.html, Access date Sep. 12, 2016.

(Continued)

*Primary Examiner* — Philip Y Louie
(74) *Attorney, Agent, or Firm* — Knobbe Martens Olson & Bear LLP

(57) ABSTRACT

A method for providing upgraded biogas includes feeding a stream of biogas into a biogas upgrading system in order to remove carbon dioxide from the stream of biogas. The biogas upgrading system, which may be based on absorption, adsorption, membrane permeation, and/or cryogenics, provides a stream of upgraded biogas and a tail gas stream. The tail gas stream, which may be $CO_2$-rich, is enriched with natural gas so that it is combustible in medium-BTU equipment. The upgraded biogas is used for transportation use and/or the generation of fuel credits. Accordingly, both the tail gas and the upgraded biogas are used effectively and at lower cost.

20 Claims, 25 Drawing Sheets

Related U.S. Application Data

(60) Provisional application No. 62/410,730, filed on Oct. 20, 2016.

(51) Int. Cl.

| | | |
|---|---|---|
| *C10L 3/10* | (2006.01) | |
| *B01D 53/26* | (2006.01) | |
| *C02F 11/04* | (2006.01) | |
| *G06Q 30/02* | (2012.01) | |
| *G06Q 50/06* | (2012.01) | |
| *C02F 103/28* | (2006.01) | |
| *C02F 103/32* | (2006.01) | |
| *B01D 53/14* | (2006.01) | |

(52) U.S. Cl.
CPC ......... *B01D 53/263* (2013.01); *B01D 53/265* (2013.01); *B01D 53/266* (2013.01); *C02F 11/04* (2013.01); *C10L 3/101* (2013.01); *C10L 3/105* (2013.01); *G06Q 30/0227* (2013.01); *G06Q 50/06* (2013.01); *B01D 53/1475* (2013.01); *B01D 53/229* (2013.01); *B01D 2252/103* (2013.01); *B01D 2253/102* (2013.01); *B01D 2253/106* (2013.01); *B01D 2253/108* (2013.01); *B01D 2253/1124* (2013.01); *B01D 2256/245* (2013.01); *B01D 2257/102* (2013.01); *B01D 2257/304* (2013.01); *B01D 2257/504* (2013.01); *B01D 2257/553* (2013.01); *B01D 2257/556* (2013.01); *B01D 2257/80* (2013.01); *B01D 2258/05* (2013.01); *C02F 2103/28* (2013.01); *C02F 2103/32* (2013.01); *C10L 2290/02* (2013.01); *C10L 2290/24* (2013.01); *C10L 2290/542* (2013.01); *C10L 2290/548* (2013.01); *Y02C 10/04* (2013.01); *Y02C 10/08* (2013.01); *Y02C 10/10* (2013.01); *Y02E 50/343* (2013.01); *Y02W 10/37* (2015.05)

(56) References Cited

U.S. PATENT DOCUMENTS

| | | | |
|---|---|---|---|
| 8,177,885 B2 | 5/2012 | Wijmans et al. | |
| 8,999,036 B2 | 4/2015 | Pierce | |
| 2009/0318743 A1* | 12/2009 | Arnold | C01B 3/382 585/658 |
| 2011/0023497 A1 | 2/2011 | Assmann | |
| 2011/0189746 A1* | 8/2011 | Mitariten | C12P 5/02 435/167 |
| 2011/0229405 A1* | 9/2011 | Guo | C01B 3/323 423/648.1 |
| 2012/0290221 A1 | 11/2012 | Arjona Antolin et al. | |
| 2013/0019633 A1 | 1/2013 | Pierce | |
| 2013/0087339 A1* | 4/2013 | Foody | E21B 43/16 166/305.1 |
| 2013/0109767 A1* | 5/2013 | Bogild | C10L 3/08 518/702 |
| 2013/0209338 A1 | 8/2013 | Prasad et al. | |
| 2013/0225885 A1* | 8/2013 | Foody | C07C 5/02 585/254 |
| 2014/0020402 A1* | 1/2014 | Okamura | F01D 25/12 60/784 |
| 2014/0043932 A1 | 2/2014 | Russell et al. | |
| 2014/0222698 A1* | 8/2014 | Potdar | G06Q 30/018 705/317 |
| 2014/0357737 A1* | 12/2014 | Abbott | C10K 1/005 518/704 |
| 2016/0090910 A1 | 3/2016 | Ploeger et al. | |
| 2017/0056839 A1* | 3/2017 | Ho | B01D 69/142 |

OTHER PUBLICATIONS

Anderson, "Landfill Gas Upgrading to Pipeline Quality in the U.S.," World Congress of Bioenergy, Dalian, China (Apr. 28, 2011).

Anderson et al., "Simplified Biogaz System," 26th Annual Landfill Gas Symposium, Tampa, Florida (Mar. 24-27, 2003), 1-8.

Baker, "Future Directions of Membrane Gas Separation Technology," Ind. Eng. Chem. Res., vol. 41, No. 6 (2002) 1393-1411.

Bauer et al., "Biogas upgrading—Review of commercial technologies," SGC Rapport vol. 270 (2013) 1-83.

California Air Resources Board, "Low Carbon Fuel Standard (LCFS) Pathway for the Production of Biomethane from the Mesophilic Anaerobic Digestion of Wastewater Sludge at a Publicly-Owned Treatment Works (POTW)," (Dec. 15, 2014).

Cohn et al., "WCA & Fort Bend Power Producers: Generating High BTU Gas from Landfill Gas in Texas," dated Jul. 16, 2013 (Retrieved from https://www.epa.gov/sites/production/files/2016-05/documents/10ftbend.pdf, Dec. 9 2016).

Deng et al., "Techno-economic evaluation of biogas upgrading process using CO2 facilitated transport membrane," International Journal of Greenhouse Gas Control 4 (2010) 638-646.

"Expander-compressors, an introduction," Turbomachinery International (2016), pp. 1-3.

Grande, "Biogas Upgrading by Pressure Swing Adsorption," Chapter from the book 'Biofuel's Engineering Process Technology,' (Aug. 1, 2011) 65-84.

Haider et al., "Techno-economical evaluation of membrane based biogas upgrading system; a comparison between polymeric membrane and carbon membrane technology," Green Energy & Environment (2016), 1-13, http://dx.doi.org/10.1016/j.gee.2016.10.003.

Makaruk et al., "Membrane biogas upgrading processes for the production of natural gas substitute," Separation and Purification Technology 74 (2010) 83-92.

Persson, "Biogas up-grading: a technical review," IEA Bioenergy Task 37, dated Nov. 14, 2013 (Retrieved on Dec. 9, 2016 from https://www.iea-biogas.net/files/daten-redaktion/download/publications/Workshops/2013_Korea/7_Persson_Biogas_Up-grading_Technical_Review_Task_37_Biogas_Workshop_Seoul_11-2013.pdf).

Petersson et al., "Biogas upgrading technologies—developments and innovations," IEA Bioenergy Task 37, dated Oct. 2009 (Retrieved on Dec. 9, 2016 from https://www.iea-biogas.net/files/daten-redaktion/download/publi-task37/upgrading_rz_low_final.pdf).

Schill, S.R., "The 2014 D3 RIN Leap-For Biogas," Ethanol Producer Magazine (2015), pp. 1-4.

Scholz, "Membrane Based Biogas Upgrading Processes," Ph.D Dissertation, RWTH Aachen University, 2013.

Smyth et al., "Quantification of the Incremental Cost of Nitrogen and Oxygen Removal at High-Btu Plants," 14th Annual EPA LMOP Conference and Project Expo, Baltimore, Maryland (Jan. 18-20, 2011) (Retrieved on Dec. 9, 2016 from https://www.epa.gov/sites/production/files/2016-06/documents/smyth.pdf).

Vienna University of Technology, "Biogas to Biomethane Technology Review," (Retrieved on Dec. 9, 2016 from http://www.aile.asso.fr/wp-content/uploads/2012/06/wp3-1-1_technologyreview_english.pdf).

Vienna University of Technology, "Overview of Lean Gas Treatment in Biogas Upgrading Systems," (Retrieved on Dec. 9, 2016 from http://www.fvmmi.hu/file/document/hir/leangas.pdf).

Xebec, "BGXSolutions, Biogas Upgrading Plants," [Brochure], (Retrieved on Dec. 9, 2016 from www.xebecinc.com).

Zhao et al., "Purification Technologies for Biogas Generated by Anaerobic Digestion," CSANR Research Report. 2010-001.

International Search Report and Written Opinion dated Jan. 18, 2018 for PCT Application No. PCT/CA2017/051241 filed Oct. 19, 2017.

\* cited by examiner

METHOD AND SYSTEM FOR PROVIDING UPGRADED BIOGAS

INCORPORATION BY REFERENCE TO ANY PRIORITY APPLICATIONS

Any and all applications for which a foreign or domestic priority claim is identified, for example, in the Application Data Sheet or Request as filed with the present application, are hereby incorporated by reference under 37 CFR 1.57, and Rules 4.18 and 20.6.

TECHNICAL FIELD

The present disclosure relates to a method and system for providing upgraded biogas, and in particular, relates to a method and system for upgrading biogas that may be injected into a distribution system.

BACKGROUND

Biogas, which is a mixture of several gases, may be produced by the breakdown of organic matter in low oxygen conditions. In particular, it may be produced by the anaerobic digestion or fermentation of organic matter (e.g., manure, sewage sludge, municipal solid waste, biodegradable waste, biodegradable feedstock, etc.).

The composition of biogas, which varies with the type of organic matter (e.g., biomass) from which it is derived, is predominately methane ($CH_4$) and carbon dioxide ($CO_2$), with relatively small amounts of hydrogen sulfide ($H_2S$), ammonia ($NH_3$), hydrogen ($H_2$), nitrogen ($N_2$), carbon monoxide (CO), oxygen ($O_2$), water vapour, and/or siloxanes. For example, the composition of biogas may include about 60% $CH_4$ (e.g., between about 45% and about 70%) and about 35% $CO_2$ (e.g., between about 25% and about 55%).

Biogas is considered a renewable fuel. In its raw form, biogas may be combusted (e.g., in an engine, turbine, or boiler) in order to generate heat (e.g., steam) and/or electricity. For example, biogas has been used in combined heat and power (CHP) plants in order to generate electricity and heat. Optionally, raw biogas is cleaned to remove $H_2S$ and/or water vapour prior to combustion in order to reduce equipment corrosion.

In general, the methane content of raw biogas and/or cleaned biogas is low (e.g., about 40% to about 60%) relative to that of fossil natural gas (e.g., greater than about 96%). While biogas CHP plants are often designed and/or configured to combust this lower quality gas, the quality of biogas (e.g., heating value) is generally too low for various other applications (e.g., direct injection into a distribution system carrying natural gas and/or for use as a transportation fuel). In addition to reducing the heating value of biogas, the large amount of $CO_2$ in biogas may increase compression costs and/or increase transportation costs. For example, with regard to the latter, since biogas does not typically meet natural gas pipeline standards a separate dedicated biogas pipeline or pipeline system may be required to transport biogas to end users (e.g., where a natural gas pipeline cannot be used).

Accordingly, biogas use traditionally has been limited to near the point of production. In fact, one important biogas application is the cogeneration of heat and electricity for use in the plant and/or process that produces the biogas (e.g., a waste treatment plant and/or cellulosic ethanol plant that require heating the digester, space heating, water heating, and/or process heating). For example, cogeneration may reduce the amount of electricity and/or heating fuel imported into the plant/process, thereby reducing costs. In addition, it may enhance power reliability for the process and/or provide the opportunity to reduce greenhouse gas (GHG) emissions (e.g., since a renewable fuel may replace an imported fossil fuel).

In order to use biogas as a transportation fuel, or for unlimited injection into a distribution system, where it may be used to produce electricity, used for residential heating, or used as a transportation fuel, biogas may be upgraded (e.g., to renewable natural gas (RNG)). The terms "renewable natural gas" and "RNG", as used herein, refers to biogas that has been upgraded to a quality similar to fossil natural gas. For example, RNG may refer to biogas that has been upgraded to natural gas pipeline quality (e.g. >95% $CH_4$) and thus is substantially interchangeable with natural gas. Pipeline standards or specifications may vary by region. For example, Canadian pipelines standards may require a $H_2S$ content that does not exceed 6 mg/m$^3$, a $CO_2$ level that is less than about 2%, and/or a $CH_4$ level that is greater than 95%. In addition, or alternatively, the natural gas pipeline standards may refer to the purity of the gas expressed as a heating value (e.g., in British Thermal Units (BTU)/cubic foot). In general, the higher the heating value, the cleaner the gas (e.g., fewer and/or lower amounts of impurities). Pipeline standards may require, for example, that the heating value of RNG be greater than about 950 BTU/cubic foot, greater than about 960 BTU/cubic foot, or greater than about 967 BTU/cubic foot. In one embodiment, the pipeline standards are dictated by the Federal Energy Regulatory Commission (FERC). In one embodiment, the pipeline standards are defined by the standards developed and adopted by the Wholesale Gas Quadrant (WGQ) of the North American Energy Standards Board (NAESB). Optionally, propane or another fuel is added to the upgraded biogas to improve the heating value and/or meet pipeline standards. Optionally, the upgraded biogas is mixed with fossil natural gas prior to injection in order to provide the required heating value and/or meet pipeline standards.

Upgraded biogas (e.g., RNG) may be injected and distributed through a distribution system (DS) after it has been compressed to the local pipeline pressure. The terms "distribution system" and "DS", as used herein with reference to natural gas, refers to a pipeline and/or pipeline system that carries natural gas and serves an end user (e.g., consumer). The term "pipeline system", as used herein, refers to an interconnected network of pipes (e.g., physically connected). For example, a distribution system for natural gas may include large transmission pipelines and smaller distribution pipelines, as well as the connections to them, including, for example, auxiliary equipment such as control and metering equipment. Transmission pipelines are medium to high-pressure pipelines used for transporting natural gas to one or more distribution companies (e.g. including across provincial, state, or country borders). In order to propagate the natural gas along transmission pipelines, the natural gas may be compressed periodically at compressor stations. Distribution pipelines are relatively low-pressure pipelines typically used to distribute natural gas sourced from the transmission pipeline to the consumers. Natural gas storage facilities may be provided in a pipeline system for instances when the natural gas being transported is not immediately required. One example of a distribution system (DS) is the US natural gas grid (i.e., highly integrated network of transmission and distribution pipelines that can receive natural gas and/or biogas and serve millions of locations).

Advantageously, injecting upgraded biogas (e.g., RNG) into a distribution system (DS) takes full advantage of the existing pipelines and/or pipeline system(s) and existing demand. In addition, it enables the biogas to reach new customers. Further advantageously, injecting upgraded biogas into a DS may also displace fossil fuels used for transportation. For example, RNG used for transportation could displace on-road diesel fuel. Since the basis of commerce in distribution systems is displacement (e.g., matching injections into the DSs with withdrawals out of the DS without tracking specific molecules), and since RNG is essentially interchangeable with fossil natural gas (e.g., is fungible), a renewable transportation fuel may be withdrawn far from the point of injection of the RNG. Unfortunately, the purification processes used for upgrading biogas (e.g., to RNG) are relatively expensive. In addition, the capital investment may be high.

Although the cost of upgrading a given volume of biogas (e.g., to RNG) may be lower for larger systems, the diversion of all of the biogas produced by a process to an upgrading system may result in additional electricity and/or natural gas having to be imported into the process. For example, if the energy costs and/or GHG emissions of the process could be reduced by using some heat and/or electricity provided by a biogas CHP located at or near the biogas producing plant/process, the diversion of the biogas used in the CHP to a biogas upgrading system that produces RNG for injection into the DS and/or for transportation use would result in the process having to import additional natural gas, thus further increasing costs.

In addition, additional cost and/or complexity may arise from the nature of the DS and/or the location of the RNG injection point (e.g., which may be in a rural or low demand area far from high demand industrial areas). For example, in a DS, the natural gas fed from transmission pipelines will generally find its way to the customers through a network of pipes from high pressures and large diameters down to low pressures and smaller diameters. Although the flow of the gas is driven largely by the demand of the customers, if a large influx of RNG is introduced into the system, the pressure and/or flows may change. Accordingly, the existing DS may have to be modified to make it possible to distribute the RNG to a sufficient number of customers. This modification takes time and money.

It would be advantageous to reduce the cost of upgrading biogas and injecting the upgraded biogas into a DS and/or to incentivize the utilization of RNG as a transportation fuel.

SUMMARY

The present disclosure describes one or more embodiments of a method and/or system wherein biogas is upgraded, thereby providing upgraded biogas and tail gas. Advantageously, tail gas from the biogas upgrading, which may contain carbon dioxide ($CO_2$) and/or $N_2$ removed from the biogas during upgrading, is enriched with natural gas. In one embodiment, sufficient natural gas is added to allow the natural gas-enriched tail gas to be combusted for heat and/or power generation. While it may seem counterintuitive to feed relatively inexpensive biogas into a biogas upgrading unit that separates the $CO_2$ from the plant-based methane ($CH_4$), and to then enrich tail gas containing at least some of the removed components with relatively expensive natural gas, it has been found that doing so may reduce the cost of and/or improve the economics of upgrading the biogas and/or injecting the upgraded biogas into the distribution system (DS). For example, costs may be reduced and/or economics improved by the production of more renewable natural gas (RNG), by providing access to higher value markets, and/or by enriching the tail gas with natural gas withdrawn from the DS such that the natural gas facilitates and/or improves the efficiency of the biogas upgrading. The enriched tail gas may be combusted, thereby producing heat and/or electricity for use in the plant/process and/or obviating the stranding of biogas combustion equipment. The cost effectiveness may be further improved by using electricity generated from the enriched tail gas and/or energy captured from a pressure letdown resulting from withdrawing natural gas for enriching the tail gas to compress the upgraded biogas for injection into the DS.

Advantageously, improving the economics of upgrading and/or injecting the upgraded biogas into a DS provides incentive to produce RNG, and in particular, provides incentive to produce it for transportation use. While injecting upgraded biogas into a DS may be generally advantageous in terms of providing a renewable fuel and displacing fossil methane, it is particularly advantageous to inject upgraded biogas into a DS for transportation use. For example, it has the potential to reduce emissions with regard to transport (e.g., decarbonize the transportation sector), provide diversity to the transportation sector, and/or allows participation in incentive programs (e.g., fuel credits such as RINs or LCFS credits). In one embodiment, a fuel credit is generated or caused to be generated at least in part due to an amount of RNG injected into the DS (i.e., when an equivalent amount is withdrawn for transportation use). In one embodiment, the fuel credit may be generated in association with the withdrawn gas that is used as a transportation fuel, or a transportation fuel resulting from the withdrawn gas.

Further advantageously, RNG may provide a clean, easily controlled source of renewable transportation fuel from organic waste materials and may replace fossil transportation fuels with a sustainable reduced carbon fuel option. Biogas offers an environmentally friendly replacement for fossil natural gas, however, in practice, the capital and/or operation costs associated with establishing and/or operating a biogas upgrading plant may be prohibitive. While the goal of upgrading biogas is generally to provide a renewable fuel that is interchangeable with and/or may replace a fossil fuel, it has been found that using natural gas (e.g., fossil natural gas) in the upgrading process and/or for enriching the tail gas may improve profitability of upgrading the biogas, and thus may incentivize the upgrading of biogas.

In accordance with one aspect of the instant invention there is provided a method for providing upgraded biogas comprising: feeding biogas into a biogas upgrading system, said biogas upgrading system producing upgraded biogas; enriching tail gas produced by the biogas upgrading system with natural gas to provide an enriched tail gas, said enriching comprising feeding natural gas withdrawn from a distribution system into at least one of the biogas upgrading system and the tail gas; providing at least a portion of the enriched tail gas to a combustion system, said combustion system configured to produce at least one of heat and electricity; and feeding at least a portion of the upgraded biogas to the distribution system, wherein an amount of natural gas withdrawn from the distribution system for said enriching is at least 50% of an amount of upgraded biogas fed into the distribution system, each of said amount of natural gas and said amount of upgraded biogas measured as energy delivered over a period of time.

In accordance with one aspect of the instant invention there is provided method for providing upgraded biogas comprising: feeding biogas into a biogas upgrading system, said biogas upgrading system producing a $CH_4$-rich gas and a $CH_4$-depleted gas; enriching a tail gas with natural gas to provide an enriched tail gas, said tail gas comprising gas from the $CH_4$-depleted gas, said enriching comprising feeding a stream of natural gas withdrawn from a distribution system into at least one of the biogas upgrading system and the tail gas; feeding at least a portion of the enriched tail gas to a combustion system, said combustion system configured to produce at least one of heat and electricity; and feeding upgraded biogas to the distribution system, said upgraded biogas comprising gas from the $CH_4$-rich gas stream, wherein enriching the tail gas with natural gas comprises selecting a flow of the stream of natural gas to be sufficient to provide the enriched tail gas with a heating value that is at least 75% of a heating value of the biogas fed to the upgrading system.

In accordance with one aspect of the instant invention there is provided a biogas upgrading system comprising: an inlet for receiving biogas; a separating system configured to remove carbon dioxide from the biogas received at the inlet, said separating system for producing upgraded biogas and tail gas, said tail gas comprising at least a portion of the removed carbon dioxide; a natural gas inlet configured to provide natural gas for enriching the tail gas and producing an enriched tail gas, said natural gas inlet disposed to feed a stream of natural gas to at least one of the separating system and the tail gas, said stream of natural gas withdrawn from a distribution system; a first outlet configured to provide at least a portion of the upgraded biogas to the distribution system; a second outlet configured to provide at least a portion of the enriched tail gas to a combustion system for combusting the enriched tail gas stream, said combustion system configured to provide at least one of heat and electricity, said combustion system configured to combust gas having a methane content that is at least 75% of a methane content of the biogas.

In accordance with one aspect of the instant invention there is provided a method for providing upgraded biogas comprising: feeding biogas into a biogas upgrading system, said biogas upgrading system comprising a separating system configured to remove carbon dioxide from the biogas, said biogas upgrading system having a first outlet configured to provide a $CH_4$-rich upgraded biogas and a second outlet configured to provide a $CH_4$-depleted tail gas, said tail gas comprising carbon dioxide removed from the biogas; feeding a stream of natural gas into the separating system such that the tail gas is enriched with natural gas, wherein said stream of natural gas is conveyed with the carbon dioxide removed from the biogas to the second outlet.

In accordance with one aspect of the instant invention there is provided a biogas upgrading system comprising: a separating unit configured to remove carbon dioxide from biogas to provide upgraded biogas and tail gas, said separating system including a first inlet configured to receive the biogas, a second inlet configured to receive natural gas; a first outlet configured to provide the upgraded biogas, and a second outlet configured to provide the tail gas, said separating unit configured to provide the natural gas as a sweep gas that is conveyed with the carbon dioxide removed from the biogas to the second outlet.

In accordance with one aspect of the instant invention there is provided a method for providing upgraded biogas comprising: obtaining biogas from a biogas source that produces raw biogas comprising carbon dioxide and methane; feeding the biogas into a biogas upgrading system, said biogas upgrading system producing upgraded biogas and tail gas; enriching the tail gas with natural gas to provide an enriched tail gas, said enriching comprising feeding a stream of natural gas withdrawn from a distribution system to at least one of the biogas upgrading system and the tail gas; wherein an amount of the natural gas used to enrich the tail gas stream is selected to provide the enriched tail gas with a heating value that is at least 75% of the average heating value of the raw biogas.

In accordance with one aspect of the instant invention there is provided a method for providing upgraded biogas comprising: feeding biogas into a biogas upgrading system, said biogas upgrading system for producing $CH_4$-rich upgraded biogas and $CH_4$-depleted tail gas; feeding natural gas withdrawn from a distribution system into a turboexpander, said turboexpander reducing a pressure of the natural gas; enriching the $CH_4$-depleted tail gas with the natural gas having the reduced pressure to provide an enriched tail gas, said enriching comprising at least one of feeding the natural gas having reduced pressure into the biogas upgrading system and mixing the natural gas having reduced pressure with the $CH_4$-depleted tail gas; and feeding at least a portion of the $CH_4$-rich upgraded biogas to a compressor to compress the $CH_4$-rich upgraded biogas to a pressure suitable for injection into the distribution system, wherein said compressor is at least partially driven by energy provided by the turboexpander.

In accordance with one aspect of the instant invention there is provided a method for providing upgraded biogas comprising: feeding biogas into a biogas upgrading system, said biogas upgrading system producing upgraded biogas and a tail gas; enriching the tail gas with natural gas to provide an enriched tail gas, said enriching comprising feeding natural gas withdrawn from a distribution system into at least one of the biogas upgrading system and the tail gas; feeding at least a portion of the enriched tail gas to at least one combustion system, said at least one combustion system for producing at least one of heat and electricity; and feeding the upgraded biogas to the distribution system, wherein for every BTU/day of upgraded biogas fed to the distribution system, at least half a BTU/day of natural gas is withdrawn from the distribution system.

In accordance with one aspect of the instant invention there is provided a method for providing upgraded biogas comprising: feeding biogas into a biogas upgrading system, said biogas upgrading system having at least one outlet for providing a $CH_4$-rich gas stream and at least one outlet for providing a $CH_4$-depleted gas stream; enriching a tail gas with natural gas to provide an enriched tail gas, said tail gas comprising gas from the $CH_4$-depleted gas stream, said enriching comprising feeding natural gas withdrawn from a distribution system into at least one of the biogas upgrading system and the tail gas; feeding at least a portion of the enriched tail gas to at least one combustion system, said at least one combustion system configured to produce at least one of heat and electricity; and feeding upgraded biogas to the distribution system, said upgraded biogas comprising gas from the $CH_4$-rich gas stream; wherein for every BTU/day of upgraded biogas fed to the distribution system at least half a BTU/day of natural gas is withdrawn from the distribution system for said enriching.

In accordance with one aspect of the instant invention there is provided a method for providing upgraded biogas comprising: feeding biogas into a biogas upgrading system, said biogas upgrading system having at least one outlet for providing a $CH_4$-rich gas stream and at least one outlet for providing a $CH_4$-depleted gas stream; enriching a tail gas with natural gas to provide an enriched tail gas, said tail gas comprising gas from the $CH_4$-depleted gas stream, said enriching comprising feeding natural gas withdrawn from a distribution system into at least one of the biogas upgrading system and the tail gas; feeding at least a portion of the enriched tail gas to at least one combustion system, said at least one combustion system configured to produce at least one of heat and electricity; and feeding upgraded biogas to the distribution system, said upgraded biogas comprising gas from the $CH_4$-rich gas stream; wherein said natural gas withdrawn from the distribution system is fed into the at least one of the biogas upgrading system and the tail gas in an amount selected to provide the enriched tail gas with a methane content of at least 40%.

In accordance with one aspect of the instant invention there is provided a method for providing renewable natural gas for transportation use, said method comprising: removing at least some $CO_2$ from a stream of biogas to produce a first stream of $CH_4$-rich gas stream and a second stream of $CH_4$-depleted gas; enriching a tail gas with natural gas withdrawn from a distribution system to provide an enriched tail gas, said tail gas comprising gas from the second stream of $CH_4$-depleted gas; providing at least a portion of the enriched tail gas to a combustion system, said combustion system configured to produce at least one of heat and electricity; feeding renewable natural gas to the distribution system, said renewable natural gas comprising gas from the first $CH_4$-rich gas stream, and generating a fuel credit associated with transportation use of the renewable natural gas fed to the distribution system, wherein an amount of natural gas withdrawn from the distribution system for said enriching is at least 50% of an amount of renewable natural gas fed into the distribution system, each of said amount of natural gas and said amount of renewable natural gas measured as MMBTU/hr.

DETAILED DESCRIPTION

Figure 1A:
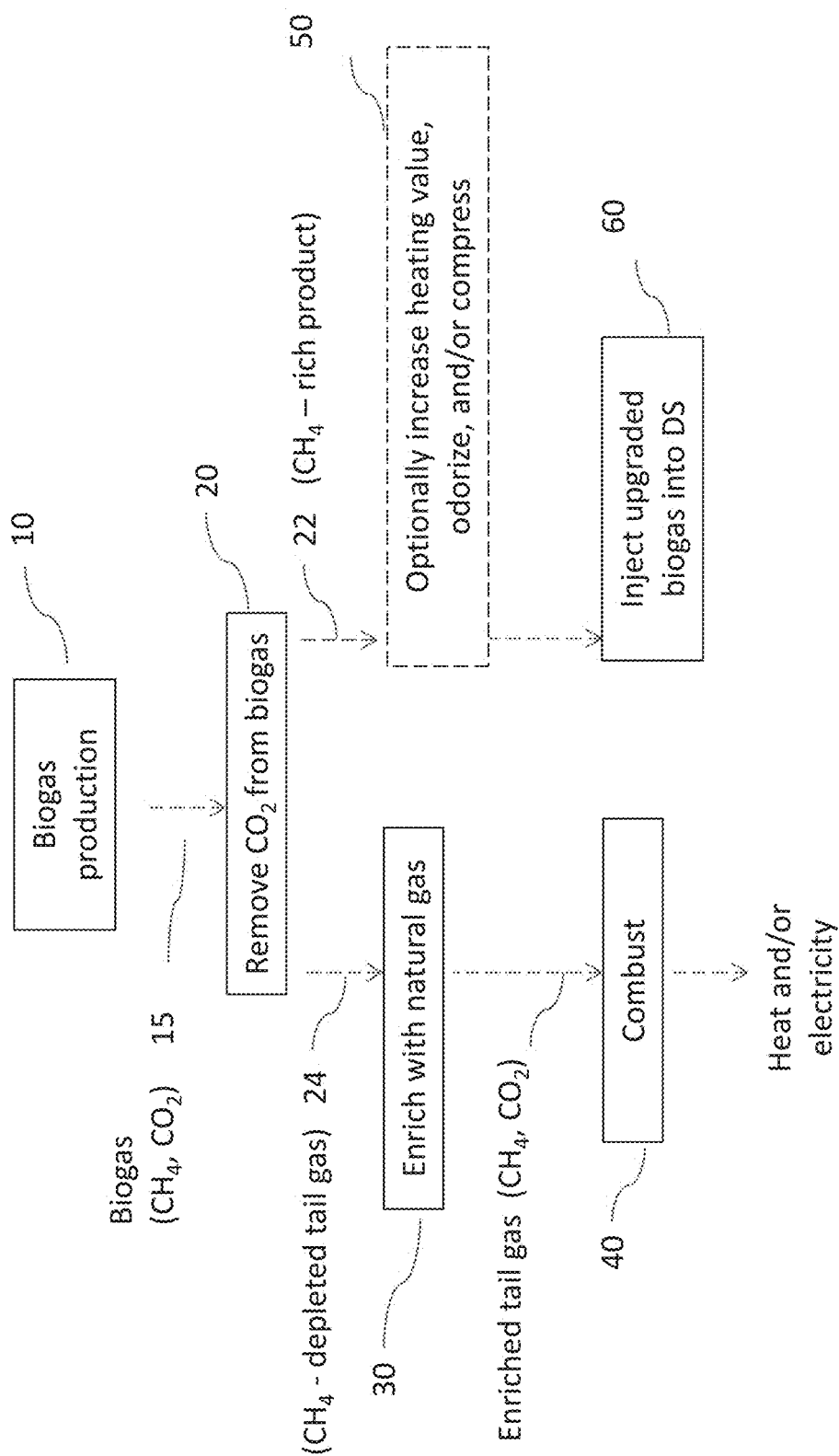
FIG. 1a is a block flow diagram of a method according to one embodiment of the invention.

Certain exemplary embodiments of the invention now will be described in more detail, with reference to the drawings, in which like features are identified by like reference numerals. The invention may, however, be embodied in many different forms and should not be construed as limited to the embodiments set forth herein. The terminology used herein is for the purpose of describing certain embodiments only and is not intended to be limiting of the invention. For example, as used herein, the singular forms "a," "an," and "the" may include plural references unless the context clearly dictates otherwise. The terms "comprises", "comprising", "including", and/or "includes", as used herein, are intended to mean "including but not limited to." The term "and/or", as used herein, is intended to refer to either or both of the elements so conjoined. The phrase "at least one" in reference to a list of one or more elements, is intended to refer to at least one element selected from any one or more of the elements in the list of elements, but not necessarily including at least one of each and every element specifically listed within the list of elements. Thus, as a non-limiting example, the phrase "at least one of A and B" may refer to at least one A with no B present, at least one B with no A present, or at least one A and at least one B in combination. In the context of describing the combining of components by the "addition" or "adding" of one component to another, or the separating of components by the "removal" or "removing" of one component from another, those skilled in the art will understand that the order of addition/removal is not critical (unless stated otherwise). The terms "remove", "removing", and "removal", with reference to one or more impurities, contaminants, and/or constituents of biogas, includes partial removal. The terms "cause" or "causing", as used herein, may include arranging or bringing about a specific result (e.g., a withdrawal of a gas), either directly or indirectly, or to play a role in a series of activities through commercial arrangements such as a written agreement, verbal agreement, or contract. The term "associated with", as used herein with reference to two elements (e.g., a fuel credit associated with the transportation fuel), is intended to refer to the two elements being connected with each other, linked to each other, related in some way, dependent upon each other in some way, and/or in some relationship with each other. The terms "first", "second", etc., may be used to distinguish one element from another, and these elements should not be limited by these terms. Unless defined otherwise, all technical and scientific terms used herein have the same meanings as commonly understood by one of ordinary skill in the art. If a definition or use of a term in the instant disclosure contradicts or conflicts with the same term defined in an incorporated reference, the definition provided in the instant disclosure supersedes the definition provided in the incorporated reference.

Referring to FIG. 1a, there is shown a method in accordance with one embodiment of the invention. In step 10, biogas is produced. The biogas 15 may be produced from a single source, or a plurality of sources. For example, in one embodiment, the biogas 15 is produced by multiple biogas plants, each of which feeds biogas into a biogas pipeline or pipeline system. In step 20, the biogas 15, which contains both $CH_4$ and $CO_2$, is subject to a process that removes at least some of the $CO_2$ to produce upgraded biogas 22 (e.g., a $CH_4$-rich product stream) and tail gas comprising $CO_2$ 24 (e.g., a $CH_4$-depleted stream and/or a $CO_2$-rich stream). In step 30, the tail gas 24 is enriched with natural gas, thereby providing an enriched tail gas. In step 40, the enriched tail gas is combusted to provide at least one of heat (e.g., steam) and electricity. Step 50 is an optional step, wherein the heating value of the upgraded biogas 22 is increased (e.g., by adding propane, natural gas, liquefied petroleum gas (LPG) and/or another suitable fuel) and/or the upgraded biogas 22 is odorized and/or compressed. In step 60, the upgraded biogas 22 (e.g., RNG) is injected into a DS. Optionally, step 60 includes compressing the upgraded biogas. Alternatively, the upgraded biogas 22 is compressed to provide compressed natural gas (CNG) or liquefied natural gas (LNG) for storage and/or transportation use. In another optional step (not shown), natural gas having the environmental attributes of the injected biogas 22 is withdrawn from any point on the DS for use as transportation fuel. Optionally, a fuel credit associated with the transportation fuel is generated.

Figure 1B:
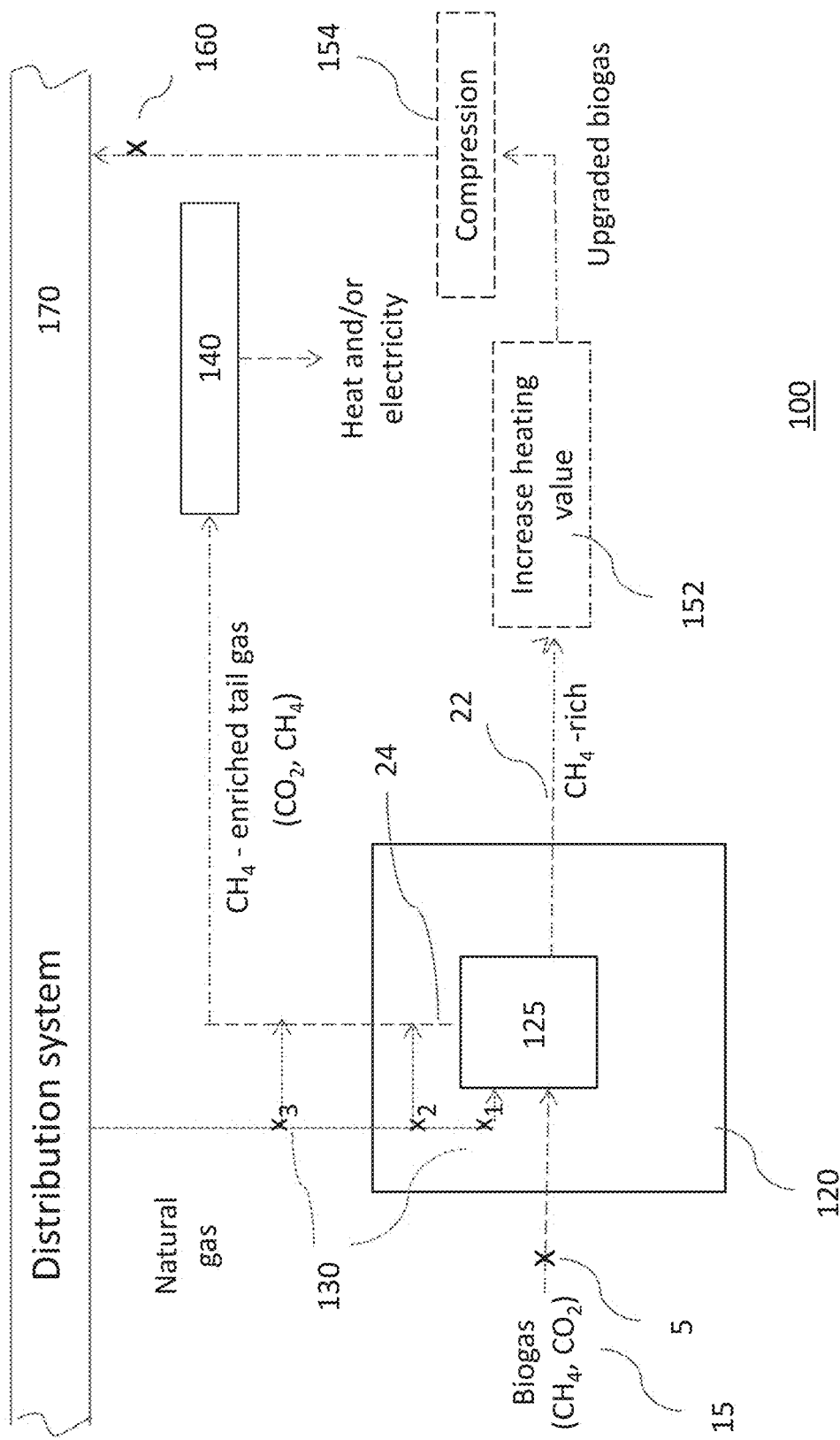
FIG. 1b is a schematic diagram showing a system for providing upgraded biogas in accordance with one embodiment of the invention.

Referring to FIG. 1b, there is shown a system in accordance with one embodiment of the invention. The system 100 for providing upgraded biogas includes an inlet 5 for receiving biogas 15 (e.g., from a biogas pipeline or pipeline system or storage container). The biogas 15 is fed to a biogas upgrading system 120, which includes a separating system 125 and optionally includes one or more biogas cleaning systems (not shown in FIG. 1b). The separating system 125 removes at least some of the $CO_2$ from the biogas, thereby providing upgraded biogas 22 (e.g., a $CH_4$-rich product stream) and tail gas comprising $CO_2$ 24 (e.g., $CH_4$-depleted stream). An enriching system 130 is provided to enrich the tail gas 24 with natural gas. In one embodiment, the natural gas for enriching is withdrawn from a distribution system 170. In one embodiment, the enriching system 130 includes a pipeline or pipeline system carrying the withdrawn natural gas in addition to one or more valves, monitors, and/or controllers for controlling and/or measuring a flow rate of the natural gas used for enriching. In one embodiment, the enriching system 130 includes a mixing device. In one embodiment the enriching system 130 includes a turboexpander (not shown). As illustrated by the dashed lines, the enriching system 130 may be disposed at different locations depending on how and/or where the tail gas is to be enriched. For example, the system 100 may be configured so that the natural gas used for enriching the tail gas is introduced within the biogas upgrading system 120 and/or to the tail gas 24. In embodiments where the system 100 is configured to introduce the natural gas within the upgrading system 120, it may be introduced into the separating system 125 (e.g., at $X_1$), into one or more cleaning systems (not shown), or to the tail gas 24 (e.g., at $X_2$). In embodiments where the system 100 is configured to introduce the natural gas to the tail gas 24, the natural gas may be introduced within the upgrading system 120 (e.g., at $X_2$) or external to the upgrading system (e.g., at $X_3$). In one embodiment, tail gas is obtained from an outlet of the separating system 125 and/or upgrading system 120 and is used directly in the natural gas enriching step. In one embodiment, the tail gas is cleaned (e.g., to remove $H_2S$, water, siloxanes, and/or another impurity) and/or is introduced to an additive prior to the enriching step. In one embodiment, the natural gas is introduced into a cleaning system disposed downstream of the separating system 125.

In embodiments where the system 100 is configured to introduce the natural gas to tail gas 24, the enriching system 130 may include a mixing device or system (not shown) to facilitate rapid and/or thorough mixing. In embodiments where the system 100 is configured to introduce the natural gas into the separating system 125, the natural gas may be used to improve and/or facilitate the separation. For example, in one embodiment, the natural gas is provided as a sweep or purge stream. In one embodiment, the natural gas is introduced into one or more cleaning systems downstream or upstream of the separating system. For example, in one embodiment, the natural gas is provided as a purge gas in a cleaning system used to remove siloxanes from tail gas. In embodiments wherein natural gas is introduced into the separating system 125, it is generally introduced such that it does not feed into the CH₄-rich stream produced by the separating system 125. A combustion system 140 is provided to combust the enriched tail gas stream and to provide heat and/or electricity therefrom. Optionally, the system 100 includes a system 152 for increasing the heating value of the upgraded biogas 22, an odorization system (not shown) for introducing a stenching agent, and/or one or more compressors 154 for compressing the upgraded biogas 22 (e.g., to meet the specifications of that section of the distribution system 170). The upgraded biogas 22 is then fed to the distribution system 170, wherein it may be injected at injection site 160. Analytical instrumentation may be provided at or near the injection site 160 to measure the quantity and quality (e.g., heating value and/or contaminants) of the upgraded biogas. The distribution system further includes a withdrawal point (not shown), from which natural gas having or associated with the environmental attributes of the injected upgraded biogas may be withdrawn for transportation use.

In embodiments wherein RNG is produced by the system illustrated in FIG. 1b, the biogas 15 may be provided by a party referred to as the biogas producer, the biogas may be upgraded by a party referred to as the biofuel producer (e.g., which may be the same or different from the biogas producer), and the RNG may be injected into the DS by a party referred to as the biofuel injector (e.g., which may be the same or different from the biofuel producer).

In one embodiment, the system for increasing the heating value 152, the odorization system (not shown), and/or one or more compressors 154 for compressing the upgraded biogas 22 are provided by the biofuel producer. In another embodiment, one or more of these options is provided by the biofuel injector (e.g., if different from the biofuel producer).

In one embodiment, the injection site 160 is an injection point. The term "injection point", as used herein, refers to the location where a gas is fed into the DS so as to ultimately combine with other gas carried within the DS. In one embodiment, the injection point is a point where gas quantity is measured. In one embodiment, the injection point is a location where gas quantity and/or quality is measured. In one embodiment, the injection point is a location where custody is transferred.

In one embodiment, the system 100 includes a turboexpander (not shown), which may or may not be part of the enriching system 130. A turboexpander is a centrifugal or axial flow turbine through which a high pressure gas is expanded to produce work. For example, a turboexpander typically includes a turbine connected to a load device (e.g., a compressor, a generator, or brakes) by a shaft. In one embodiment, the turboexpander is disposed to receive natural gas from the distribution system 170 (e.g., which is at a relatively high pressure) and to provide the natural gas for enriching (e.g., which may be at a lower pressure). As the high pressure natural gas flows into the turboexpander it spins the centrifugal or axial flow turbine. The kinetic energy from the pressure letdown may thus be converted into useful mechanical energy, which may be used to drive a compressor or generator (e.g., for producing electricity or for direct drive of a compressor).

In one embodiment, the turboexpander (not shown) drives, at least in part, the grid compressor used to compress the upgraded biogas 22 prior to injection into the distribution system 170 (e.g., directly or indirectly through the electricity generated). In addition to capturing and reusing the energy associated with the pressure letdown (e.g., which may at least partially offset the energy required to compress the upgraded biogas), the turboexpander may provide cooling power for reducing the heat generated upon compressing. In particular, there may be an at least partial offset of both energy and temperature.

In another embodiment, the turboexpander (not shown) drives, at least in part, the compressor used to compress the raw biogas 15 and/or is used to generate electricity for use in the upgrading process.

Providing a turboexpander (not shown) is particularly advantageous when the amount of natural gas used in the enriching process is at least half the amount of upgraded biogas injected into the DS. In this case, using the turboexpander may provide a substantial reduction in the net energy required for injecting the upgraded biogas into the DS. This is particularly valuable when the DS pressure is high.

Biogas Production

In general, the biogas 15 is produced by the breakdown of organic matter in low oxygen conditions. In particular, it may be produced by the anaerobic digestion or fermentation of organic matter in the absence of oxygen. Anaerobic digestion, which refers to the biological breakdown of organic matter by anaerobic microorganisms, may involve a series of microorganism types and processes (e.g., hydrolysis, acidogenesis, acetogenesis, and methanogenesis).

In general, the biogas 15 may be produced naturally or in a controlled environment. With regard to the former, the biogas may be produced in and collected from a landfill. With regard to the latter, the biogas may be produced in a dedicated digester (e.g., an anaerobic digester).

In one embodiment, the biogas 15 is produced by anaerobic digestion in one or more anaerobic digesters. Each anaerobic digester may be a holding tank, or other contained volume, such as a covered lagoon or a sealed structure, designed to facilitate the breakdown of organic matter by microorganisms under anaerobic or low oxygen conditions. The one or more anaerobic digesters may be connected in series and/or in parallel. In a single-stage digestion system (one-stage), all of the anaerobic reactions occur within a single, sealed digester. In a two-stage digestion system (multistage), different anaerobic digesters are optimized to bring maximum control over the bacterial communities living within the digesters.

In general, each anaerobic digester may be designed and/or operated in a number of configurations including batch or continuous, mesophilic or thermophilic temperature ranges, and low, medium, or high rates. In general, a batch digester is filled, sealed until it has produced all the biogas it can, emptied, and filled again, whereas a continuous digester is loaded regularly (e.g., steadily, hourly, daily, weekly, etc.) such that the digester is not fully emptied between loadings. Some examples of continuous digesters include vertical chamber digesters (e.g., single or double chamber) and horizontal plug flow digesters. The rate refers to the reduction (or digestion) of chemical oxygen demand (COD) per unit of volume to the unit, which is a rate measurement based on the removal of organic compounds present in the feed. In practice, the configuration utilized will depend on a number of factors, including, for example, the nature of the organic matter fed to the anaerobic digester and/or the level of digestion required. Other factors that may be considered in the configuration choice include operating parameters such as residence time, temperature, pH, and/or the nutrients supplied. Design choices also include provisions for handling or concentrating microbes, such as membranes, packing, settling, and recycling.

In general, the organic matter from which the biogas is produced may include any organic matter and/or biomass (e.g., manure, sewage sludge, municipal solid waste, biodegradable waste, biodegradable feedstock, etc.). For example, in one embodiment, the organic matter may include organic compounds that have come from the remains of organisms such as plants, animals, and/or their waste products. The organic matter may be in liquid form, solid form, and/or gaseous form.

In one embodiment, the biogas 15 is produced in a landfill site from landfill waste. In this embodiment, the landfill waste, which may covered and compressed as a result of the weight of additional material deposited thereon, decomposes under anaerobic conditions via anaerobic microbes. By appropriately engineering a collection system at the landfill site, the resultant biogas may be captured. In this embodiment, the biogas may be referred to as landfill gas (LFG).

In one embodiment, the biogas 15 is produced from one or more anaerobic digesters designed for use with manure (e.g., dairy cow manure). Optionally, the one or more anaerobic digesters are also fed other farm wastes such as milkroom waste water, straw, corn husks, grass, and leaves. Optionally, the pH level and/or carbon-to-nitrogen (C/N) level of the raw feed is adjusted to values that increase the efficiency of biogas production (e.g., a pH of around 7). For example, sawdust, which has a high C/N ratio, may be added to poultry manure, which has a low C/N ratio.

In one embodiment, the biogas 15 is produced from one or more anaerobic digesters designed for use in a wastewater treatment plant. The principal feedstock for anaerobic digesters in a wastewater treatment plant may be sewage sludge (e.g., both primary and secondary sludge). In one embodiment, waste activated sludge (e.g., secondary sludge), optionally thickened, and primary sludge is fed to an anaerobic digester at a dry solids (DS) concentration of up to about 4%.

In one embodiment, the biogas 15 is produced from one or more anaerobic digesters used to treat wastewater, wastes, and/or residues from an industrial process. For example, in one embodiment, the biogas is produced in one or more anaerobic digesters used to treat residues and/or waste from a cellulosic ethanol process. In this case, the feedstock may include the residues remaining after obtaining sugar from plant biomass such as sugar cane bagasse, sugar cane tops and/or leaves, beet pulp, or may include residues remaining after grain processing, such as corn fiber, corn stover, or bran from grains. In one embodiment, the biogas is produced in one or more anaerobic digesters used to treat residues and/or waste from grain processing (e.g., a wheat process, starch production, brewery alcohol, etc.). In another embodiment, the biogas is produced in one or more anaerobic digesters used to treat residues, byproducts, waste, or non-waste material from processing of hardwood and/or softwood species. For example, the residues may include residues from pulp and paper processing.

In one embodiment, the biogas is produced in one or more anaerobic digesters used to treat residues and/or waste from a process involving the processing of lignocellulosic feedstock. In one embodiment, the lignocellulosic feedstock is (i) an energy or biomass crop, (ii) an agricultural residue, and/or hardwood or softwood. In one embodiment, the lignocellulosic feedstock is a non-woody lignocellulosic feedstock such as (i) an energy crop, (ii) residues, byproducts or waste from processing of plant biomass or feedstock derived therefrom in a facility, and/or (iii) agricultural residues. In one embodiment, the lignocellulosic feedstock is a non-woody lignocellulosic feedstock such as (i) an energy crop and/or an agricultural residue. In one embodiment, the lignocellulosic feedstock is straw, stover, and/or switch grass.

In one embodiment, the biogas 15 is produced from one or more anaerobic digesters fed with a purpose-grown energy crop (e.g., beets, maize, or grass silage). Anaerobic digesters used for processing dedicated energy crops may achieve higher levels of degradation and biogas production than those fed only manure or sewage sludge.

In one embodiment, gas production of an anaerobic digester (e.g., manure or sewer sludge based) is improved by co-digesting the primary feedstock with another feedstock such as a purpose-grown energy crop. In another embodiment, gas production of an anaerobic digester (e.g., manure or sewer sludge based) is improved by co-digesting the primary feedstock with another feedstock such as agricultural waste or slaughterhouse waste.

In one embodiment, the biogas 15 is produced from source separated organics (SSOs). For example, residential SSOs may be obtained from the collection of household organic wastes via a residential Green Bin and/or yard waste program, whereas commercial SSOs may be obtained from industrial, commercial, and/or institutional facilities such as restaurants, hotels, hospitals, and food processing plants.

In general, different feedstocks may break down at different rates. For example, since some feedstocks are more biodegradable than others, the average residence time in a digester may be 24 hours, several weeks, or several months. For example, the residence time may be between 15 and 40 days for a typical two-stage mesophilic digestion, or around 14 days for a single-stage thermophilic digestion.

In general, different feedstocks also may provide different biogas compositions. For example, although biogas is known to be predominately methane ($CH_4$) and carbon dioxide ($CO_2$), with relatively small amounts of hydrogen sulfide ($H_2S$), ammonia ($NH_3$), hydrogen ($H_2$), nitrogen ($N_2$), carbon monoxide (CO), oxygen ($O_2$), water vapour, and/or siloxanes, the ratios may vary. In particular, the $CH_4$ content of biogas may vary between about 35% and 70% (e.g., average of about 60%), whereas the $CO_2$ content may vary between about 15% and 65% (e.g., average of about 45%), depending on the biomass. For example, conventional biogas plants may have a methane content between about 60 and 70%, whereas biogas from a landfill site may have a methane content between about 25 and 65%. In one embodiment, the collective amount of gases other than $CH_4$ and $CO_2$ in the biogas is less than about 10%. The percentages used to quantify gas composition and/or a specific gas content, as used herein, are expressed as mol %, unless otherwise specified.

In one embodiment, the biogas 15 is produced by a single biogas plant. In one embodiment, the biogas 15 is produced by multiple biogas plants that feed the biogas produced therein into a biogas grid. In one embodiment, the biogas grid feeds the biogas to a biogas hub, wherein it may be cleaned and/or upgraded.

Biogas Cleaning

Optionally, the biogas 15 is cleaned to remove water, hydrogen sulfide ($H_2S$), and/or other impurities such as nitrogen ($N_2$), oxygen ($O_2$), ammonia ($NH_3$), siloxanes, and particulates. In addition, it may be desirable to remove Volatile Organic Compounds (VOCs) (e.g., limonene and/or other terpenes). The purpose of cleaning the biogas is to remove one or more impurities, contaminants, and/or constituents apart from $CO_2$. More specifically, although some $CO_2$ may be removed in the cleaning step, the optional cleaning step(s) is/are intended to supplement the biogas upgrading step wherein $CO_2$ is removed from the biogas. The biogas 15 may be cleaned prior to entering the biogas upgrading system 120, within the biogas upgrading system 120, and/or after exiting the biogas upgrading system 120. Impurities in the raw biogas may be removed by any suitable method, or combination of methods, as known in the art.

Water ($H_2O$) may be removed from the biogas by cooling, compression, absorption, adsorption, and/or coalescing filtration. For example, water may be removed by increasing the pressure or decreasing the temperature in order to cause the water to condense so that it may be removed. Alternatively, water may be removed by adsorption using silicon dioxide ($SiO_2$), activated carbon, or molecular sieves (e.g., pressure swing adsorption). In one embodiment, sufficient water is removed to reduce the moisture content to below a certain threshold (e.g., 1.4%). The degree of dehumidification required may depend on pipeline standards of the commercial distribution system 170, the combustion system 140, and/or the technology used in the separating system 125. Water vapour may be problematic since it may condense into water or ice when passing from high to low pressure systems, which may cause corrosion, may result in clogging, may interfere with gas flow and pressure measurements (e.g., causing system control problems), and/or may cause failure of the combustion equipment (e.g., compressor lube oil filters and internal lubricated parts). Removing water from biogas may prevent condensation, and moreover, may help optimize the $CO_2/CH_4$ separation process and/or combustion process. For example, if the combustion equipment includes an engine, removing water may protect the engine, reduce engine maintenance requirements, extend service life, and/or improve oil life.

Hydrogen sulfide ($H_2S$) may be removed from the biogas by adsorption on activated carbon (e.g., impregnated activated carbon such as ZnO impregnated carbon), adsorption on molecular sieve, adsorption using iron oxides (e.g., iron oxide impregnated wood chips (iron sponge)), iron oxide pellets, or proprietary iron-oxide media), physical absorption (e.g., water scrubbing), chemical absorption (e.g., NaOH washing), and/or biofilters or biotrickling filters (e.g., where the biogas is forced through a moist, packed bed that contains microorganisms). Some $H_2S$ may also be removed during the water removal step, if present. Pipeline standards may require a $H_2S$ concentration that is less than 16 ppm, 8 ppm, 3 ppm, or some other value, depending on the pipeline. Biogas combustion equipment may have maximum recommended $H_2S$ content (e.g., less than 200 ppm). The presence of $H_2S$ in biogas is generally undesired because it causes odours, is corrosive, and produces sulfur emissions when the biogas is combusted. The removal of $H_2S$ may be required to protect the combustion equipment, particularly, when the combustion equipment includes an internal combustion engine or turbine. For example, while boilers may be able to withstand concentrations of $H_2S$ up to 1000 ppm, internal combustion engines may require the $H_2S$ concentration to be below 100 ppm.

Nitrogen ($N_2$) may be removed from the biogas by pressure swing absorption (PSA), membranes, and/or cryogenic systems. Oxygen ($O_2$) may be removed by catalytic oxidation, membranes, or low pressure PSA. While $N_2$ and $O_2$ are not typically found in high concentrations in agricultural and/or farm based biogas, they, and in particular $N_2$, may be present in higher concentrations in landfill based biogas. The $O_2$ and/or $N_2$ present in biogas can vary over time and negatively affect the purity of the RNG, sometimes making it unsuitable for introduction directly into a natural gas pipeline.

Siloxanes may be removed from the biogas by filtration (e.g., activated alumina, activated carbon, graphite filtration, or silica gels, which absorb siloxanes from biogas), by condensation or cryogenic techniques, using synthetic resins, using liquid absorbents (e.g., Selexol™), using membranes, and/or using biological processes. The term "siloxanes" refers to a class of organosilicon compounds characterized by "Si—O—Si" linkages. Siloxanes, which are often associated with biogas sourced from landfill sites and/or sewage gas plants, may be formed from the anaerobic decomposition of materials commonly found in soaps and detergents. Siloxanes may be problematic when biogas is used to produce heat and/or electricity, because during the combustion process, silicon may be released and may combine with free oxygen or various other elements in the combustion gas. As a result, a white mineral deposit (e.g., containing silica ($SiO_2$) or silicates ($Si_xO_y$)) may accumulate on the combustion equipment (e.g., on the hot surfaces inside the combustion equipment) and may need to be removed by chemical and/or mechanical methods. This accumulation may allow heat to build up where it shouldn't and/or may affect the maintenance intervals of the combustion equipment. For example, when biogas containing siloxanes is combusted in gas turbines, boilers, or combustion engines, deposits of solid silica ($SiO_2$) or silicates ($Si_xO_y$) may adhere to the turbine nozzles, turbine blades, cylinder heads, pistons, spark plugs, valves, and/or heat exchanger surfaces, causing wear, imbalance, fouling, and/or other serious problems. For example, deposits on spark plugs may cause pre-mature failure, fouling, and/or misfiring. Deposits on pistons and cylinder heads may be so abrasive that even a small amount may cause engine power reduction (e.g., by 10-20%), may necessitate more frequent oil changes, and/or may damage the engine. For example, a Caterpillar internal combustion engine may have a maximum recommended siloxane concentration of 28 mg/m$^3$. Limits for turbines may be considerably lower. Prolonged operation of gas turbines where siloxanes have not been removed can lead to erosion of turbine blades and a significant drop in operating efficiency of the turbine. For example, a Solar turbine may have a maximum recommended siloxane concentration of 5 mg/m$^3$. Removing the siloxanes avoids and/or at least reduces mineral deposits and may provide a more efficient process. In one embodiment, siloxanes are removed to the 100 parts-per-billion range. In one embodiment, siloxanes are removed to a concentration that is less than about 30 mg/m$^3$. In one embodiment, siloxanes are removed to a concentration that is less than about 15 mg/m$^3$. In one embodiment, siloxanes are removed to a concentration that is less than about 10 mg/m$^3$. In one embodiment, siloxanes are removed to a concentration that is less than about 3 mg/m$^3$. In one embodiment, siloxanes are removed to a concentration that is less than about 1 mg/m$^3$. In one embodiment, siloxanes are removed to a concentration that is less than about 0.1 mg/m$^3$. For biogas sourced from a wastewater treatment plant, the average siloxane concentration in biogas may be about 6.1 ppm or 38 mg/m$^3$, and may be as high as 60 mg/m$^3$. In one embodiment, siloxanes are removed as part of a water removal or dehumidifying process.

Particulates (e.g., dust and/or dirt) may be removed by mechanical filters, centrifugal separation, screens, etc. In one embodiment, particulates are removed by a coarse particulate filter (e.g., 25 microns).

In general, the impurities (e.g., water, $H_2S$, $N_2$, $O_2$, $NH_3$, and/or siloxanes), may be removed in a separate cleaning step and/or as part of the biogas upgrading. In embodiments wherein a separate cleaning step is provided, it may be conducted prior to and/or after the upgrading. Advantageously, cleaning the biogas prior to biogas upgrading can prevent corrosion and/or mechanical wear of the separating equipment. In addition, it may provide a tail gas stream 24 with fewer impurities. In one embodiment, the biogas production is configured to reduce the number and/or amounts of impurities in the biogas in order to provide a cleaner biogas, thus obviating the need for one or more cleaning steps. For example, in one embodiment a small amount of $O_2$ (e.g., air) is introduced into the headspace of the digester to encourage certain microorganisms to oxidize the $H_2S$, and thus remove $H_2S$ from the gas phase.

In general, biogas cleaning may be provided in one or more steps, depending on the impurities to be removed, the purity required, and/or the upgrading technology used. In one embodiment, a plurality of sequential biogas cleaning steps are provided prior to feeding the biogas to the separating system and/or biogas upgrading system. In one embodiment, one or more cleaning steps are provided prior to feeding the biogas to the separating system and/or upgrading system, while one or more cleaning steps (e.g., the same or different) are conducted on the $CH_4$-rich stream exiting the separating system. In one embodiment, one or more cleaning steps are provided prior to feeding the biogas to the separating system and/or upgrading system, while one or more cleaning steps (e.g., the same or different) are conducted on the $CH_4$-depleted stream exiting the separating system or the upgrading system. In one embodiment, one or more cleaning steps are conducted on the tail gas. Subjecting the tail gas to one or more cleaning steps prior to natural gas enrichment may be particularly advantageous in embodiments wherein the tail gas is used within the process prior to enrichment (e.g., as a purge gas where it may pick up contaminants) or in embodiments wherein the cleaning process is more efficient for the tail gas versus raw biogas (e.g., if a lower concentration of one component and/or a lower pressure improves cleaning efficiency). In one embodiment, the optional cleaning steps are selected in dependence on the source of the biogas (e.g., landfill versus agricultural waste) and/or on the upgrading technology.

In one embodiment, the system providing upgraded biogas 100 includes one or more cleaning systems disposed upstream and/or downstream of the separating system 125. In one embodiment, the upgrading system 120 includes one or more cleaning systems disposed upstream and/or downstream of the separating system 125. For example, in one embodiment, the one more cleaning systems are selected from a hydrogen sulfide cleaning system, a water removal system (e.g., which may also be referred to as a biogas dehumidification system, a gas drier, or water knock out system), a siloxane removal system, a $N_2$ removal system, a $O_2$ removal system, physical filters. In one embodiment, the one or more cleaning systems include gas analyzer(s), flow meter(s), and/or manual or auto bypass system(s).

Hydrogen sulfide cleaning systems are available commercially and/or may be built on site, as is known in the art. For example, a $H_2S$ cleaning system may be marketed as a desulfurization plant and/or may be available as a skid-mounted unit, depending on the technology on which it is based and on the scale of the operation. In one embodiment, the hydrogen sulfide cleaning system includes a wet scrubber. In one embodiment, the hydrogen sulfide cleaning system includes at least one media vessel and a regeneration system.

Biogas dehumidification systems/driers are available commercially and/or may be built on site, as is known in the art. For example, biogas dehumidification systems may include and/or be integrated with heat exchangers, water chillers, and water collectors. In one embodiment, the one or more cleaning units includes a biogas dehumidifier that has a gas to cold water heat exchanger integrated with an industrial grade water chiller. In one embodiment, the one or more cleaning systems include a commercially available biogas dehumidification system that is mounted on a skid frame. In one embodiment, the one or more cleaning systems includes more than one biogas dehumidification system. For example, in one embodiment, a first biogas dehumidification system is disposed upstream of the separating system 125 while a second biogas dehumidification system is provided downstream of the separating system 125.

$N_2$ and/or $O_2$ cleaning systems are available commercially and/or may be built on site (e.g., modular plants), as is known in the art. In one embodiment, the one or more cleaning systems include a PSA system for removing $N_2$. For example, in one embodiment, the PSA system includes four PSA vessels packed with an adsorbent having a pore size selected to exclude methane. For example, in one embodiment, the one or more cleaning systems includes a $N_2$ removing PSA system utilizing Guild technology (e.g., Molecular Gate™) or Adsorption Research Inc. technology. In one embodiment, the one or more cleaning systems includes one or more PSA vessels packed with an adsorbent selected to adsorb methane and exclude nitrogen. Advantageously, when a $N_2$ removing PSA system is provided downstream of a separating system 125 that provides a $CH_4$-rich stream containing primarily $CH_4$ and $N_2$ (e.g., other impurities were removed), the PSA system may provide relatively pure $CH_4$ and $N_2$ streams.

Siloxane removal systems are available commercially and/or may be built on site (e.g., modular), as is known in the art. In one embodiment, the one or more cleaning systems include a siloxane removal system. For example, in one embodiment, the siloxane removal system is based on an activated carbon process and includes two towers, each having a bed of activated carbon. In this embodiment, one tower is actively used (e.g., landfill gas is fed thereto such that the siloxanes stick to the adsorbent), while flow to the other one is diverted so that the saturated activated carbon therein may be emptied and refilled. In one embodiment, the siloxane removal system is based on regenerative absorption and includes one or more columns packed with activated carbon, activated alumina, silica gels, and/or molecular sieves. For example, in one embodiment, the adsorbent may be regenerated on site thermally (e.g., heating releases the trapped siloxanes so that the adsorption column is regenerated and can be used again). In this embodiment, commonly referred to as temperature swing adsorption (TSA), the siloxane removal system may generate the heat and/or use waste/recycled heat. In one embodiment, the siloxane removal system is based on vacuum swing adsorption and includes several towers packed with molecular sieves and/or activated carbon, one or more vacuum pumps, and motorized valves for selectively directing gas flow to allow cycling of each tower from adsorption to desorption mode. In embodiments, wherein the siloxane removal system includes an adsorption column or tower, the size of the tower will be selected in dependence upon the sorption capacity of the adsorbent material and the siloxane concentration in the biogas. In one embodiment, the siloxane removal system is based on membrane separation and includes one or more membrane modules that are selective for siloxane. In one embodiment, the siloxane removal system is based on biological processes and includes a bio-chemical filtering system that is fitted to the biogas line. In one embodiment, the siloxane removal system includes one or more columns packed with an adsorption media, and the tail gas is used to desorb siloxanes adsorbed on the media.

In general, the one or more cleaning systems are optional. For example, cleaning may be provided by the biogas producer (e.g., rather than the biogas upgrader) and/or may not be required as a result of the source of the biogas and/or the biogas upgrading technology used in the separating system 125. More specifically, the one or more cleaning systems may be selected based on what is required and/or desired, as would be appreciated by one skilled in the art.

For example, when the separating system 125 is based on membranes or pressure swing adsorption technologies, it may be advantageous to provide a biogas dehumidifier unit and/or a $H_2S$ removal unit (e.g., in any order) upstream of the separating system 125. If $N_2$ and/or $O_2$ are not sufficiently removed via the separating system 125, then a separate $N_2$ and/or $O_2$ removal system may be provided downstream of the separating system 125.

Biogas Upgrading

As used herein, the term "biogas upgrading" refers to removing at least $CO_2$ from biogas (e.g., raw or clean) to provide a $CH_4$-rich gas and a $CH_4$-depleted gas. The term "$CH_4$-rich", as used in the biogas context herein, is used to indicate that the concentration of biogas derived $CH_4$ in a gas is higher than that of the raw biogas from which it was derived. The term "$CH_4$-depleted", as used herein, is used to indicate that the concentration of biogas derived $CH_4$ in a gas is lower than that of the raw biogas from which it was derived. The term "upgraded biogas", as used herein, refers to a methane-containing gas obtained and/or derived from $CH_4$-rich gas provided by "biogas upgrading". The term "tail gas", as used in the biogas context herein, refers to a gas obtained and/or derived from $CH_4$-depleted gas resulting from "biogas upgrading" and containing at least a portion of the $CO_2$ removed from the biogas.

In one embodiment, the methane content of the upgraded biogas is greater than about 80%. In one embodiment, sufficient $CO_2$ is removed from the biogas to provide a $CH_4$-rich stream having a methane content that is greater than 95%. In one embodiment, sufficient $CO_2$ is removed from the biogas to provide a $CH_4$-rich stream that meets a distribution system standard. In one embodiment, sufficient $CO_2$ is removed from the biogas to provide RNG (e.g., >95% $CH_4$ and thus is substantially interchangeable with natural gas).

Referring to FIG. 1b, biogas upgrading is conducted using a biogas upgrading system 120, which includes a separating system 125 for separating at least some of the carbon dioxide ($CO_2$) in the biogas from some of the methane ($CH_4$) in the biogas and optionally includes one or more other components/devices (not shown) (e.g., cleaning systems, compressors, valves, turboexpanders, gas analyzers, mixers, and/or high heating value gas inlets (not shown)).

In one embodiment, the separating system 125 includes an inlet for receiving a stream of biogas (e.g., raw or clean), a first outlet that provides upgraded biogas 22 (e.g., a $CH_4$-rich stream), and a second outlet that provides tail gas 24 that contains at least some of the $CO_2$ removed from the biogas. Biogas upgrading may be independent from biogas cleaning and/or integrated with biogas cleaning, depending on the technology used in the separating system 125.

The separating system 125 may be based on any technology wherein $CO_2$ may be separated from $CH_4$. For example, in one embodiment the separating system 125 is based on: absorption (e.g., water scrubbing, organic physical scrubbing, chemical scrubbing), pressure swing adsorption (PSA), membrane permeation, or cryogenic upgrading.

In one embodiment the separating system 125 is a multiple stage separation system based on at least two of the following: absorption (e.g., water scrubbing, organic physical scrubbing, chemical scrubbing), pressure swing adsorption (PSA), membrane permeation, and cryogenic upgrading.

Absorption

The principle behind absorption techniques is that some compounds are more soluble than others in select liquids. In terms of biogas upgrading, absorption techniques typically rely on $CO_2$ being more soluble than $CH_4$ in select liquids. Accordingly, when biogas is pressurized and fed to the bottom of a packed column while the liquid is fed on the top of the column in a counter-flow manner, the liquid leaving the column at the bottom will have a higher concentration of $CO_2$ while the gas leaving the top of the column will have a higher concentration of $CH_4$.

Different absorption technologies use different types of absorbents. For example, water scrubbing, which is a common biogas upgrading technique, may be used to remove $CO_2$ and $H_2S$ from biogas since both of these gases are more soluble in water than $CH_4$. The water that exits the column (e.g., with absorbed $CO_2$ and/or $H_2S$) may be regenerated and re-circulated back to the absorption column. Regeneration may be accomplished by de-pressuring (e.g., flashing) and/or by stripping with air in a similar column.

In organic physical scrubbing techniques the liquid is an organic solvent (e.g., polyethylene glycol). Polyethylene glycol scrubbing relies on the same underlying mechanism as water scrubbing (e.g., it works because both $CO_2$ and $H_2S$ are more soluble than $CH_4$ in the solvent).

In chemical scrubbing techniques, the liquid may be an amine solution. In this case, $CO_2$ is not only absorbed in the liquid, but also reacts chemically with the amine in the liquid. Notably, it may be advantageous to remove $H_2S$ in a separate cleaning step prior to chemical scrubbing.

In each of the above described absorption techniques the regeneration of the liquid may also provide a $CO_2$ rich tail gas, which is separate from the $CH_4$-rich product stream. In one embodiment, a tail gas comprising $CO_2$ removed from the biogas is provided by stripping out the $CO_2$, and possibly $H_2S$ if present, from the wash water of the process.

In one embodiment, the separation system 125 includes a water scrubber. For example, in one embodiment, the biogas is compressed and then fed to a scrubbing tower where it is contacted with water. In this embodiment, the $CO_2$, $H_2S$, and/or siloxanes may be preferentially absorbed by the water. The upgraded biogas exits from the top of the scrubbing tower. The absorbed $CO_2$ may be recovered in a separate stripping tower. In this embodiment, the separating system 125 includes the compressor, the scrubbing tower, and the stripping tower, whereas the upgrading system 100 includes the separation system 125 and may also include a biogas dehumidifier for drying the upgraded biogas exiting the separation system 125. For example, in one embodiment, the separating system 125 includes a water scrubbing system utilizing Greenlane technology. Since the separating system 125 in this embodiment may remove $CO_2$, $H_2S$, and/or siloxanes, separate $H_2S$ and/or siloxanes cleaning systems may not be required, although may be advantageous for cleaning the tail gas if significant amounts of $H_2S$ and/or siloxanes are also recovered with $CO_2$ in the stripping tower. Optionally, one or more cleaning system configured to remove $N_2$ and/or $O_2$ are provided. For example, in one embodiment, the upgraded biogas collected from the scrubbing tower may be compressed and fed to a $N_2$ removing cleaning system based on pressure swing absorption (PSA).

In this embodiment, the $CH_4$-depleted gas to be enriched may include at least a portion of the recovered $CO_2$ and/or $N_2$.

In one embodiment, the separation system 125 includes an organic physical scrubber. For example, in one embodiment, the biogas is compressed and then fed counter-currently into a packed absorption column containing a solvent selected to selectively absorb $CO_2$. In this embodiment, the biogas is dried prior to entering the separation system 125 (e.g., in one embodiment, the biogas upgrading system 120 includes a biogas dehumidifier disposed upstream of the separation system 125). The upgraded biogas exits from the top of the column, whereas the solvent solution that is rich in $CO_2$ is fed to a flash tank where the solvent is regenerated and the $CO_2$ collected. The solvent may be any liquid that preferentially absorbs $CO_2$. For example, some liquids that may be suitable are methanol (Rectisol™ process), glycol ethers (Selexol™ process), and diethylpropylene glycol (DEPG). In one embodiment, the separation system 125 includes an organic physical scrubbing system utilizing Morrow Renewables technology.

Pressure Swing Adsorption

The principle behind pressure swing adsorption (PSA) is that under pressure, gases tend to be attracted to solid surfaces, or "adsorbed". The higher the pressure, the more gas is adsorbed. When the pressure is reduced, the gas may be released, or "desorbed." In particular, PSA is based on the fact that different gases may be attracted to different solid surfaces more or less strongly, and relies on these different affinities for adsorbent material to separate different gases. For example, PSA often uses an adsorbent material such as activated carbon, carbon molecular sieves, or zeolites. The PSA process works by "swinging" the total pressure of the system between a high pressure (e.g., in feed mode, wherein gas is adsorbed), and a low pressure (e.g., in regeneration mode, wherein adsorbent material is regenerated). In biogas upgrading systems, the adsorbent material may be a porous material (e.g., carbon molecular sieves, activated carbon, or zeolites) that preferentially adsorbs one component of biogas over another. In one embodiment, the adsorbent material preferentially adsorbs $CO_2$ to provide a $CH_4$-rich stream. In one embodiment, the adsorbent material preferentially adsorbs $N_2$ to provide a $CH_4$-rich stream. In one embodiment, the adsorbent material preferentially adsorbs $CH_4$ to provide the $CH_4$-rich stream. In one embodiment, the adsorbent material preferentially adsorbs more than one component to provide the $CH_4$-rich stream.

Figure 2A:
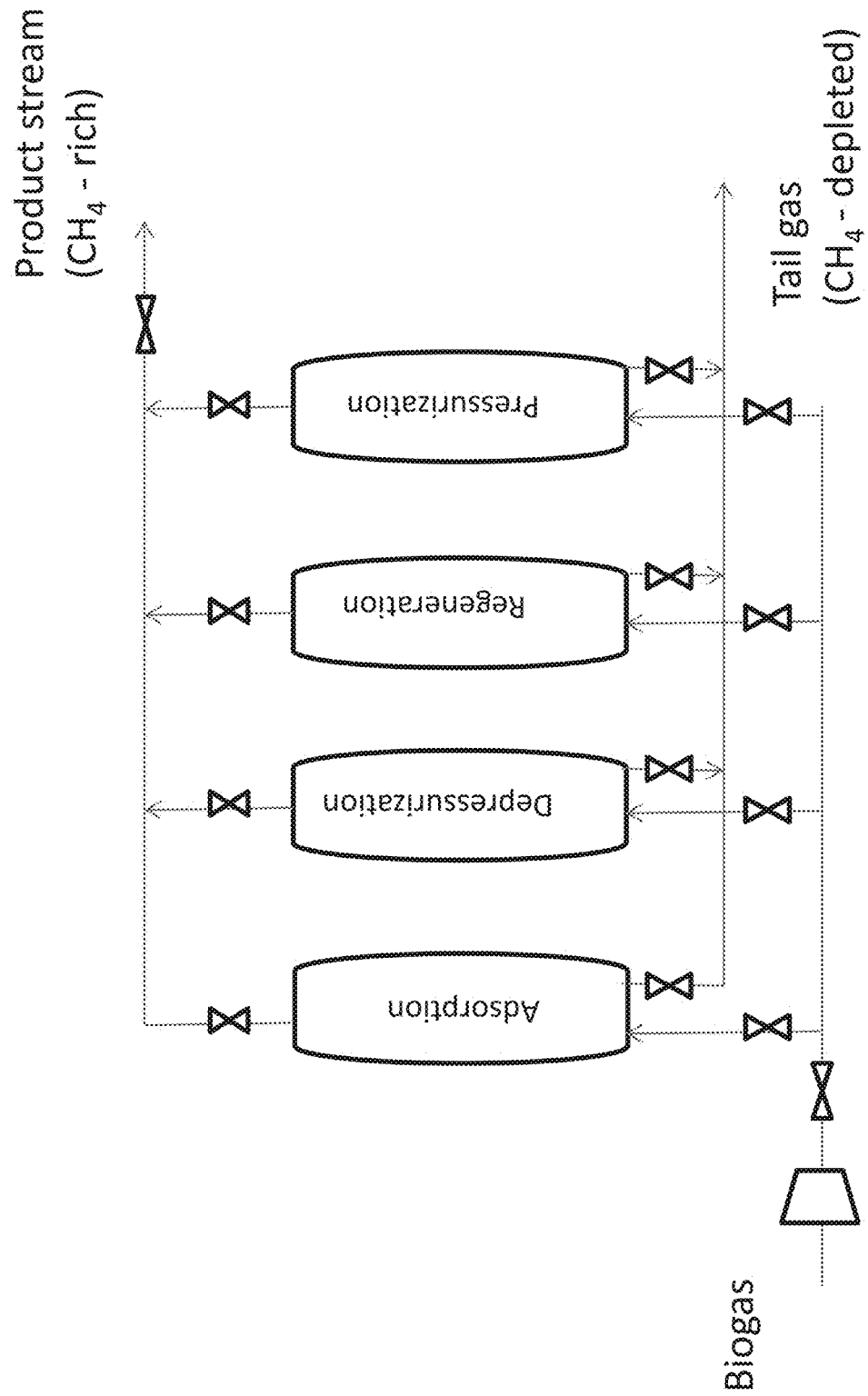
FIG. 2a is a schematic diagram showing an embodiment of a separating system for providing upgraded biogas based on pressure swing adsorption (PSA), which may be used in the system illustrated in FIG. 1b.

In one embodiment, the separating system 125 includes a PSA system. In operation, biogas is fed under pressure to a first vessel containing a bed of adsorbent material. The adsorbent material, which may be carbon molecular sieves, activated carbon, or zeolite, attracts the $CO_2$ more strongly than it does $CH_4$. As the stream of biogas is passed over the bed, part or all of the $CO_2$ remains in the bed, while the gas stream exiting the vessel is $CH_4$-rich (e.g., may contain more than 97% $CH_4$). When the bed reaches the end of its capacity to adsorb $CO_2$, it may be regenerated by reducing the pressure and releasing the adsorbed $CO_2$. In one embodiment, when the adsorbent bed needs to be regenerated, the biogas flow is diverted to another vessel in which the adsorbing material has already been regenerated. For example, up to 4, 6, or 9 separating vessels may be arranged in parallel, with each vessel working on a different phase of the process (e.g., adsorption, depressurization, regeneration, and pressure build-up) in order to achieve continuous or near continuous operation. For example, as shown in FIG. 2a, one vessel may work on adsorption, one vessel may work on depressurization, one vessel may work on regeneration, and one vessel may work on pressure build-up.

During adsorption, $CO_2$ is adsorbed while the $CH_4$ passes through the vessel. Depressurization may be achieved by equalizing with a second pressurizing vessel. Regeneration may be achieved at atmospheric pressure or vacuum. In other words, regeneration may be accomplished by a stepwise depressurization of the vessel (e.g., the pressure balance with an already regenerated vessel, followed by a second depressurization step to about atmospheric pressure or vacuum). The second depressurization step, which may be referred to as blowdown, may be part of the regeneration stage. Additionally, or alternatively, regeneration may include back-flushing the bed to desorb and/or purge the adsorbed gases (i.e., a purging step). Pressure build-up may be achieved by equilibrating pressure with a vessel that is at the depressurization stage.

The $CH_4$-rich stream exiting each vessel may be fed to a first outlet of the PSA system as upgraded biogas (e.g., RNG). The $CO_2$-rich exhaust gas exiting each vessel (e.g., which may be obtained from the first depressurization, the second depressurization, and/or the purge effluent stream) may be fed to a second outlet of the PSA as a tail gas stream. In some embodiments, the $CO_2$-rich exhaust gas exiting each vessel is obtained solely from the purge effluent stream, while the gas from the first and/or second depressurizations is either used to pressurize another vessel and/or fed back to the biogas inlet. For example, since any adsorbed $CH_4$ may be released earlier than adsorbed $CO_2$ (e.g., at higher pressures), while the bulk of the $CO_2$ is desorbed at lower pressures, the exhaust gas from the first depressurization may be backset to the biogas inlet. Exhaust gas from the second depressurization may be fed to a second stage of adsorption and/or exit the system in a tail gas stream.

In one embodiment, the purge stream used to back-flush the bed during regeneration is recycled from the process. For example, the purge stream may be sourced from a $CH_4$-rich stream produced by the PSA process, or may be a stream of biogas. Using a portion of the $CH_4$-rich product stream may be advantageous since this gas does not contain much $CO_2$.

In accordance with one embodiment of the instant invention, regenerating includes providing a purge stream comprising natural gas withdrawn from a distribution system. Advantageously, using natural gas as a purge gas may enrich the tail gas, thereby obviating a separate enriching step and/or reducing the amount of natural gas needed in a separate enriching step. In addition, it may obviate a need to use upgraded biogas as a back flush in the regeneration process.

Advantageously, PSA may also separate other components (e.g., $O_2$ and $N_2$) from the biogas in addition to the $CO_2$. In one embodiment, the separating system 125 includes first and second PSA vessels for removing $CO_2$ and $N_2$, respectively. In one embodiment, the PSA process provides a $CH_4$-rich stream and a tail gas stream, wherein the tail gas stream includes $CO_2$, $O_2$, and/or $N_2$. The tail gas stream may also contain some $CH_4$. However, since the adsorption material may adsorb $H_2S$ irreversibly, and thus may be poisoned by $H_2S$, it may be advantageous to clean the biogas by removing $H_2S$ and water prior to feeding the biogas to the PSA system. Notably, PSA can provide various levels of upgraded biogas. For example, PSA may provide more than 97% $CH_4$ enrichment and thus may be used to produce RNG.

In one embodiment, the separation system 125 includes a PSA system. For example, in one embodiment, the biogas is compressed and fed to a PSA system having at least one column packed with a material that selectively adsorbs $CO_2$. In one embodiment, the PSA system is a continuous multi-column PSA system.

In one embodiment, the separating system 125 includes a PSA system utilizing Xebec technology (e.g., BGX solutions). BGX solutions, which is based on the company's hydrogen product platform but is modified to remove $CO_2$ from low quality methane streams, may produce pipeline quality RNG utilizing a 6 bed or 9 bed PSA cycle system and/or a system that is fully skid-mounted. A reported advantage of BGX solutions is that the multi-column PSA system may substantially remove $CO_2$, $N_2$, $O_2$, $H_2O$, and $H_2S$ from the biogas, providing RNG having at least 96% methane and an off-gas containing $CO_2$, $N_2$, $O_2$, $H_2O$, and/or $H_2S$. Accordingly, separate $N_2$, $O_2$, and $H_2O$ removing systems may not be required to provide the upgraded biogas, although a separate $H_2S$ and/or $H_2O$ removal system may be provided for precleaning the biogas, for cleaning the tail gas, and/or for cleaning the enriched tail gas. In one embodiment, the biogas upgrading system 120 may include a siloxane removal system, a $H_2S$ removal system, and/or a $H_2O$ removal system in addition to the separating system 125. Each of the optional siloxane removal system, $H_2S$ removal system, and $H_2O$ removal system, may be disposed upstream of the separating system 125 and/or downstream of the separating system 125 (e.g., for the tail gas stream). Providing these optional siloxane, $H_2S$, and/or $H_2O$ cleaning systems may protect the combustion system 140 when the enriched tail gas (e.g., which is obtained and/or derived from the off-gas containing $CO_2$, $N_2$, $O_2$, $H_2O$, and/or $H_2S$) is combusted.

In one embodiment, the separating system 125 includes a PSA system utilizing Guild technology (e.g., Molecular Gate™). For example, in one embodiment, the separating system 125 includes at least one adsorption vessel (e.g., packed with titanium silicate molecular sieves), a single-stage vacuum pump for regeneration, a valve and piping skid network, and a controller for controlling the flow between and to vessels. Advantageously, this system may substantially remove both $CO_2$ and $N_2$ from the biogas. In this embodiment, the upgrading system 120 may also include a siloxane removal system, a $H_2S$ removal system, and/or a $H_2O$ removal system in addition to the separating system 125. Providing the optional siloxane, $H_2S$, and/or $H_2O$ cleaning systems upstream of the separating system 125 may advantageously remove compounds that could negatively affect the adsorbent and/or may provide a relatively clean enriched tail gas (e.g., containing primarily $CO_2$, $N_2$, and/or fossil-based methane).

In one embodiment, the separating system 125 includes a PSA system utilizing Adsorption Research Inc. (ARI) technology. A reported advantage of ARI technology is that the corresponding PSA system may substantially remove $CO_2$, $N_2$, $O_2$, $H_2O$, $H_2S$, VOCs, and siloxanes from the biogas, providing RNG that meets pipeline standards and an off-gas containing $CO_2$, $N_2$, $O_2$, $H_2O$, VOCs, siloxanes, and/or $H_2S$. In this embodiment, separate $H_2S$, $N_2$, $O_2$, and $H_2O$, and $H_2S$ removing systems may not be required to provide the upgraded biogas, however it may be advantageous to provide $H_2S$, $H_2O$, and $H_2S$ removal systems for cleaning the tail gas and/or enriched tail gas. In one embodiment, the biogas upgrading system 120 may include a siloxane removal system, a $H_2S$ removal system, a VOCs removal system, and/or a $H_2O$ removal system in addition to the separating system 125. Each of the optional cleaning systems, may be disposed upstream of the separating system 125 and/or downstream of the separating system 125 (e.g., for the tail gas stream). Providing these optional cleaning systems may protect the combustion system 140 from $H_2O$, VOCs, siloxanes, and/or $H_2S$ when the enriched tail gas (e.g., which is obtained and/or derived from the off-gas) is combusted. For example, in one embodiment, the separating system 125 is based on a 2-stage Advansorb™-LFG process technology. In one embodiment, the separating system 125 includes at least one adsorption vessel, means for regeneration, a valve and piping network, and a controller for controlling the flow between and to vessels.

Figure 2B:
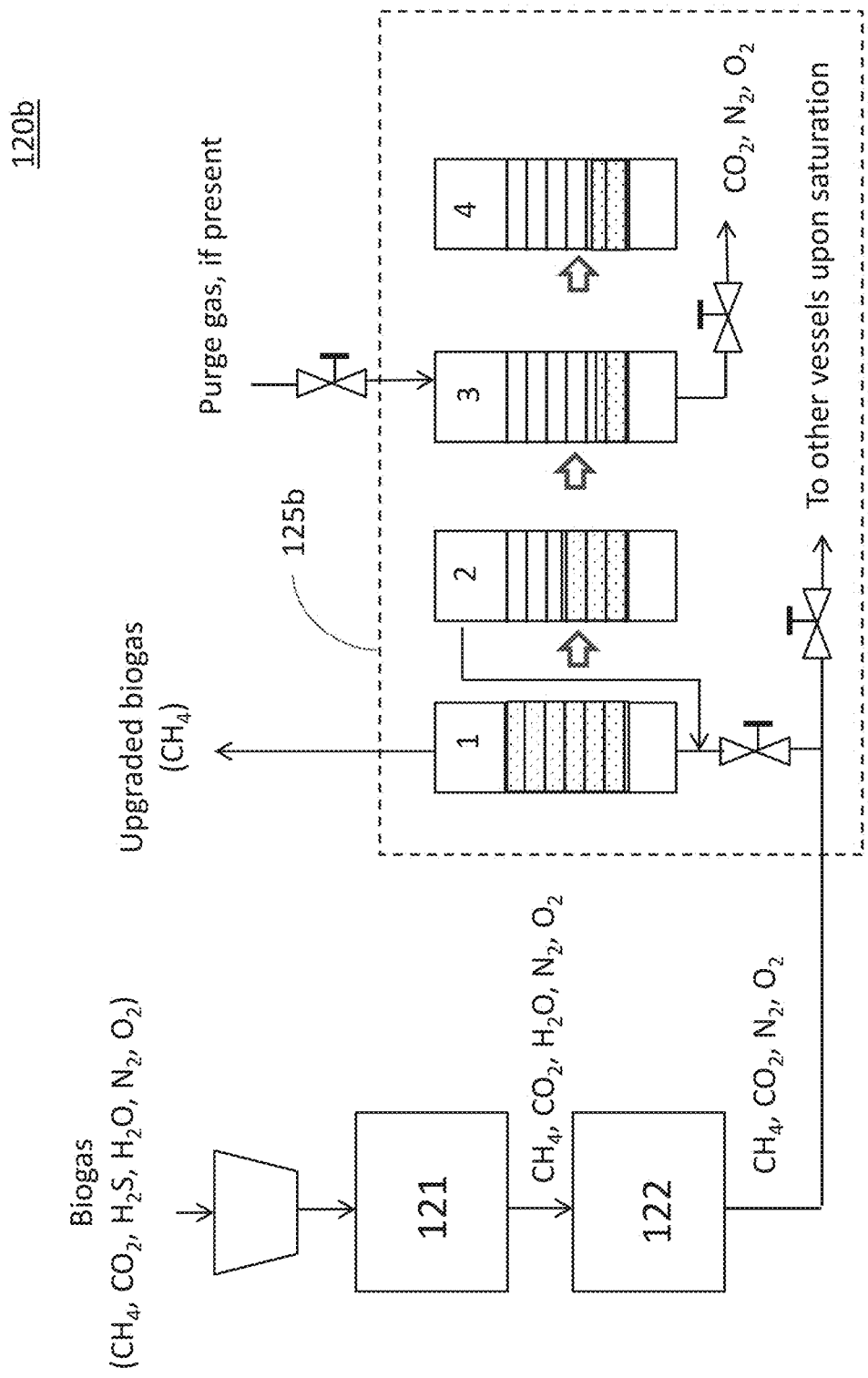
FIG. 2b is a schematic diagram showing a biogas upgrading system based on PSA, in accordance with one embodiment of the invention.

Referring to FIG. 2b, there is shown a biogas upgrading system 120b in accordance with one embodiment. In this embodiment, the biogas upgrading system 120b includes a compressor, a $H_2S$ removal system 121, a $H_2O$ removal system 122, and a separating system 125b (i.e., that is PSA-based). Optionally, the $H_2S$ removal system 121 also removes siloxanes and/or the biogas upgrading system also includes a siloxane removal system (not shown). In the embodiment illustrated in FIG. 2b, the $H_2S$ removing system 121 is disposed upstream of the $H_2O$ removal system 122, however, in another embodiment, this order is reversed. Providing the $H_2S$ removal system 121 and a $H_2O$ removal system 122 upstream of the separating system 125b advantageously may protect the separation equipment (e.g., adsorbent, valves, and/or vessels from $H_2S$ and/or $H_2O$). Some examples of suitable $H_2S$ removal systems and/or $H_2O$ removal systems are discussed above.

In this embodiment, the PSA-separating system is a multi-bed system that provides a continuous operation and that is based on the Skarstrom cycle. In particular, the separating system 125 includes four vessels (e.g., labeled 1-4) connected through a network of pipes and valves. For illustrative purposes the first vessel is depicted being in the adsorption phase (e.g., P=700-800 kPa), the second vessel is depicted being in the depressurization phase (e.g., P=100 kPa), the third vessel is depicted being in the regeneration phase (e.g., P~0 kPa), and the fourth vessel is depicted being in the pressurization phase. In the adsorption phase, $CO_2$, $N_2$, and/or $O_2$ in the biogas (e.g., and in the recycled stream from depressurization) is preferentially adsorbed on the adsorbent providing a stream of upgraded biogas (e.g., RNG). In the regeneration phase, the $CO_2$, $N_2$, and/or $O_2$ adsorbed during the absorption phase is desorbed. At least a portion of the desorbed $CO_2$, $N_2$, and/or $O_2$ provide a tail gas stream that may be enriched with natural gas. In one embodiment (not shown), the tail gas is enriched by purging the vessel in the regeneration phase with natural gas.

In one embodiment, a $CH_4$ rich stream containing nitrogen is fed to a PSA system that separates $N_2$ and $CH_4$ to provide a $CH_4$ rich stream that is more concentrated (i.e., higher BUT/cf) than the inlet $CH_4$ rich stream. Such PSA nitrogen removal system may preferentially adsorb $CH_4$ or $N_2$.

Membranes

The principle behind membrane separation is based on different molecules having varying permeability through a membrane. More specifically, some molecules, referred to as the permeant(s) or permeate, diffuse across the membrane (e.g., to the permeate side). Other molecules do not pass through the membrane and stay on the retentate side. The driving force behind this process is a difference in partial pressures, wherein the diffusing molecules move from an area of high concentration to an area of low concentration. Different types of membranes are available, each with its particular specifications. Two basic systems exist: (1) gas-gas separation with a gas phase at both sides of the membrane, and (2) gas-liquid absorption separation with a liquid absorbing the diffused molecules.

In one embodiment, the separating system 125 is based on a separation wherein there is a gas phase at both sides of the membrane. In this embodiment, the membrane is selected such that the $CO_2$ preferentially passes through the micropores of the membrane, while the $CH_4$ is concentrated on the retentate side. For example, in one embodiment, the membrane is formed from a polymeric material (e.g., polyimide, polysulfone, or polydimethylsiloxane) that preferentially passes polar molecules such as $CO_2$. In these systems, water vapour and $NH_3$, and to some extent $H_2S$ and $O_2$, may also diffuse across the membrane. Limited removal of $N_2$ may also be provided. In some embodiments, it may be advantageous to clean the biogas to remove water, $H_2S$, and/or siloxanes, prior to membrane separation. In one embodiment, the membrane material comprises cellulose acetate.

Figure 3A:
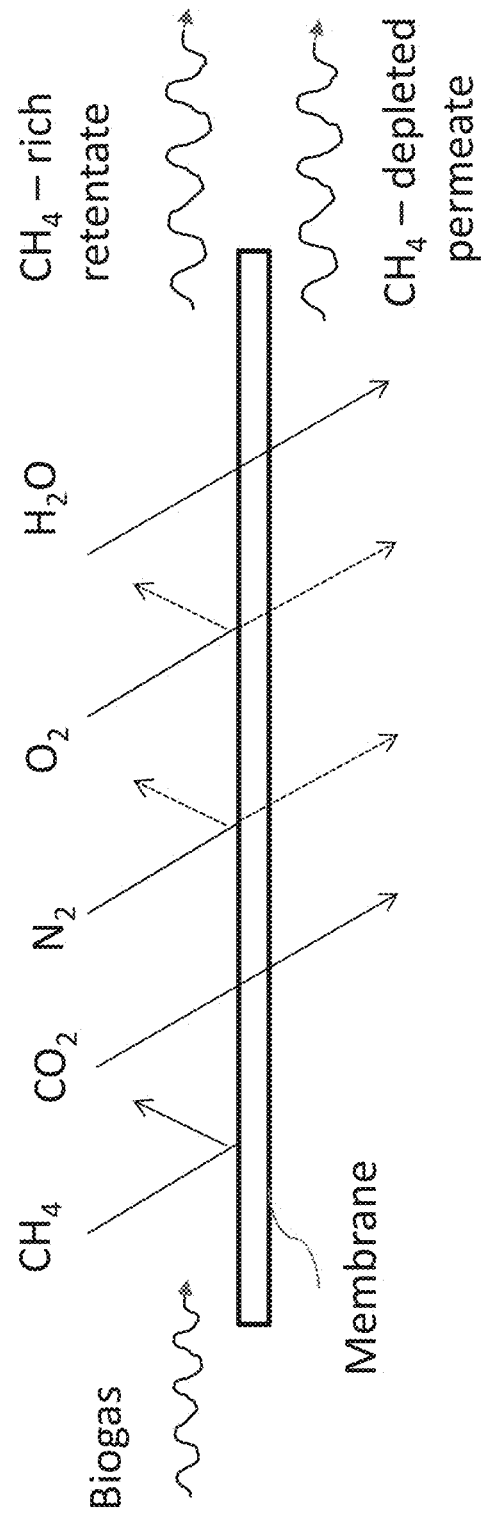
FIG. 3a is a schematic diagram showing an embodiment of a separating system for providing upgraded biogas based on membrane permeation, which may be used in the system illustrated in FIG. 1b.

FIG. 3a illustrates how a stream of biogas containing $CH_4$, $CO_2$, $N_2$, $O_2$, and water vapour may be provided on one side of a membrane (e.g., at high pressure) such that $CO_2$ and water vapour may be removed from the stream of biogas through the membrane, with partial removal of $N_2$ and $O_2$.

In general, the membrane and/or membrane module may use any suitable membrane configuration (e.g., flat, hollow fiber, spiral wound, tubular, etc.). In one embodiment, the membrane is constructed as a flat membrane as illustrated in FIG. 3a. In one embodiment, the membrane is constructed as a hollow fiber membrane. When the membrane is a hollow fiber membrane, the retentate side may correspond to the inside of the hollow fiber, while the permeate side corresponds to the exterior of the hollow fiber. In one embodiment, the separating system 125 comprises a membrane module including multiple hollow fibers (e.g., several thousand). In one embodiment, the separating system 125 comprises a membrane module including one or more spiral wound membrane elements.

Figure 3B:
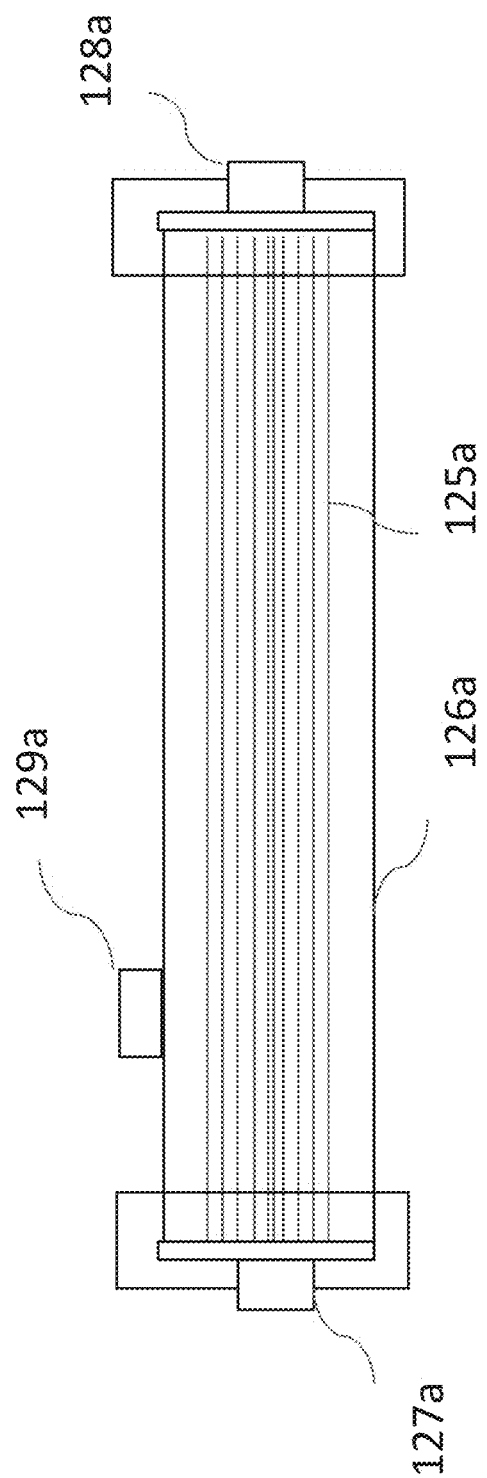
FIG. 3b is a schematic diagram showing another embodiment of a separating system for providing upgraded biogas based on membrane permeation, which may be used in the system illustrated in FIG. 1b.

For example, referring to FIG. 3b, there is shown an embodiment of a module wherein a plurality of hollow fibers 125a is secured within a casing 126a. A first end of the casing 126a is provided with a biogas inlet 127a, whereas the other end is provided with a retentate (e.g., $CH_4$-rich) outlet 128a. The fibers are secured within the ends of the casing such that biogas introduced into the inlet is forced along the plurality of tubes (e.g., on the inside). The permeate (e.g., $CO_2$-rich) that diffuses through the tubes, exits out outlet 129a of the casing, whereas the retentate (e.g., $CH_4$-rich) that propagates along the tubes exits out the outlet 128a disposed on the other end of the casing.

Since the driving force for the diffusion of $CO_2$ through the membrane is the difference of the partial pressures of $CO_2$ in the feed and on the permeate side, the transmembrane flow may be increased by increasing the pressure in the biogas feed stream (i.e., on the retentate side). In one embodiment, pressure is applied by compressing the raw biogas. For example, in one embodiment the operating pressure is between about 87 and about 290 psi (e.g., between about 6 and about 20 bar). In addition, or alternatively, the partial pressure on the permeate side may be reduced by providing a sweep stream of relatively inert gas that removes the diffused $CO_2$ from the vicinity of the membrane. For example, $N_2$ has been proposed as a sweep gas. The sweep gas may be provided in a cross-flow or counter-flow configuration. In either case, the sweep gas may be fed into a port on the casing (not shown) so as to improve the permeation of $CO_2$, which exits from an outlet of the membrane separation system as tail gas. In addition to the sweep gas and the $CO_2$ that diffused through the membrane, the tail gas may include some $O_2$, $N_2$, and/or $CH_4$ depending on the membrane used and its selectivity.

In general, membrane separation may provide a reasonably high quality $CH_4$-rich product stream by using a membrane having high selectivity and sufficient membrane area, and/or by using suitable operational parameters. Improved separation may be achieved by applying multiple stages (e.g., two or three), in tandem, with recycle. Notably, membrane separation can provide various levels of upgraded biogas. For example, membrane separation may provide more than 98% $CH_4$ enrichment and thus may be used to produce RNG. Advantageously, the relatively high pressure of the retentate may allow direct injection of the RNG into the DS without further compression.

In general, the biogas fed to the separating system 125 may be at a pressure higher than atmospheric (e.g., will have passed through a compressor). In one embodiment, the separation system 125 uses high pressure gas membranes. In one embodiment, the separating system 125 uses low pressure gas membranes. In one embodiment, the separating system 125 uses commercially available low pressure hollow fiber counter-current membrane modules. Using lower pressure gas membranes may reduce power consumption. In one embodiment, wherein the separating system 125 includes a polymeric hollow fiber membrane, the biogas fed to the separating system is at about 200 PSIG, the upgraded biogas is at about 150 PSIG, and the permeate gas is at about 4 PSIG.

In one embodiment, the separation system 125 includes a hollow fiber membrane system having a high $CO_2/CH_4$ selectivity. In one embodiment, the separation system 125 includes a SEPURAN™ Green membrane system.

In one embodiment, the separation system 125 includes a plurality of hollow fiber polymer membrane modules having a high $CO_2/CH_4$ selectivity. For example, in one embodiment, the separation system 125 is based on Air Liquide membrane technology for upgrading biogas to RNG. In this embodiment, the plurality of hollow fiber polymer membrane modules may be arranged in parallel and/or in series (i.e., a cascade of membrane modules). In one embodiment, capacity is increased or decreased by adjusting the number of membrane modules arranged in parallel. In one embodiment, purity is increased or decreased by adjusting the number of membrane modules arranged in series (e.g., arranged in a single stage or multi-stage configuration). Advantageously, Air Liquide membrane modules may remove $CO_2$, $O_2$, $H_2O$ and $H_2S$ from the biogas, thus providing upgraded biogas having a methane content between about 80% and 99% (e.g., depending on whether $N_2$ was originally present in the biogas). In one embodiment, the separation system 125 includes an Air Products (e.g., PRISM™) membrane system.

Figure 3C:
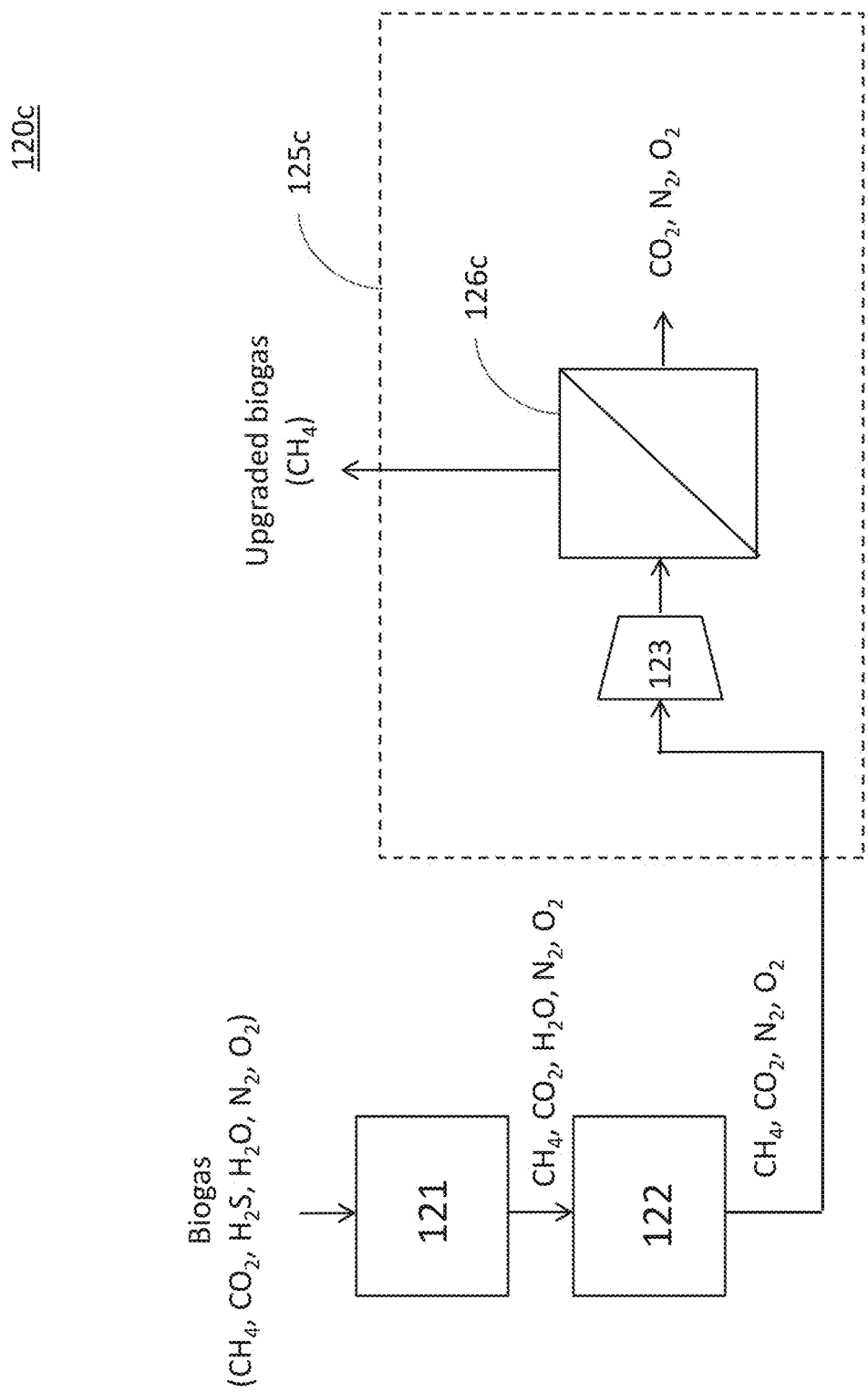
FIG. 3c is a schematic diagram showing a biogas upgrading system, wherein the separation is provided by a single stage membrane system, in accordance with one embodiment of the invention.

Referring to FIG. 3c, there is shown a biogas upgrading system 120c in accordance with one embodiment. In this embodiment, the biogas upgrading system 120c includes a $H_2S$ removal system 121, a $H_2O$ removal system 122, and the separating system 125c (i.e., which membrane based). Optionally, the $H_2S$ removal system 121 also removes siloxanes and/or the biogas upgrading system also includes a siloxane removal system (not shown). In the embodiment illustrated in FIG. 3c, the $H_2S$ removing system 121 is disposed upstream of the $H_2O$ removal system 122, however, in another embodiment, this order is reversed. Providing the $H_2S$ removal system 121 and a $H_2O$ removal system 122 upstream of the separating system 125c advantageously may protect the separation equipment (e.g., membrane(s))

and/or the combustion equipment (not shown). Some examples of suitable H$_2$S removal systems and/or H$_2$O removal systems are discussed above.

In this embodiment, the separating system 125c is a single stage membrane system. In particular, the separating system 125c includes a compressor 123 for compressing the cleaned biogas (e.g., between 6 bar and 20 bar), a membrane unit 126c (e.g., one or more membrane modules, which may be arranged in parallel and/or in series), and a control unit (not shown) for controlling the flow of gas. In one embodiment, the biogas upgrading system 120c also includes filters, heat exchangers, coolers, and/or gas analyzers (not shown). For example coolers may be provided for adjusting the temperature of the compressed gas prior to the gas being fed to the membrane unit 126c. In this embodiment, each of the one or more membrane modules may include thousands of tiny hollow fibers that allow gas molecules such as CO$_2$, N$_2$, O$_2$, and/or H$_2$O to diffuse through the membrane walls, while the CH$_4$ molecules are transported the length of the tubes and exit from the end of the module.

Figure 3D:
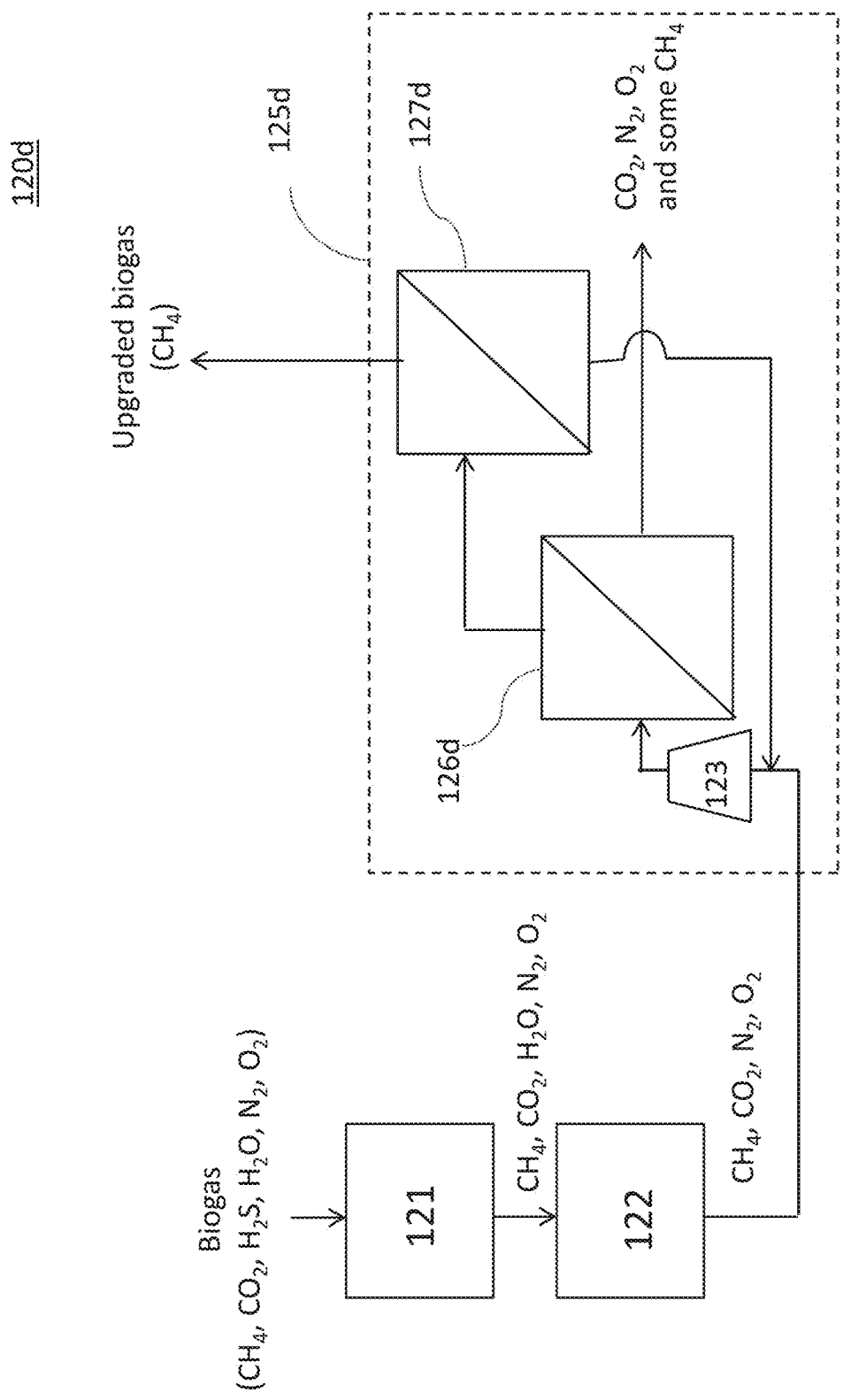
FIG. 3d is a schematic diagram showing a biogas upgrading system, wherein the separation is provided by two stage membrane system, in accordance with one embodiment of the invention.

Referring to FIG. 3d, there is shown a biogas upgrading system 120d in accordance with one embodiment. In this embodiment, the biogas upgrading system 120d includes a H$_2$S removal system 121, a H$_2$O removal system 122, compressor 123, and the separating system 125d (i.e., that is membrane based). Optionally, the H$_2$S removal system 121 also removes siloxanes and/or the biogas upgrading system also includes a siloxane removal system (not shown). In the embodiment illustrated in FIG. 3d, the H$_2$S removing system 121 is disposed upstream of the H$_2$O removal system 122, however, in another embodiment, this order is reversed. Providing the H$_2$S removal system 121 and a H$_2$O removal system 122 upstream of the separating system 125d advantageously may protect the separation equipment (e.g., membrane(s)) and/or the combustion equipment (not shown). Some examples of suitable H$_2$S removal systems and/or H$_2$O removal systems are discussed above.

In this embodiment, the separating system 125d is a two stage membrane system, wherein two membrane units are arranged in series and wherein the permeate from the second unit is recycled back to the first unit. In particular, the separating system 125d includes a first membrane unit 126d (e.g., one or more membrane modules, which may be arranged in parallel and/or in series), a second membrane unit 127d (e.g., one or more membrane modules, which may be arranged in parallel and/or in series), a compressor for compressing the cleaned biogas and the recycled permeate of the second membrane unit 127d (e.g., between 6 bar and 20 bar), and a control unit (not shown) for controlling the flow of gas. In one embodiment, the biogas upgrading system 120d also includes filters, heat exchangers, coolers, and/or gas analyzers (not shown). For example, coolers may be provided for adjusting the temperature of compressed gas. In this embodiment, each of the one or more membrane modules may include thousands of tiny hollow fibers that allow gas molecules such as CO$_2$, N$_2$, O$_2$ and/or H$_2$O to diffuse through the membrane walls, while the CH$_4$ molecules are transported the length of the tubes and exit from the end of the module.

In operation, biogas fed into the biogas upgrading system is subject to H$_2$S and/or siloxane removal, is subject to water removal, is compressed, and is fed to the first membrane unit 126d. The first membrane unit 126d provides a CH$_4$-rich retentate (e.g., containing more CH$_4$ than the gas input into the unit 126d (percentage wise), but also containing some CO$_2$, N$_2$, and/or O$_2$), and a CH$_4$-depleted permeate (e.g., containing less CH$_4$ than the gas input into the unit 126 (percentage wise)). The CH$_4$-depleted permeate may include CO$_2$, N$_2$, O$_2$, and/or CH$_4$. The retentate of the first membrane unit 126d is fed into the second membrane unit 127d. The second membrane unit 127d removes additional CO$_2$, N$_2$, and/or O$_2$. The retentate of the second membrane 127d provides a relatively high purity upgraded biogas stream. The permeate from the second membrane unit 127d is recycled back to be input into the first membrane unit 126d. In this embodiment, the permeate from the first membrane unit 126d is used to provide the tail gas to be enriched with natural gas. Advantageously, providing a two-stage membrane system may improve the separation and/or increase methane recovery from the biogas, while using relatively inexpensive membranes.

In the embodiment illustrated in FIG. 3d, the first and second membranes units are provided as an asymmetric cascade (i.e., the feed of the $2^{nd}$ stage is the retentate of the $1^{st}$ stage and the permeate flow of the $2^{nd}$ stage is recycled). In another embodiment (not shown), the first and second membrane units are provided as a symmetric cascade (e.g., where the feed of the $2^{nd}$ stage is the permeate stream of the $1^{st}$ stage and the retentate of the $2^{nd}$ stage is recycled).

In the embodiments discussed with reference to FIGS. 3c and 3d, the H$_2$S removal system 121 and the H$_2$O removal system 122 are part of a pre-cleaning system. As discussed above, the order of the H$_2$S removal system 121 and the H$_2$O removal system 122 may be reversed. Alternatively, the functions of H$_2$S removal system 121 and the H$_2$O removal system 122 may be integrated within a same system. In one embodiment, the pre-cleaning system includes a knockout pot for removing H$_2$O, a small PSA for removing H$_2$S, and a polishing filter (e.g., based on activated carbon) for removing VOCs.

Figure 3E:
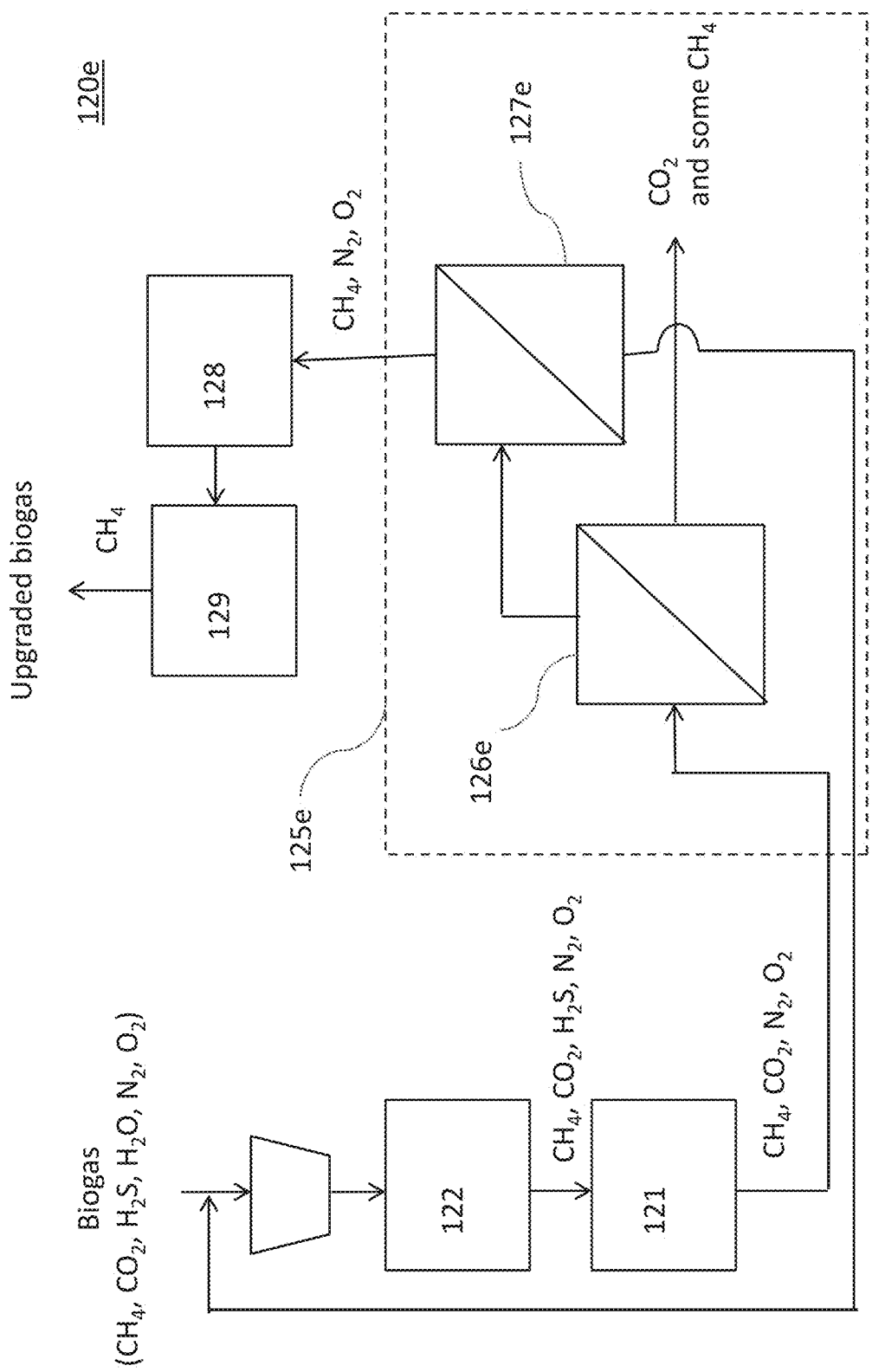
FIG. 3e is a schematic diagram showing a biogas upgrading system, wherein the separation is provided by a two stage membrane system, in accordance with another embodiment of the invention.

In the embodiments discussed with reference to FIGS. 3c and 3d, the membranes were designed to remove CO$_2$, N$_2$, and/or O$_2$. However, in some cases, the membranes may not provide adequate N$_2$ and/or O$_2$ removal (e.g., the upgraded biogas may not meet pipeline standards due to the amount of N$_2$ and/or O$_2$ present). In this case, N$_2$, and/or O$_2$ cleaning systems may be provided to improve the purity of the upgraded biogas. For example, in one embodiment, the upgraded biogas is injected into the distribution system 170 after a post cleaning process. Referring to FIG. 3e, there is shown a biogas upgrading system 120e having N$_2$ and O$_2$ cleaning systems, in accordance with one embodiment. In this embodiment, the biogas upgrading system 120e includes a compressor, a H$_2$O removal system 122, a H$_2$S removal system 121, and the separating system 125e (i.e., that is membrane based). Optionally, the H$_2$S removal system 121 also removes siloxanes and/or the biogas upgrading system also includes a siloxane removal system (not shown). Some examples of suitable H$_2$S removal systems and/or H$_2$O removal systems are discussed above.

In this embodiment, the separating system 125e is a two stage membrane system, wherein two membrane units are arranged in series and wherein the permeate from the second unit is recycled back so that it may be input into the first unit. In particular, the separating system 125e includes a first membrane unit 126e (e.g., one or more membrane modules, which may be arranged in parallel and/or in series), a second membrane unit 127e (e.g., one or more membrane modules, which may be arranged in parallel and/or in series), and a control unit (not shown) for controlling the flow of gas. In this embodiment, the biogas upgrading system also includes a N$_2$ removal system 128 (e.g., a PSA system for removing N$_2$) and a O$_2$ removal system 129 (e.g., a catalytic oxidation system). In one embodiment, the biogas upgrading system 120e also includes filters, heat exchangers, coolers, and/or gas analyzers (not shown). For example, coolers may be provided for adjusting the temperature of compressed gas. Optionally, the nitrogen removed in $N_2$ removal system 128 is fed to the tail gas and/or enriched tail gas.

In one embodiment, a system for providing upgraded biogas is provided that includes the biogas upgrading system 120e, without the $O_2$ removal system 129.

In general, each of the $H_2S$, $H_2O$, $N_2$, $O_2$, VOCs, and siloxane removal systems discussed above may be selected in dependence with the $CH_4/CO_2$ separation technology, the source of the biogas, the contaminants in the biogas, the desired purity, the capacity of the system, and other cleaning systems present, as would be understood by a person skilled in the art. For example, if a pre-cleaning system based on iron-based adsorbents is provided (e.g., which removes $H_2S$ and $O_2$), a separate $O_2$ removal system may not be required. In one embodiment, the separating system 125 and/or biogas upgrading system 120 is a membrane system including a plurality of membrane modules, each of which is configured to remove a different component from the biogas (e.g., at least one membrane module for removing $CO_2$, at least one membrane module for removing $H_2O$, etc). In one embodiment, the separating system 125 and/or biogas upgrading system 120 is a membrane system including at least one membrane module configured to remove a plurality of different components from the biogas (e.g., a silicone membrane module for removing $CO_2$ and siloxanes).

In the embodiments discussed with reference to FIGS. 3d and 3e, the degree of separation (e.g., measured as the percentage of $CO_2$ removed from the biogas relative to what was originally present in the biogas) and/or methane recovery (e.g., the percentage of $CH_4$ recovered from the biogas relative to what was originally present in biogas) was improved by providing a two stage system.

In general, for a given membrane separation unit, the degree of separation in the final product (e.g., how much $CO_2$ is removed from the biogas) may be related to how much of the feed $CH_4$ is recovered. In particular, in these types of membranes, there is often a trade-off between selectivity and permeation flux. For example, if the membrane system is selected and/or configured to provide sufficient separation to provide the upgraded biogas with a methane content that is greater than 98%, then a lower methane yield may be result.

Table 1 demonstrates the relationship between the degree of separation and methane yield for a single stage membrane system with no sweep gas, a two stage membrane system with no sweep gas, and a single stage membrane system using a sweep gas. The data is based on a modeled membrane system wherein the biogas contains only $CH_4$ and $CO_2$ (e.g., in a 50/50 ratio), the pressure ratio is 10:1, and wherein the membrane(s) has/have a permaselectivity $CO_2/CH_4=65$.

TABLE 1

Methane lost to the tail gas as a function of $CO_2$ removed

| | Biomethane Loss to Tail Gas | | |
|---|---|---|---|
| $CO_2$ Removed | Single stage, no sweep | Two stage, no sweep | Single stage, with sweep |
| 98% | 18% | 3% | 7% |
| 95% | 7.5% | 2% | 4% |

TABLE 2

Relative membrane required for various configurations

| | Single stage, no sweep | Two stage, no sweep | Single stage, with sweep |
|---|---|---|---|
| Relative membrane required (area) | 100% | 110% | 43% |

Referring to the second column of Table 1, for a single stage membrane system without sweep, modeling has suggested the following. If the system is configured to produce a product wherein about 98% of the $CO_2$ (vol %) has been removed, then about 18% of the methane (vol %) will be lost in the tail gas. If the system is configured to produce a product wherein about 95% of the $CO_2$ (vol %) has been removed, then about 7.5% of the methane (vol %) will be lost in the tail gas. The amount of $CO_2$ removed may be dependent, for example, on the membrane area.

Referring to the third column of Table 1, it is clear that providing a two stage system, wherein the permeate from the second stage is recycled to the first stage, may improve the degree of separation and/or increase the amount of methane recovered. For example, the two stage system, with no sweep, is able to provide a higher $CH_4$ recovery for the same degree of separation. However, in general, multiple stage systems may result in trade-offs between higher product recovery and increased equipment and/or operating costs. Alternatively, or additionally, the degree of separation and/or methane recovery may be increased by using a sweep gas, as discussed above. The sweep gas improves the separation by reducing the partial pressure of the permeate in the vicinity of the membrane, thus driving the process so that more permeate is produced. The terms "two-stage membrane system", "three-stage membrane system", or "multi-stage membrane system" refer to membrane systems comprising 2, 3, or multiple membrane modules or groups of modules, respectively, cascaded with recycle. The term "single-stage membrane system" refers to a single membrane module or multiple membrane modules arranged in series or in parallel without recycle. In multi-stage membrane systems, the number of stages may be limited by compression costs, which may be high. Referring also to the forth column of Table 1, the efficiency related drawbacks of using a single stage membrane system may be at least partially countered by the benefits of eliminating the second stage, including eliminating the permeate recycle and/or corresponding components (e.g., compressor and/or cooler). Moreover, referring to Table 2, modeling has indicated that use of a sweep gas may reduce the membrane area required by over 50%, while maximizing the RNG output.

Figure 3F:
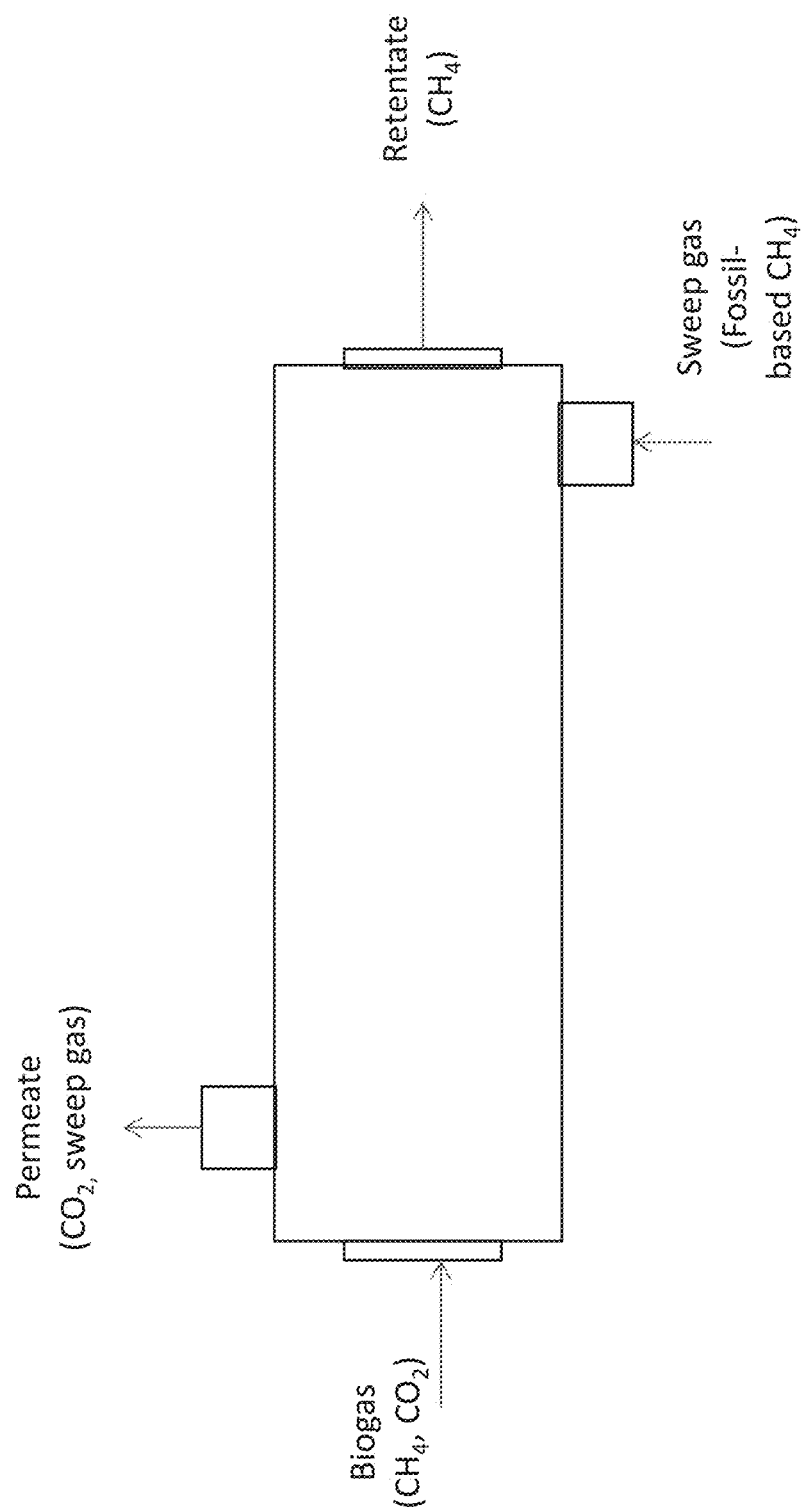
FIG. 3f is a schematic diagram showing a membrane separating system using a sweep gas, which may be used in the system illustrated in FIG. 1b.

For example, referring to FIG. 3f, there is shown an embodiment of a membrane module (e.g., hollow fiber) that separates $CO_2$ and $CH_4$ and that uses a sweep gas. When biogas containing $CO_2$ and $CH_4$ is fed into the membrane module, the permeate (e.g., $CO_2$-rich) that diffuses through the membrane exits out the top, whereas the retentate (e.g., $CH_4$-rich) that propagates along the module exits out the opposite end. The sweep gas purges the $CO_2$ in the permeate away from the membrane, thereby reducing the partial pressure of $CO_2$ on the permeate side of the membrane and increasing transmembrane flow of $CO_2$ fed into the module. Conventionally, sweep gas contains a gas that is different than both the gas to be retained and the gas intended to permeate through the membrane. While any sweep gas may reduce the partial pressure of $CO_2$ on the permeate and thus improve the separation, it can be further advantageous to provide a sweep gas containing methane since this will increase the partial pressure of methane on the permeate side of the module and thus decrease the transmembrane flow of renewable $CH_4$ fed into the module, thereby improving the separation. While the raw biogas and/or upgraded biogas may be used as a sweep gas, this would reduce overall biomethane recovery (i.e., from the biogas). In contrast, using natural gas withdrawn from the DS as a sweep gas may increase biomethane recovery while also providing a methane enriched tail gas. While using a sweep gas may be considered disadvantageous as a result of the increase in cost (e.g., the sweep gas may be an additional component, and is particularly expensive when if it contains natural gas withdrawn from a DS) and/or as a result of increased permeate flow rate, for configurations wherein the sweep gas is used for enriching the tail gas for generating heat and/or electricity, these disadvantages may be overcome.

Figure 4:
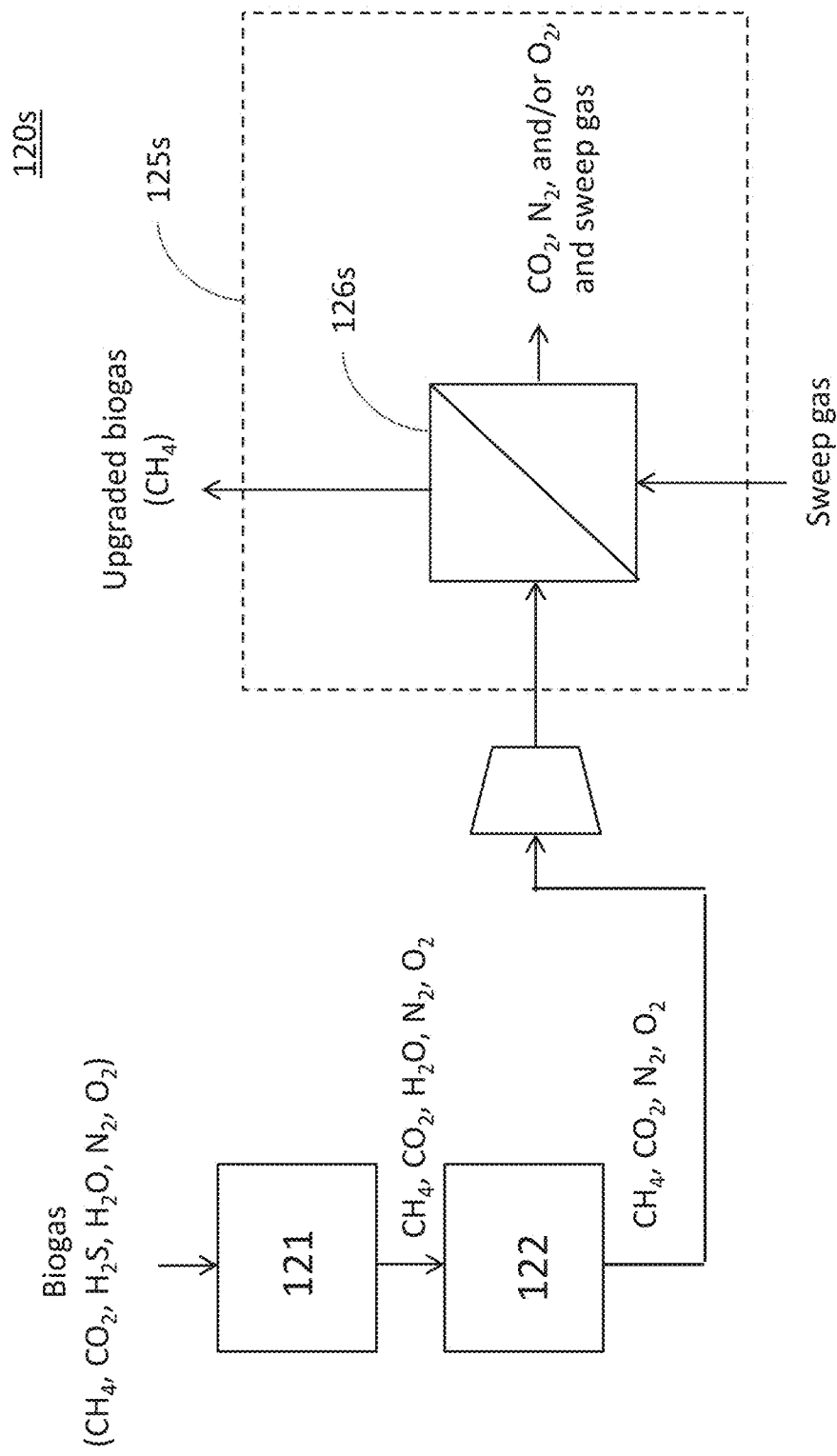
FIG. 4 is a schematic diagram showing a biogas upgrading system, wherein the separation is provided by single stage membrane system utilizing a sweep gas, in accordance with one embodiment of the invention.

Referring to FIG. 4, there is shown an embodiment of the biogas upgrading system 120s, wherein the separating system includes a membrane used with a sweep gas in accordance with one embodiment. In this embodiment, the biogas upgrading system 120s includes a $H_2S$ removal system 121, a $H_2O$ removal system 122, a compressor for compressing the cleaned biogas (e.g., between 6 bar and 20 bar), and the separating system 125s (i.e., that is membrane based). Optionally, the $H_2S$ removal system 121 also removes siloxanes and/or the biogas upgrading system also includes a siloxane removal system (not shown). Some examples of suitable $H_2S$ removal systems and/or $H_2O$ removal systems are discussed above. In one embodiment, the biogas upgrading system 120 also includes filters, heat exchangers, coolers, and/or gas analyzers (not shown). For example, coolers may be provided for adjusting the temperature of the compressed gas prior to the gas being fed to the membrane unit 126s.

In this embodiment, the separating system 125s is a single stage membrane system. In particular, the separating system 125s includes a membrane unit 126s (e.g., one or more membrane modules arranged in parallel and/or in series), and a control unit for controlling the flow of gas (not shown). In this embodiment, each of the one or more membrane modules may include thousands of tiny hollow fibers that allow gas molecules such as $CO_2$, $N_2$, $O_2$, and/or $H_2O$ to diffuse through the membrane walls, while the $CH_4$ molecules are transported the length of the tubes and exit from the end of the module.

The sweep gas may be provided in a counter-flow or cross-flow configuration. In one embodiment, the separating system 125s includes one or more commercially available membrane modules that are designed and/or configured to allow the use of a sweep gas. In one embodiment, the sweep gas is relatively inert (e.g., $N_2$). In one embodiment, the sweep gas is selected to have low permeability across the membrane and/or to increase the heating value of the permeate (e.g., a portion of the upgraded biogas or natural gas). Advantageously, when natural gas is used as a sweep gas it may, at the same time, increase the heating value of the permeate to provide an enriched tail gas.

Cryogenic Upgrading

The principle of cryogenic separation is based on the fact that different gases may have distinct boiling/sublimation points. Biogas upgrading cryogenic separation processes may involve cooling the biogas down to temperatures where the $CO_2$ condenses or sublimates and can be separated as a liquid or a solid fraction, while the $CH_4$ accumulates in the gas phase. For example, in one embodiment the cryogenic biogas separation process operates at low temperatures (e.g., about −100° C.) and at high pressures (e.g., about 40 bar). These operating requirements are maintained by using a series of compressors and heat exchangers. Advantageously, water, $H_2S$, and siloxanes, may also be removed using this process. In fact, cooling may take place in several steps in order to remove the different gases in the biogas individually and to optimize the energy recovery. Accordingly, a tail gas composed primarily of $CO_2$ may be provided.

Cryogenic upgrading systems are known in the art. In one embodiment, the biogas upgrading system 120 and/or separation system 125 includes a Cryo Pur cryogenic biogas upgrading system.

Biogas Upgrading and Tail Gas

With regard to each of the above described biogas upgrading techniques, the separating system based thereon may receive a stream of biogas 15 (which may or may not have been cleaned), and may remove at least some of the $CO_2$ from the stream of biogas 15 to provide upgraded biogas 22 (e.g., a $CH_4$-rich product stream). In many embodiments, the upgraded biogas 22 is of pipeline quality (i.e., is considered to be RNG) and may be injected into the DS without further processing. Optionally, the upgraded biogas 22 is compressed, admixed with propane or other fuel, and/or odorized prior to being injected into the DS 170. For example, in one embodiment, the upgrading system 120 includes at least one compressor for compressing the $CH_4$-rich stream prior to injecting into the DS. The separating system may also produce an exhaust gas that contains at least a portion of the $CO_2$ removed from the biogas.

In one embodiment, the upgrading system 120 discussed with reference to FIG. 1b is a multistage upgrading system that uses a plurality of separating systems, wherein each of the separating systems may be based on a different technology. In this embodiment, the tail gas 24 may include exhaust gases from the multiple separating systems and/or from other systems within the upgrading system 120. In one embodiment, the tail gas 24 includes exhaust gas from one separating system in addition to exhaust gases from other components within the upgrading system 120.

While the separation process ideally separates all of the $CO_2$ from the $CH_4$, in practice, the tail gas 24, which contains $CO_2$ removed during the separation, may also include some $CH_4$ from the biogas, depending on the methane recovery provided by the separation system 125. This is commonly referred to as methane slip. In particular, the term "methane slip", as used herein, refers to the amount of methane that was not fed into the DS, relative to the amount of methane originally in the biogas. As discussed above, the level of methane slip may be dependent on the upgrading technology and/or parameters. For example, methane slip may be lowest for chemical scrubbing (e.g., 0.1-0.2%), followed by cryogenic upgrading (e.g., 0.5%), water scrubbing (e.g., 1-2%), organic physical scrubbing (2-4%), membrane separation (e.g., 0.3-10%), and PSA (e.g., 1-15%).

Since methane is a strong greenhouse gas (e.g., having an approximately 23 times stronger greenhouse gas (GHG) effect than $CO_2$), the GHG emissions for the process and/or resulting fuel may be excessively high if tail gas containing methane is released into the atmosphere. In addition, higher amounts of methane in the tail gas may increase upgrading costs. However, since higher methane recovery also typically increases operating costs, there is a trade-off, and it is common to accept a certain amount of methane in the tail gas. In order to prevent the methane in the tail gas from entering the atmosphere it may be subject to an oxidation (combustion) process (i.e., the $CH_4$ is converted to $CO_2$ by the combustion, and thus does not enter the atmosphere as $CH_4$). Although flaring a methane containing gas may produce $CO_2$, it produces fewer net greenhouse gas emissions than would result from just releasing the methane containing gas into the atmosphere. However, if the tail gas has a methane content that is lower than about 15%, and in particular less than about 10%, it may become increasingly challenging to remove the $CH_4$ from the tail gas economically. In particular, a gas stream having a very low methane content may not contain enough energy to maintain an oxidation (combustion) reaction. Since the tail gas may not contain sufficient $CH_4$ for stable combustion, various approaches for reducing the amount of $CH_4$ released to the atmosphere from tail gas having a relatively low $CH_4$ content have been used and/or proposed. For example, if the tail gas has a sufficiently high methane content it may be flared or fed to a thermal oxidizer. If the tail gas has a relatively low methane content (e.g., if the methane content is less than 10%, and in particular, below about 4%), it may be fed to a device designed to combust low levels $CH_4$ (e.g., a lean-gas burner or may be mixed with biogas, RNG, or natural gas to increase the heating value, and then flared. Alternatively, the tail gas may be mixed with a quantity of biogas or RNG prior to being fed to a biogas CHP. Further alternatively, the purifier or biogas upgrading system may be operated such that there is an intentional increase in the amount of methane released in the tail gas (e an intentional increase in the amount of methane slip).

In instances where the lean tail gas has been admixed with RNG, natural gas, or biogas, the amount of the higher caloric gas traditionally has been selected to be just sufficient to maintain a flame and/or stable operation. For example, a minimal amount of the higher caloric gas may be used to reduce process costs and/or greenhouse gas emissions. The use of natural gas, and in particular large amounts of natural gas, has been generally avoided because it is relatively expensive and/or is not a renewable fuel. In fact, the goal in producing a renewable fuel is generally to reduce greenhouse gas emissions, and thus to avoid excessive use of fossil fuels. The amount of biogas and/or RNG added may depend on how the tail gas is to be combusted and/or how much methane is present the methane content of the tail gas). For example, a conventional combustion engine may require a methane content of at least about 30% (e.g., have a minimum heating value (LHV) of about 300 BTU/a), whereas a microturbine may require a methane content between 30 and 35% (e.g., have a minimum heating value between 300-350 BTU/cf) in order to achieve stable operation. For comparative purposes, a methane content of about 15% (e.g., or a heating value of about 150 BTU/cf) may be required for flaring.

In general, if the methane content of the tail gas is low, it has been considered preferable to combust the tail gas by flare or a lean-gas burner, whereas tail gas having a higher methane content may be combusted to produce heat and/or electricity. The heat generated during the combustion process may be supplied either directly as process heat to the biogas plant (that may have self-heating requirements) or may be transferred to a district heating network. In any case, the use of natural gas in biogas upgrading traditionally has been minimized because it is not a renewable fuel and/or is relatively expensive. It is counter-intuitive to remove $CO_2$ from biogas, only to add natural gas to the $CO_2$, for combustion for heat and/or power. Conventionally, additional purchase of methane is minimized or avoided by configuration of the upgrading system.

Enriching the Tail Gas with Natural Gas

The term "tail gas", as used herein, refers to the gas fed to an outlet of the separating system or upgrading system and that contains at least a portion of the $CO_2$ removed from the biogas by the separation system. In one embodiment, the tail gas 24 is at a lower pressure than the upgraded biogas 22. In one embodiment, the tail gas 24 contains most of, or at least a relatively large portion of, the $CO_2$ from the biogas fed into the biogas upgrading system 120. In one embodiment, the tail gas 24 is composed largely of $CO_2$ (e.g., greater than 75%). In one embodiment, the tail gas 24 also contains some $CH_4$ from the biogas. In one embodiment, the tail gas has a biomethane content between about 0.1 and 35%. In one embodiment, the tail gas 24 also contains $O_2$, $N_2$, $NH_3$, and/or $H_2S$. In one embodiment, the tail gas contains primarily $N_2$ removed from the biogas. In one embodiment, the separation system 125 includes a membrane and the tail gas contains sweep gas. In one embodiment, the separation system 125 includes a PSA system and the tail gas contains purge gas. In one embodiment, the tail gas contains primarily $CO_2$ and $N_2$. In embodiments where the separation system 125 includes a membrane system and/or a PSA system, the system/process optionally includes a sweep gas and/or purge gas, respectively. In each case, the sweep gas and/or purge gas functions as a flush gas, which improves the degree of separation. In one embodiment, the separation system 125 is based on another separation technology, and a flush gas is used to improve the degree of separation. In one embodiment, the flush gas contains natural gas withdrawn from the DS 170.

Referring again to FIG. 1b, the tail gas 24 is enriched with natural gas. Natural gas is a naturally occurring hydrocarbon gas mixture composed primarily of methane, but commonly including varying amounts of other higher alkanes, and sometimes small amounts of $CO_2$, $N_2$, $H_2S$, or helium. Natural gas, which is a fossil fuel, is often transported via a distribution system (DS). The term "natural gas", as used herein, refers to the methane rich gas contained in and/or transported via a natural gas DS. It is typically fossil derived methane, but can be renewable methane. The term "natural gas", as used herein, also includes natural gas that has been compressed (e.g., compressed natural gas (CNG) or condensed (e.g., liquefied natural gas (LNG)). In general, gas introduced into a DS should meet certain pipeline specifications (e.g., methane content and/or heating values). Some exceptions may be made (e.g., for limited injections where permitted by the receiving pipeline). Pipeline specifications are known and can be readily determined from published values for a particular pipeline. For example, one value that is commonly used to qualify a methane containing gas is the heating value (e.g., in $MJ/m^3$ or $BTU/ft^3$). The heating value of gas injected into the DS may be a measured daily average or measured at an instantaneous point.

For comparative purposes only, natural gas and RNG may have a heating value between about 950 and 1150 $BTU/ft^3$, digester gas (sewage or biogas) may have a heating value between about 500 and 700 $BTU/ft^3$, and landfill gas (LFG) may have a heating value between about 400 and 550 $BTU/ft^3$.

In one embodiment, the tail gas 24 is enriched with natural gas withdrawn from a DS 170 to provide an enriched tail gas. Enriching the tail gas 24 with natural gas increases the energy content of the tail gas, and thus may support stable combustion of the tail gas 24 in combustion system 140.

In one embodiment, sufficient natural gas is mixed with the tail gas 24 to provide an enriched tail gas having a heating value of at least 400 BTU/cubic foot. In one embodiment, sufficient natural gas is mixed with the tail gas to provide an enriched tail gas having a heating value of at least 500 BTU/cubic foot. In embodiments wherein the enriched tail gas has a heating value that is similar to the heating value of the biogas (e.g., sewage, digester, or LFG based) fed to the upgrading system, the enriched tail gas may be used in any of the medium-BTU applications known in the art (e.g., direct use and/or electric power generation). The term "medium-BTU", as used herein with regard to applications and/or equipment, refers to the various applications and/or equipment, respectively, designed to use a methane-based fuel having a heating value below pipeline standards (e.g., 400-650 BTU/cf). There are many applications where raw biogas undergoes a simple cleaning to remove components such as $H_2O$ and/or $H_2S$, and then is used as a fuel without $CO_2$ removal in a medium BTU application (e.g., electricity and/or steam production). Advantageously, when the biogas has been cleaned prior to biogas upgrading 120, the enriched tail gas may be substantially water and/or $H_2S$ free, and thus is unlikely to cause corrosion to the medium-BTU equipment (e.g., may be interchangeable with cleaned biogas).

Further advantageously, using the enriched tail gas in a medium-BTU application can repurpose biogas equipment that was rendered less useful when the biogas was diverted away from the medium-BTU application for biogas upgrading (e.g., for transportation use or injection into the DS). For example, one disadvantage of upgrading biogas to RNG is that the biogas may have been used to produce heat and/or electricity for use in the biogas plant or another nearby facility. When the biogas is diverted from this medium-BTU application (e.g., heat and/or electricity production) to a biogas upgrading system 120, the medium-BTU equipment could be rendered unutilized (e.g., surplus) and there could be a loss associated with the lack of product of the medium-BTU application. For example, if the medium-BTU application provided heat and/or electricity, then the loss may correspond to a loss of income that would have been obtained if the heat and/or electricity was sold, or may correspond to a loss of heat and/or electricity that would have been used in the biogas plant and now must be imported.

The stranding of the medium-BTU equipment (e.g., where the medium-BTU equipment remains unused) generally occurs because it is designed to combust biogas (e.g., 400-650 BTU/cf) and not natural gas (i.e., >950 BTU/cf) and/or is not sufficiently efficient to burn natural gas profitably (e.g., needs low cost biogas to compete). For example, medium-BTU CHP equipment is typically smaller and/or less efficient than the larger, more efficient units commonly used and/or designed for CHP generation with natural gas. In fact, the stranding of medium-BTU equipment, in addition to the significant capital investment of biogas upgrading equipment, may increase the challenges to and/or provide a barrier to producing RNG (e.g., for transportation use). By combusting the enriched tail gas in the medium-BTU equipment, the medium-BTU equipment remains useful and a valuable investment. In addition, heat and/or electricity may continue to be generated. Notably, the heat and/or electricity generated is not considered renewable. In addition, the production of the heat and/or electricity from the enriched tail gas may be less economical than the production of heat and/or electricity from natural gas and the corresponding equipment using alternative means.

Further advantageously, by enriching the tail gas to provide a heating value substantially similar to the biogas, and using the enriched tail gas in medium-BTU applications, the medium-BTU equipment may be used with little to no modifications (e.g., little to no modifications to the piping and/or fuel burning equipment). Furthermore, since the amount of natural gas that is used to enrich the tail gas may be adjusted (e.g., in real time) a fuel having a substantially constant heating value may be provided. Accordingly, a more stable operation of the medium-BTU equipment may be achieved. In particular, enriching the tail gas with natural gas may stabilize the heating value and equalize fluctuation of gas quality. In this sense, using the enriched tail gas may be advantageous over using biogas, since biogas composition may change depending on the source(s). Some examples of medium-BTU equipment that could be used to combust the enriched tail gas include commercial, institutional, and industrial boilers (e.g., at colleges, hospitals, industries), industrial furnaces (e.g., including kilns, aggregate dryers, ovens, and waste incinerators), and electric power generation (e.g., based on reciprocating engines or combustion turbines).

Another advantage of using enriched tail gas in medium BTU equipment is that any biomethane in the tail gas is beneficially used. Conventionally, the tail gas from biogas upgrading facility is flared. Such beneficial used reduces the cost of any replacement natural gas purchases to supply the medium-BTU equipment and may provide for renewable credits (such as Renewable Electricity Certificates (RECs)) in association with the renewable portion of the fuel supply.

In one embodiment, sufficient natural gas is added to the tail gas to provide an enriched tail gas having a minimum methane composition and/or minimum heating value. For example, in one embodiment, sufficient natural gas is mixed with the tail gas to provide an enriched tail gas having a methane content of at least 35%. In one embodiment, sufficient natural gas is mixed with the tail gas to provide an enriched tail gas having a methane content of at least 40%. In one embodiment, sufficient natural gas is mixed with the tail gas to provide an enriched tail gas having a methane content of at least 45%. In one embodiment, sufficient natural gas is mixed with the tail gas to provide an enriched tail gas having a methane content of at least 50%. In one embodiment, sufficient natural gas is mixed with the tail gas to provide an enriched tail gas having a heating value of at least 350 BTU/cf. In one embodiment, sufficient natural gas is mixed with the tail gas to provide an enriched tail gas having a heating value of at least 400 BTU/cf. In one embodiment, sufficient natural gas is mixed with the tail gas to provide an enriched tail gas having a heating value of at least 450 BTU/cf. In one embodiment, sufficient natural gas is mixed with the tail gas to provide an enriched tail gas having a heating value of at least 500 BTU/cf.

In one embodiment, sufficient natural gas is added to the tail gas to provide an enriched tail gas having a methane content, heating value, or composition that is similar to the biogas from which it was derived. For example, in one embodiment, sufficient natural gas is added to the tail gas to provide a methane content that is at least 70% of the methane content of the biogas fed to the separating system (e.g., if the biogas fed to the separating system had a methane content of 50%, then the enriched tail gas would have a methane content of at least 35%). In one embodiment, sufficient natural gas is added to the tail gas to provide a methane content that is at least 75% of the methane content of the biogas fed to the separating system (e.g., if the biogas fed to the separating system had a methane content of 50%, then the enriched tail gas would have a methane content of at least 37.5%). In one embodiment, sufficient natural gas is added to the tail gas to provide a methane content that is at least 80% of the methane content of the biogas fed to the separating system (e.g., if the biogas fed to the separating system had a methane content of 50%, then the enriched tail gas would have a methane content of at least 40%).

In one embodiment, sufficient natural gas is added to the tail gas to provide a heating value that is at least 70% of the heating value of the biogas fed to the separating system (e.g., if the biogas fed to the separating system had a heating value of 600 BTU/cf, then the enriched tail gas would have a heating value of at least 420 BTU/cf). In one embodiment, sufficient natural gas is added to the tail gas to provide a heating value that is at least 75% of the heating value of the biogas fed to the separating system (e.g., if the biogas fed to the separating system had a heating value of 600 BTU/cf, then the enriched tail gas would have a heating value of at least 450 BTU/cf). In one embodiment, sufficient natural gas is added to the tail gas to provide a heating value that is at least 80% of the heating value of the biogas fed to the separating system (e.g., if the biogas fed to the separating system had a heating value of 600 BTU/cf, then the enriched tail gas would have a heating value of at least 480 BTU/cf). In one embodiment, sufficient natural gas is added to the tail gas to provide a heating value that is at least 85% of the heating value of the biogas fed to the separating system (e.g., if the biogas fed to the separating system had a heating value of 600 BTU/cf, then the enriched tail gas would have a heating value of at least 510 BTU/cf). In one embodiment, sufficient natural gas is added to the tail gas to provide a heating value that is at least 90% of the heating value of the biogas fed to the separating system (e.g., if the biogas fed to the separating system had a heating value of 600 BTU/cf, then the enriched tail gas would have a heating value of at least 540 BTU/cf).

In one embodiment, sufficient natural gas is added to the tail gas to provide a heating value that is greater than the heating value of the biogas fed to the separating system (e.g., if the biogas fed to the separating system had a heating value of 600 BTU/cf, then the enriched tail gas would have a heating value greater than 600 BTU/cf).

In one embodiment, sufficient natural gas is mixed with the tail gas to provide an enriched tail gas having a methane content within at least 10% of the methane content of the stream of biogas (e.g., if the biogas fed to the separating system had a methane content of 50%, then the enriched tail gas would have a methane content between 45 and 55%). In one embodiment, sufficient natural gas is mixed with the tail gas to provide an enriched tail gas having a methane content within at least 20% of the methane content of the stream of biogas (e.g., if the biogas fed to the separating system had a methane content of 50%, then the enriched tail gas would have a methane content between 40 and 60%). In one embodiment, sufficient natural gas is mixed with the tail gas to provide an enriched tail gas having a methane content within at least 25% of the methane content of the stream of biogas (e.g., if the biogas had a methane content of 60%, then the enriched tail gas would have a methane content between 45 and 75%).

In one embodiment, sufficient natural gas is mixed with the tail gas to provide the enriched tail gas with a ratio of $CH_4$ content to $CO_2$ content (i.e., $CH_4/CO_2$) that is close to the $CH_4/CO_2$ ratio of the biogas fed to the biogas upgrading system (e.g., within 10%, 15%, 20 or within 25%). In one embodiment, sufficient natural gas is mixed with the tail gas to provide the enriched tail gas with a ratio of $CH_4$ content to $CO_2$ content (i.e., $CH_4/CO_2$) that substantially matches the $CH_4/CO_2$ ratio of the biogas fed to the biogas upgrading system. In one embodiment, sufficient natural gas is mixed with the tail gas to provide an enriched tail gas that is substantially interchangeable with the biogas.

In one embodiment, the amount of natural gas (e.g., measured in BTU) mixed with the tail gas is at least 50% of the amount of biogas fed to the distribution system 170 (e.g., if the rate of biogas fed to DS 170 is 100 MMBTU/hr, then the amount of natural gas from system 170 mixed with tail gas exceeds 50 MMBTU/hr).

Advantageously, combusting an enriched tail gas having a methane content, heating value and/or composition (e.g., $CH_4/CO_2$ ratio) that is close to or substantially matches the $CH_4/CO_2$ ratio of the biogas that would have been combusted in the previously used combustion equipment means that the pollution control standards of the process/equipment may still be met. For example, natural gas generators may be regulated by State and/or US Environmental Protection Agency (EPA) standards. More specifically, in addition to the emission standards owners/operators must meet, there are EPA certification requirements, testing requirements, and compliance requirements. The released pollutants that may be regulated by the EPA include NOx, CO, and VOC (volatile organic compounds). While commercial natural gas generators may come EPA certified or with a "not to exceed" guarantee, biogas engines typically are subject to emissions testing. However, by providing an enriched tail gas having a methane content, heating value and/or composition (e.g., $CH_4/CO_2$ ratio) that is close to or substantially matches that of the biogas (e.g., within the compositional variation typically associated with the biogas), the emissions arising from using the enriched tail gas should not vary substantially from the emissions arising from using the biogas. Since there are no new emissions associated with the process (e.g., tail gas is not flared and/or existing combustion equipment is used to combust enriched tail gas), there is potential to accelerate development timelines (e.g., may not have to wait for approval and/or permits related to releases from the upgrading system that would otherwise be regulated). In one embodiment, sufficient natural gas is mixed with the tail gas to provide the enriched tail gas with a ratio of $CH_4$ content to $CO_2$ content (i.e., $CH_4/CO_2$) selected to maintain the level of emissions sustained when the combustion system fired biogas (e.g., within the range allowed by environmental permits granted to the biogas combustion equipment).

In some of the above described embodiments, sufficient natural gas is provided to provide an enriched tail gas having a minimum methane content and/or heating value (e.g., a methane content of 30% or a heating value of 300 BTU/cf). This is particularly advantageous in embodiments wherein the separating system is particularly efficient and provides a relatively low methane slip (e.g., wherein the methane content of the tail gas before enrichment is below about 10%, and in particular, below about 5%). For example, conventionally, if the methane slip is relatively low, the tail gas would be flared because it would be too expensive to have to add enough natural gas to provide a minimum methane content of 30%. For example, if the methane content of the tail gas before enrichment is 5% and the methane content of the enriched tail gas is 30%, then the methane content of the enriched tail gas will have been increased by about 500%. In one embodiment, sufficient natural gas is provided increase the methane content of the tail gas stream by at least 300%. In one embodiment, sufficient natural gas is provided increase the methane content of the tail gas stream by at least 400%. In one embodiment, sufficient natural gas is provided increase the methane content of the tail gas stream by at least 500%. In one embodiment, for every unit of biogas fed to the upgrading system 120 at least 0.5 unit of natural gas is withdrawn from the distribution system 170. For example, in one embodiment, for every BTU/day of biogas fed to the upgrading system 120 at least ½ BTU/day of natural gas is withdrawn from the distribution system 170. Although using fossil natural gas in the upgrading process of converting biogas to renewable natural gas, wherein the amount of natural gas used is more than half the amount of biogas originally provided, may seem counterintuitive (e.g., since it goes against the conventional practice of maximizing RNG yield while minimizing the amount of natural gas used), it may provide an economic approach to maximizing the amount of renewable natural gas produced. Notably, the amount of natural gas traditionally used in biogas upgrading has been minimized because the cost of natural gas may be relatively high and/or because it increases the GHG emissions of the process. Accordingly, one accepted practice has been to add biogas or upgraded biogas if the calorific value of a tail gas needs to be increased for destruction. However, it has been now recognized that using more natural gas (e.g., overusing relative to the minimum required for flaring) may actually be more economical (e.g., may reduce capital, operating costs, and/or may provide increased overall net revenues). In particular, using more natural gas to enrich the tail gas obviates the stranding of equipment (e.g., gets economic value from the equipment over leaving it unused), permits the generation of fuel credits for the RNG or a fuel derived from the RNG while still providing heat and/or electricity, may accelerate the permit process, and/or reduces the cost of operating the medium BTU equipment. In addition, it may reduce operating costs because energy generated from withdrawing the natural gas from the DS may be used in the compression of the RNG (e.g. prior to injection into the DS) and/or biogas (e.g., prior to being fed to the separation unit). Using natural gas to enrich the tail gas also can maximize the amount of RNG that can be produced, therefore relocating the green energy benefits of the biogas to a higher value market (e.g., transportation use and/or fuel credits). For example, in many cases, there are economic and/or environmental advantages to using a fuel derived from biogas for transportation use over other uses (e.g., electricity generation). In addition, using natural gas to enrich the tail gas may overcome pipeline receiving constraints.

Figure 5:
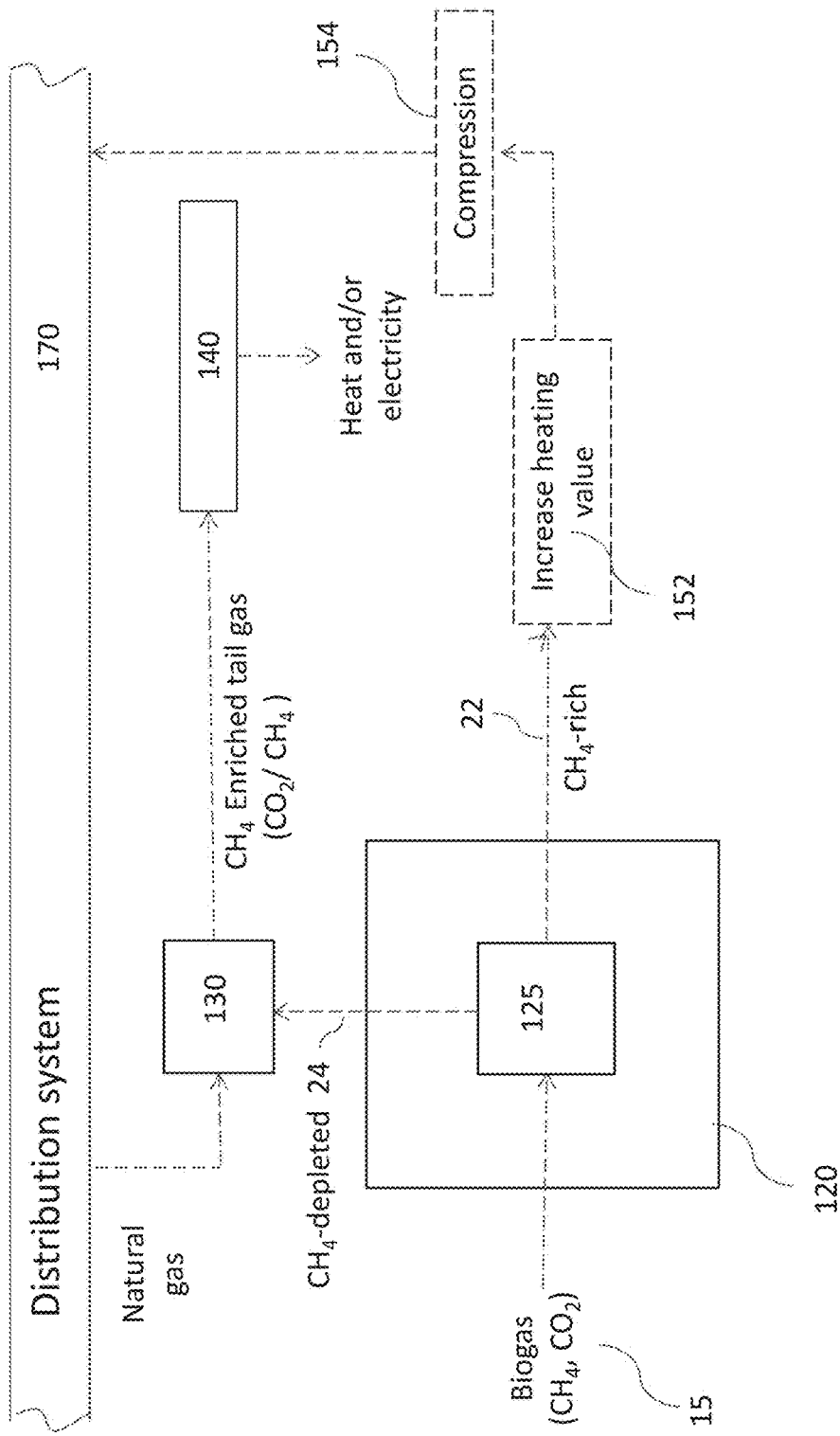
FIG. 5 is a schematic diagram showing a system for providing upgraded biogas in accordance with one embodiment of the invention, wherein tail gas is enriched by adding natural gas to the tail gas.

In one embodiment, the tail gas is enriched with natural gas by adding the natural gas to the tail gas (e.g., within the biogas upgrading system 120 or external to the biogas upgrading system 120). For example, in one embodiment, the tail gas discharged from the separating system 125 is mixed with a stream of natural gas withdrawn from a distribution system, as illustrated in FIG. 5. In this embodiment, the enriching system 130 is independent of the separation system 125. For example, in one embodiment, the enriching system 130 includes valves, regulators, and/or pipes for conveying the natural gas to the enriched tail gas. In one embodiment, the enriching system also includes a gas mixer or gas blender system. In one embodiment, the enriching system includes a commercially available computerized gas mixing system and/or gas analyzer. In one embodiment, the enriching system 130 is configured and/or disposed to enrich the tail gas 24 within the biogas upgrading system 120. In one embodiment, the enriching system 130 is configured and/or disposed to enrich tail gas 24 produced by the biogas upgrading system 120. For example, in one embodiment, the enriching system 130 is disposed downstream of the biogas upgrading system 120. In one embodiment, the enriching system 130 is configured and/or disposed to enrich tail gas 24 produced by the biogas upgrading system 120 after one or more components have been removed from the tail gas. In one embodiment, the enriching system 130 is configured and/or disposed to enrich tail gas 24 produced by the biogas upgrading system 120 after some of the tail gas has been removed (e.g., for flaring). In one embodiment, the tail gas is derived and/or obtained from any residue stream produced by the separation system 125.

Figure 6:
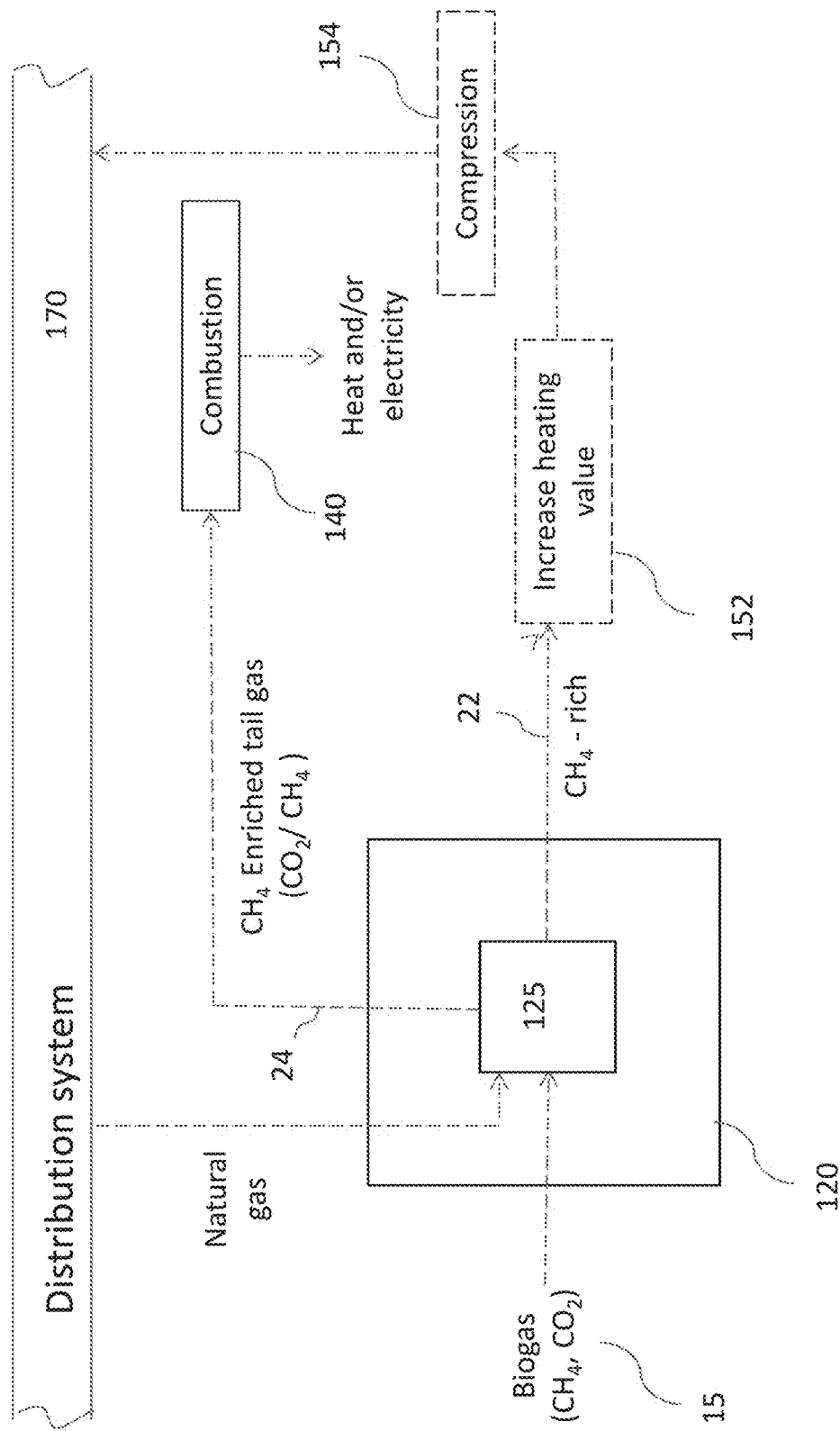
FIG. 6 is a schematic diagram showing a system for providing upgraded biogas in accordance with one embodiment of the invention, wherein tail gas is enriched by introducing natural gas into the separating system.

In one embodiment, the tail gas is enriched with natural gas by introducing the natural gas to the separating system 125 (i.e., within the biogas upgrading system 120). For example, in one embodiment, the natural gas is introduced into the separating system as illustrated in FIG. 6. In one embodiment the natural gas is introduced into the separating system and used to carry the $CO_2$ removed from the biogas out of the separating system (e.g., is provided as a purge gas for a PSA separation or as a sweep gas for membrane separation). In this embodiment, the enriching system 130 (not shown in FIG. 6) may be part of the separation system 125. In one embodiment, the enriching system 130 includes valves, regulators, turboexpander(s), and/or pipes for transporting the fossil-based natural gas to the separating system 125 for use as a sweep gas. In one embodiment, the enriching system 130 includes valves, regulators, turboexpander(s), and/or pipes for transporting the fossil-based natural gas to the separating system 125 for use as a purge gas.

Advantageously, using natural gas as a purge gas and/or sweep gas can improve the $CO_2/CH_4$ separation, while simultaneously providing a way to enrich the tail gas without using a separate mixer or mixing system. In one embodiment, the natural gas is introduced into the separating system such that the natural gas used in the enriching step aids in removing the $CO_2$ and/or improves the separation efficiency. For example, using natural gas as a sweep gas can improve the degree of $CO_2$ separation and/or reduce the required membrane area relative to a system that does not use a sweep gas.

Furthermore, using natural gas as a sweep/purge gas can be advantageous relative to using another gas (e.g., $N_2$, biogas, or upgraded biogas). For example, using natural gas as a sweep gas/purge gas may be advantageous over $N_2$ or another gas because, since the system is designed to separate $CO_2$ and renewable $CH_4$, the natural gas on the permeate side of the membrane inhibits the permeation of biomethane across the membrane into the permeate stream thus reducing biomethane slip. Using natural gas as the sweep/purge gas may be advantageous relative to using a portion of the biogas or upgraded biogas as the sweep/purge gas because it maximizes the amount of RNG produced (e.g., no additional biogas is lost in the tail gas) and available to higher value markets. In particular, by using natural gas as a sweep gas/purge gas, the amount of biogas converted to RNG and used for transportation may be maximized, thus allowing fuel credits to be generated for substantially all of the methane in the biogas. In addition, it allows the recovery of energy from the tail gas through combustion, as opposed to destruction in a flare. Using natural gas as the purge/sweep gas may be advantageous relative to using $N_2$ because it avoids introducing an otherwise unwanted and/or unnecessary compound into the system. Moreover, using $N_2$ may introduce addition expenses (e.g., cost of $N_2$) and/or challenges (e.g., related to combustion challenges resulting from the further dilution of the methane in the tail gas). In particular, using $N_2$ may affect the heating value of the tail gas, which may be particularly problematic if the sweep/ purging process is intermittent or if the concentration of methane falls below the threshold for flaring.

Figure 7:
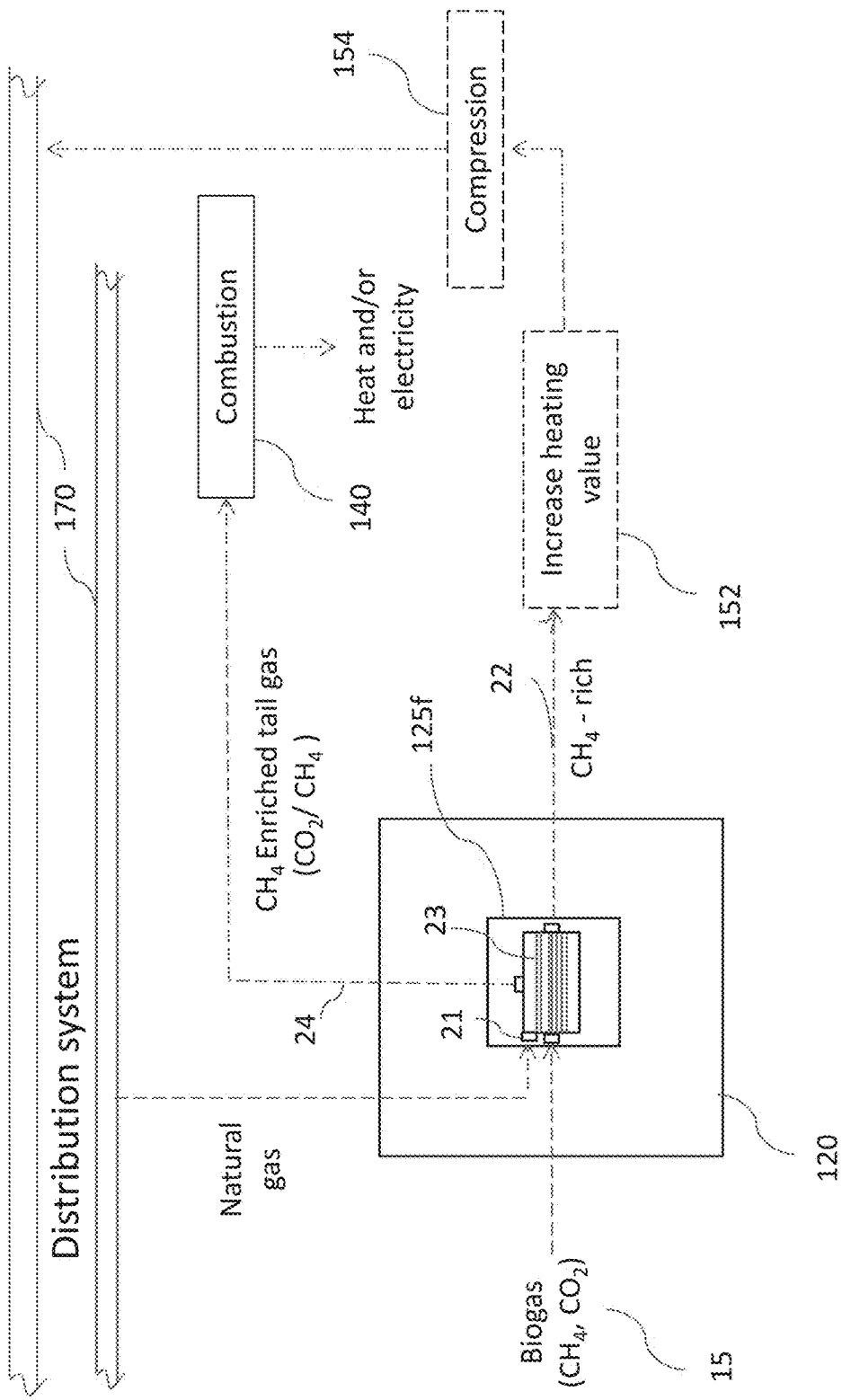
FIG. 7 is a schematic diagram showing a system for providing upgraded biogas in accordance with one embodiment of the invention, wherein the separating system includes a membrane module.

Referring to FIG. 7, there is shown a separation system 125f in accordance with one embodiment of the instant invention. The separation system 125f comprises a membrane system designed and/or configured to separate at least $CO_2$ from biogas, thereby producing upgraded biogas 22 and a $CO_2$ containing tail gas. However, the separation system 125f also includes an inlet 21 for receiving a natural gas stream. The natural gas stream is provided as a sweep gas on the permeate side of the membrane (e.g., on the opposite side of the plurality of hollow fibres 23 from the biogas feed), thereby reducing the partial pressure of $CO_2$ on the permeate side and increasing the driving force for $CO_2$ permeation and thus increasing the rate of permeation. As the natural gas sweeps the permeate (i.e., containing $CO_2$) away from the vicinity of the membrane 23, it mixes with the $CO_2$ to enrich the tail gas 24 and provide an enriched tail gas stream. Advantageously, this mixing may be performed continuously and requires no additional energy and/or equipment. Further advantageously, the flow of the natural gas sweep is controllable, thus facilitating real time control of the methane content in the enriched tail gas stream. In one embodiment, the sweep gas flow rate is selected to provide a desired $CO_2/CH_4$ ratio. In one embodiment, the sweep gas flow rate is selected to provide a desired amount of sweeping and additional amount of natural gas is added directly to the tail gas to provide the desired $CO_2/CH_4$ ratio for combustion. Notably, this separation system is advantageous regardless of whether or not the natural gas is withdrawn and/or injected into the DS 170. For example, this separating system 125f may be advantageous for providing CNG for transportation use from filling stations in close proximity to the biogas source. In addition, this separation system is advantageous regardless of whether or not the enriched tail gas is combusted for heat and/or electricity.

In one embodiment, using natural gas as a sweep gas advantageously reduces the number of membranes required and/or the power required for biogas upgrading relative to a system that does not use a sweep gas.

In one embodiment, using natural gas as a sweep gas allows a higher removal of $CO_2$ using a single stage membrane system. In one embodiment, using natural gas as a sweep gas allows the complete $CO_2$ removal process to be achieved using a single stage, and thus reduces equipment and operating costs (e.g., as a result of requiring less compression).

Figure 8:
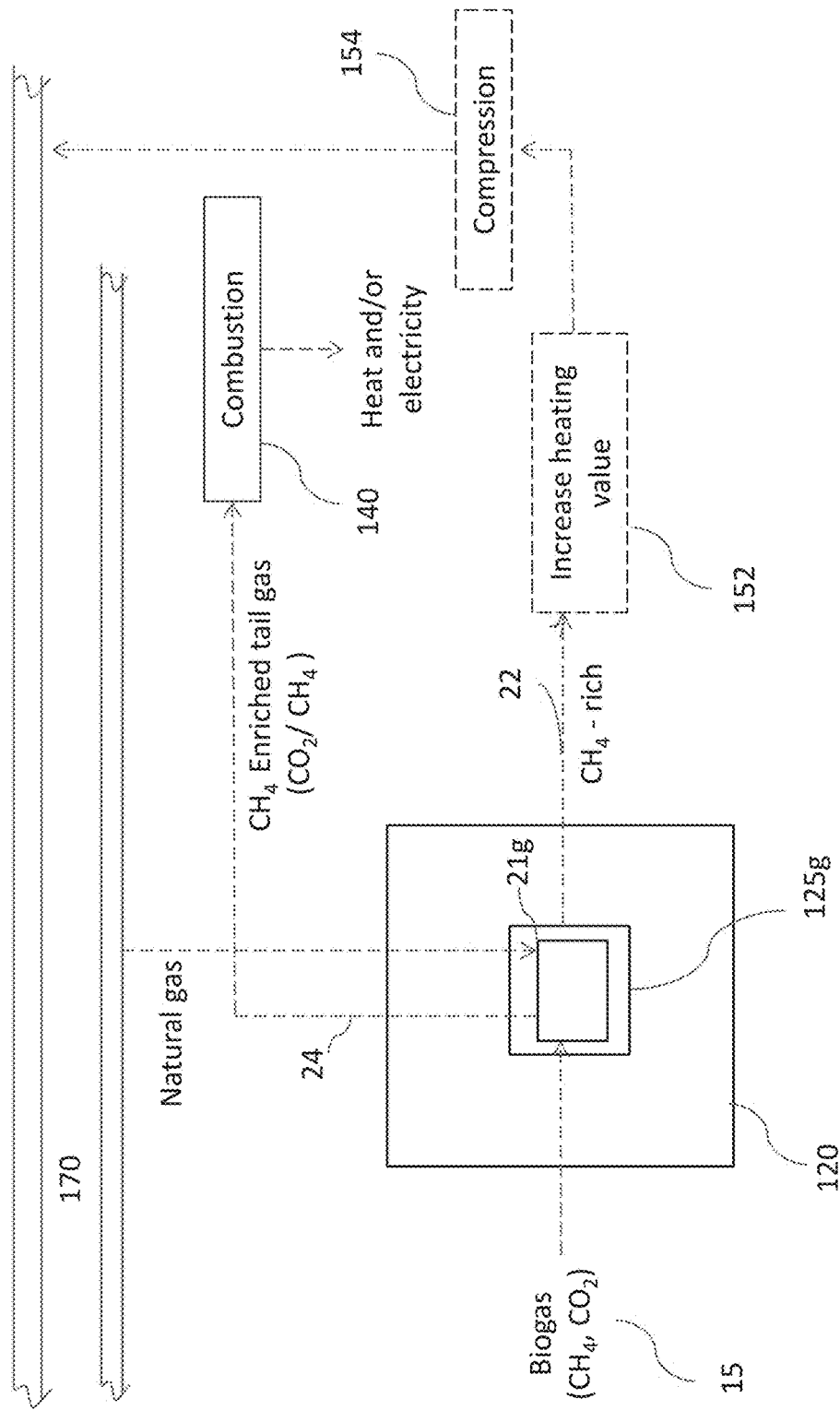
FIG. 8 is a schematic diagram showing a system for providing upgraded biogas in accordance with one embodiment of the invention, wherein the separating system includes a pressure swing adsorption (PSA) module.

Referring to FIG. 8, there is shown a separation system 125g in accordance with one embodiment of the instant invention. The separation system 125g comprises a PSA system designed and/or configured to separate at least $CO_2$ from biogas, thereby producing upgraded biogas 22 and tail gas 24. In particular, the PSA system includes a vessel having an adsorbent that retains some or all of the $CO_2$ and passes $CH_4$ such that the $CH_4$ exits the vessel and upgrading system 120 as upgraded biogas 22. The separation system 125g also includes an inlet 21g for receiving a natural gas stream. When the vessel is in the regeneration stage, the natural gas purge stream helps desorb the $CO_2$ previously retained in the column to provide tail gas 24 (e.g., containing both $CO_2$ and natural gas). Notably, only one vessel is shown for illustrative purposes, however, the system 125g may include one or more vessels. Advantageously, the tail gas containing $CO_2$ is enriched with natural gas without a separate mixing step. Further advantageously, the flow of the natural gas purge is controllable, thus facilitating real time control of the methane content in the enriched tail gas stream. Notably, this separation system is advantageous regardless of whether or not the natural gas is withdrawn and/or injected into the DS 170. For example, this separating system 125g may be advantageous for providing CNG for transportation use from filling stations in close proximity to the biogas source. In addition, this separation system is advantageous regardless of whether or not the enriched tail gas is combusted for heat and/or electricity.

In embodiments wherein the separating system includes a membrane or PSA system, it may be difficult to achieve a low methane slip without multiple stages. Advantageously, enriching the tail gas may reduce the importance of providing a low methane slip (e.g., since tail gas is used for heat and/or electricity), thus allowing the separation system to have only a single stage. Moreover, if the separation system includes a membrane with a natural gas sweep stream, the membrane sweep allows a higher removal of $CO_2$, thus providing a lower methane slip with the single stage. Advantageously, the use of a single stage membrane system reduces compression equipment and operating costs.

Combusting the Enriched Tail Gas

The combustion system 140 may include any combustion system that can use biogas as a source of methane. In one embodiment, the combustion system 140 includes medium-BTU combustion equipment. In one embodiment, the combustion system 140 produces a product such as heat and/or electricity. For example, in one embodiment the combustion system 140 uses the enriched tail gas as fuel for use in: a stove, boiler, furnace, direct fired room heater, refrigeration systems, electricity generation, and/or cogeneration (e.g., generation of electricity and heat). In one embodiment, the heat is provided as steam. In one embodiment, the combustion system 140 is used for generating heat and/or electricity for applications such as: residential use, farming, greenhouses, swimming pools, commercial facilities, and industrial processes. In one embodiment, the heat and/or electricity is provided to one or more distribution systems.

In general, the combustion system 140 may be located on-site or off-site (e.g., with regard to the biogas upgrading system 120 and/or a biogas plant producing the biogas). When the combustion system 140 is off-site, it may be located in close proximity to, or far from, the biogas upgrading system 120. In either case, the enriched tail gas may be transported via a dedicated biogas pipeline or pipeline system (not shown) to the combustion system 140. In this case, feeding at least a portion of the enriched tail gas 24 to the combustion system 140 may include and/or correspond to injecting the enriched tail gas 24 into the dedicated biogas pipeline or pipeline system.

In one embodiment, the combustion system 140 includes a gas burner. For example, in one embodiment the enriched tail gas 24 is provided for direct combustion in household applications (e.g., gas stoves or gas lamps). This embodiment may be advantageous when the biogas to be upgraded was obtained from a centralized biogas facility serving a rural or semi-urban area.

In one embodiment, the combustion system 140 includes a boiler. In this embodiment, the boiler is used to produce hot water, which may be used in various processes or heating applications (e.g., water heating, central heating, boiler-based power generation, cooking, sanitation, heat exchangers, drying sludge etc.). In one embodiment, the boiler is a commercial, institutional, or industrial boiler (e.g., the type used by colleges, hospitals, industries, etc.). For example, in one embodiment, the boiler is used on-site to heat commercial facilities. In one embodiment, the boiler is used on-site in farming applications such as crop drying, building heating (e.g., barns, greenhouses, etc.). In one embodiment, the boiler is used on-site to heat the anaerobic digester that produces the biogas 15. In one embodiment, the boiler is used on-site for heating required as part of the industrial process (e.g., cellulosic ethanol production).

In one embodiment, the combustion system 140 includes a furnace. In this embodiment, the furnace may be used to produce hot air, which may be used in various process or heating applications (e.g., central heating, drying, etc.). In one embodiment, the furnace is a commercial, institutional, or industrial furnace (e.g., the type used by colleges, hospitals, industries, etc.). For example, in one embodiment, the furnace is used on-site to heat commercial facilities. In one embodiment, the furnace is used on-site in a farming application such as crop drying, building heating (e.g., barns, greenhouses, etc.). In one embodiment, the furnace is an industrial furnace, which for example, may be used as a cement kiln, an aggregate dryer, an oven, or a waste incinerator).

In one embodiment, the combustion system 140 includes a direct-fired room heater. In this embodiment, the direct-fired room heater may be used for heating one or more rooms, such as commonly found in hog farrowing and nursery rooms.

In one embodiment, the combustion system 140 includes a biogas engine (e.g., a natural gas engine, propane engine, diesel engine, or gasoline engine modified to use biogas, or an engine designed to use biogas). In one embodiment, the biogas engine is used to drive an agricultural pump (e.g., for irrigation or effluent pumping). In one embodiment, the engine is used to run refrigeration equipment. For example, in one embodiment, the combustion system 140 includes a compressor driven by a biogas motor. In one embodiment, the combustion system 140 includes a biogas-fired adsorption or absorption chiller. In one embodiment, the refrigeration system is located on a dairy farm and is used to chill or pre-chill the milk. In one embodiment, the biogas engine is used in producing electricity.

In fact, the production of electricity from biogas and/or biogas equipment is a particularly practical application. The electricity generated may be used on-site (e.g., for on-farm use) and/or off-site (e.g., supplied to a specific user and/or the grid). For example, the electricity may provide an independent power source for residences, barns, and/or other facilities. In one embodiment, a single biogas system can power ten or more other farms. In one embodiment, the electricity is supplied to the grid to improve power quality.

In one embodiment, the combustion system 140 combusts (fires) the enriched tail gas in an engine-generator (generator set) to produce electricity. For example, in one embodiment, the engine-generator includes a combustion engine modified/designed to fire biogas and an electric generator. The combustion engine converts the fuel to mechanical energy, which powers the electric generator to produce electricity. In one embodiment, the engine is a gas engine, a diesel engine (e.g., operating in dual fuel mode), or a gas turbine. In one embodiment, the gas engine has been modified to fire biogas (e.g., to accommodate specific volumetric efficiencies and/or compression ratios). In one embodiment, the combustion system 140 comprises a CAT (Catepillar™) generator set. CAT generator sets may require a methane content that is greater than about 45%. In one embodiment, the combustion system 140 comprises a gas turbine that provides electricity. In one embodiment, the gas turbine is part of a combined cycle power plant.

Advantageously, using the enriched tail gas 24 to produce electricity may eliminate electricity costs of the process and/or generate additional revenue. In addition, if the heat from the combustion of the enriched tail gas is recovered, it may further eliminate costs of the process (e.g., heating costs) and/or provide additional revenue. In fact, one use of biogas is for fueling an internal combustion gas engine or turbine in a combined heat and power (CHP) plant, which produces electricity and heat.

In one embodiment, the combustion system 140 is part of a CHP plant. For example, in one embodiment, the combustion system 140 combusts (fires) the enriched tail gas in an engine-generator (generator set) to produce electricity, and recovers heat from the combustion of the enriched tail gas to provide heat for various process or heating applications (e.g., maintaining the operating temperature of the anaerobic digester and/or other on-farm heating uses). In another embodiment, the combustion system 140 combusts (fires) the enriched tail gas in a boiler to produce electricity, and recovers heat from the combustion of the enriched tail gas to provide heat for various process or heating applications (e.g., maintaining the operating temperature of the anaerobic digester and/or other on-farm heating uses).

In one embodiment, the heat in the CHP plant is recovered from the engine jacket and/or exhaust gas. For example, in one embodiment, heat is recovered from the engine jacket by liquid-liquid heat exchange and/or from the engine exhaust gas by a gas-to-liquid heat-exchange. In some cases, nearly half of the engine fuel energy may be recovered through this waste heat.

In embodiments wherein the combustion system 140 is part of a CHP plant, the enriched tail gas may be used in a cogeneration process that provides both electricity and heat. The electricity can be used to power the surrounding equipment or exported to the public grid. Alternatively, the electricity produced can be used to provide power to rural settlements that are off the grid. The waste heat may be used in downstream systems for additional power generation, or can be used in heating or drying processes. For example, if the CHP plant uses a gas engine, the gas engine may provide high grade heat (~450° C.) as engine exhaust gas and low grade heat (~70-90° C.) from the cooling circuits. Low grade heat may be particularly useful for heating digester tanks. Advantageously, the CHP plant may be on-site or off-site (e.g., a satellite CHP plant).

In some of the above described embodiments, the combustion system 140 may include a burner, engine, or boiler. In some embodiments, these combustion systems may use commercially available natural gas equipment adapted to fire biogas. In particular, piping, burner orifices, and/or flow control of the combustion systems may be configured to provide a specific fuel-to-air ratio that is sufficient to ensure flame stability at a certain fuel gas feed pressure. For example, a boiler system fueled by biogas typically is configured with a larger fuel orifice and restricted air intake relative to a boiler system fueled by natural gas. Furthermore, the size of the fuel orifice may need to change in dependence upon the heating value of the biogas.

Advantageously, since the enriched tail gas 24 may have a relatively constant $CH_4/CO_2$ ratio over time, the method and system based on the enriched tail gas 24 may obviate the need for equipment that allows the switchover from different fuel sources and/or fuel sources having different heating values. Furthermore, it may allow the combustion system to operate at a substantially constant volumetric throughput. This may allow for optimum performance of the equipment.

In one embodiment, the enriched tail gas is fed to one or more combustion systems. For example, in one embodiment, the enriched tail gas is combusted in at least two of any of the above-described combustion systems (e.g., which may be located in close proximity or far apart).

Injecting Upgraded Biogas into a DS

In one embodiment, the upgraded biogas 22 is injected into the distribution system 170. In one embodiment, the upgraded biogas 22 has a methane content that is greater than 95%. In one embodiment, the upgraded biogas 22 has a methane content that is greater than 97%. In one embodiment, the upgraded biogas 22 is of pipeline quality. In one embodiment, the upgraded biogas 22 injected into the distribution system is RNG. In one embodiment, the upgraded biogas does not quite meet pipeline standards and is injected in amounts that do not compromise the intended use of the combined gas. In general, the upgraded biogas 22 may be injected into any location on the distribution system 170 (e.g., in a national or regional transmission line, or within a local distribution pipeline system).

In one embodiment, the distribution system (DS) 170 includes a transmission pipeline system (e.g., including transmission pipeline(s) and the associated compressor stations, valves, and metering stations), a distribution pipeline system (e.g., including distribution pipeline(s) and the associated regulator stations, customer meters and regulators, valve box covers), and/or natural gas gathering/well pipelines (e.g., including compressor stations, valves, metering stations, wellheads, piping, manifolds).

In one embodiment, the injection of the upgraded biogas 22 is dependent on the supply of gas in the distribution system 170. For example, in some distribution systems, the amount of upgraded biogas that may be directly injected into the distribution system may be limited as a result of the current gas demand (e.g., at low demand times, such as the summer, injection into a distribution system may be limited). In one embodiment, when the demand for natural gas is low, the upgraded biogas 22 is compressed for storage and/or for direct use as a transportation use. In one embodiment, the upgraded biogas 22 is injected at one or more different sites (i.e., is transported to different regions of the DS, including regions at different pressures, in order to accommodate the demand).

As discussed above, one consideration related to upgraded biogas injection is that RNG injection may be limited based on the current demand. For example, conventionally, at times when the gas supply exceeds the momentary gas demand, the injection of RNG into the distribution system may be limited (e.g., for capacity reasons). Unfortunately, in this case the biofuel producer may lose income and/or valuable fuel credits.

However, with the method and systems described with reference to FIGS. 1a and 1b, the amount of natural gas withdrawn from the distribution system 170 and used to enrich the tail gas 24, at least partially off-sets the amount of upgraded biogas 22 injected. For example, since a relatively large amount of natural gas is withdrawn from the distribution system 170 for each unit of upgraded biogas injected, the net increase in the amount of methane within the distribution system 170 resulting from the upgrading and injection process is lower than that introduced by the upgraded biogas injection. In particular, since a relatively large amount of natural gas is withdrawn for each unit of upgraded biogas injected, the injection of the upgraded biogas into the DS may not significantly affect the supply and/or gas flow within the local region of the distribution system. Accordingly, it may be possible to inject upgraded biogas, and thus obtained valuable fuel credits, in low demand times.

In one embodiment, for every unit of upgraded biogas 22 fed to the distribution system 170 at least half a unit of natural gas is withdrawn from the distribution system 170. In general, the amount of methane containing gas that is injected and/or withdrawn from the distribution system may be measured in terms of the amount of energy delivered (e.g., gigajoules (GJ), million British thermal units (MMBtu), or British thermal units (Btu)) over a given time period.

The energy of a fuel describes the potential energy of the fuel. The term "energy content", as used herein, is a measure of energy density measured as the amount of energy contained within a volume of gas (e.g., measured in units of BTU/cubic foot or MJ/cubic meter). Heating value is one example of an energy content measurement. The heating value of gases described herein may be determined by International Organization for Standardization (ISO) test method 6976:1995, Natural Gas—Calculation of calorific values, density, relative density, and Wobbe index from composition.

The term "energy delivered", as used herein, is a measure of the amount of energy delivered to or from the distribution system in a particular time period, or series of time periods (e.g., discrete increments of time), such as, without limitation, hourly, daily, weekly, monthly, quarterly, or yearly intervals. The energy delivered may be obtained after determining values representing the energy content and volume of flow for a particular time period. In particular, the energy delivered can be obtained from the product of these two values, multiplied by a time factor according to the following equation:

$$\text{Energy delivered(BTU)}=\Sigma((\text{energy content(BTU/cubic foot)}*\text{volume of flow(cubic feet/min)}))*\text{number of minutes}$$

The energy content and/or volume of flow of the injected upgraded biogas and/or withdrawn natural gas can be measured using gas metering. For example, a gas meter may include a gas chromatogram to measure the constituents in the upgraded biogas, and subsequently from this information the energy content can be determined by known techniques. A commercial unit available on the market for carrying out such measurements is a Daniel® Danalyzer™ Model 500 Gas Chromatograph available from Emerson Process Management. Volume measurements per unit of time may be carried out with the same or a different gas meter that records a volume of flow with time using methods known to those of skill in the art. Meters for measuring energy content and volume of flow can be configured to send information digitally to a computer or computer network. Energy content and volume of flow of the upgraded biogas fed into the distribution system may be monitored. For purposes herein, monitoring includes measuring energy content and/or volume of gas flow at a single time point or over a series of time points, and/or collecting or receiving data from the instrument or testing/measuring equipment used for such measurements. The volume of flow of natural gas withdrawn from the distribution system may also be monitored.

As described above, in one embodiment, for every unit of upgraded biogas fed to the distribution system at least half a unit of natural gas is withdrawn from the distribution system 170. In one embodiment, the unit refers to energy delivered (e.g., in BTU) for a same time period. For example, in one embodiment, if over a given 24 hour period, 1000 BTU of upgraded biogas was injected, at least 500 BTU of natural gas would be withdrawn for enriching the tail gas. In another embodiment, the unit refers to the rate of energy delivered as a function of time. For example, in one embodiment, if the volume of flow at the injection site is selected to provide upgraded biogas at a rate of about 1000 BTU/hr, then the volume of flow rate at the withdrawal site is selected to provide natural gas at a rate of about 500 BTU/hr. In another embodiment, for every unit of upgraded biogas fed to the distribution system at least 0.75 a unit of the stream of natural gas is withdrawn from the distribution system.

In one embodiment, for every 1000 BTU/day of upgraded biogas fed to the distribution system at least 500 BTU/day of natural gas is withdrawn from the distribution system. In one embodiment, for every 1000 BTU/day of upgraded biogas fed to the DS, at least 600, 700, or 800 BTU/day of natural gas is withdrawn from the DS and mixed with the tail gas. In one embodiment, for every 1000 BTU/day of upgraded biogas fed to the distribution system at least 750 BTU/day of natural gas is withdrawn from the distribution system. In one embodiment, injecting the upgraded biogas 22 into and/or withdrawing natural gas from the distribution system may include measuring the energy, energy content, and/or volume of the gas injected/withdrawn. Measurements of these values may be performed at an introduction point and/or withdrawal point.

In one embodiment, for every cubic foot of upgraded biogas fed to the distribution system at least half a cubic foot of natural gas is withdrawn from the distribution system. In one embodiment, for every cubic foot of upgraded biogas fed to the distribution system at least 0.6, 0.7, 0.75, or 0.8 cubic foot of natural gas is withdrawn from the distribution system.

In one embodiment, flow rate of natural gas is withdrawn from the distribution system is at least half the flow rate of upgraded biogas injected into the distribution system. In one embodiment, flow rate of natural gas is withdrawn from the distribution system is at least 60%, 70%, 75%, or 80% of the flow rate of upgraded biogas injected into to the distribution system.

In general, the injection point where the upgraded biogas is injected, the withdrawal point from which the natural gas for enriching the tail gas is withdrawn, and the withdrawal point from which the natural gas designated for transportation use is withdrawn, will be part of the same DS 170. More specifically, the injection point and two withdrawal points (i.e., one for withdrawing natural gas for enriching the tail gas and one for withdrawing natural gas for use as a transportation fuel) may be fluidly connected through a series of connected pipes. For example, the DS 170 may include transmission lines and/or different regional distribution systems that have different owners.

In one embodiment, the injection point where the upgraded biogas 22 is injected and the withdrawal point from which the natural gas for enriching the tail gas is withdrawn are within the same region (e.g., within a common local distribution system), whereas the withdrawal point from which the natural gas for transportation use is withdrawn is in another region (e.g., for transportation use at a distant location).

In one embodiment, the injection point where the upgraded biogas is injected and the withdrawal point from which the natural gas for enriching the tail gas is withdrawn are in close proximity (e.g., within 1-10 kms). In another embodiment, the injection point where the upgraded biogas is injected and the withdrawal point from which the natural gas for enriching the tail gas is withdrawn are farther apart.

In one embodiment, the injection point where the upgraded biogas is injected and the withdrawal point from which the natural gas for enriching the tail gas is withdrawn are on a same branch of the DS such that one point is downstream of the other point (e.g., with regard to the flow of natural gas in the DS). For example, in one embodiment, the injection point where the upgraded biogas is injected is downstream of the withdrawn point (e.g., as illustrated in FIG. 1*b* if the flow of natural gas is from left to right) in order to maximize the amount of upgraded biogas that reaches different applications (i.e., so that the upgraded biogas is moved downstream and is not used to enrich the tail gas).

In one embodiment, the injection point where the upgraded biogas is injected and the withdrawal point from which the natural gas for enriching the tail gas is withdrawn are within the same geographical region (e.g., within the same distribution system), but on different branches (i.e., not upstream or downstream relative to the other, as illustrated in FIGS. 7 and 8). For example, in one embodiment, the withdrawal point from which the natural gas for enriching the tail gas is withdrawn is at or near the end of one line, while the injection point for injecting the upgraded biogas is located on another branch at a location selected to maximize use of the upgraded biogas and/or transportation use of the upgraded biogas.

In one embodiment, the injection point where the upgraded biogas is injected and the withdrawal point from which the natural gas for enriching the tail gas is withdrawn are disposed in different sections of a DS. For example, in one embodiment the withdrawal point from which the natural gas for enriching the tail gas is withdrawn from is located off a local distribution pipeline, while the injection point for injecting the upgraded biogas is located off a transmission line. Alternatively, the withdrawal point from which the natural gas for enriching the tail gas is withdrawn is on a transmission pipeline, while the injection point for injecting the upgraded biogas is located on a local distribution pipeline.

In general, the upgraded biogas 22 may or may not be further compressed prior to being injected into the DS 170. For example, in one embodiment the biogas upgrading system 120 operates at pressures that provide the upgraded biogas 22 at or near a pressure of a section of the DS 170. In other embodiments, the upgraded biogas 22 is compressed to a pressure for injecting the upgraded biogas into the DS.

Advantageously, using a system wherein the injection point and the withdrawal point (i.e., for natural gas for enriching the tail gas) are at relatively high pressures (e.g., either on a same branch, or different branch of the DS 170) may allow energy lost in the gas pressure letdown process be reused in the compression process. The energy generated during pressure letdown and the energy required for compression may be the same or different. In one embodiment, the natural gas contained within the DS 170 may be at a relatively high pressure, whereas the pipes used to transmit the withdrawn natural gas to the upgrading system 120 may be at a relatively low pressure. As the gas flows from a high pressure pipe to a low pressure pipe it expands and is cooled. If a turboexpander is provided between the high and low pressure pipes, the gas will spin the turbine, which may be coupled to a compressor or generator. In one embodiment, the turbine is coupled to a compressor that is driven by the turbine. Accordingly, the energy recovered from the pressure letdown resulting from withdrawing may be used to drive the compressor used to compress the upgraded biogas prior to injection into the DS. Advantageously, this may provide a system with less fuel consumption, improved process efficiency, and reduced environmental impact. Moreover, it reduces the cost of compressing the upgraded biogas.

In one embodiment, the upgraded biogas is enriched, odorized, and/or compressed prior to injection into the DS 170. In one embodiment, the upgraded biogas is further purified and/or cleaned before injection into the DS 170. For enriching the upgraded biogas 22 may include adding propane to the upgraded biogas and/or mixing the upgraded biogas with natural gas in order to provide the required heating value.

In one embodiment, the biogas is upgraded by a party referred to as the biofuel producer (e.g., which may be the same or different from the biogas producer). The biofuel producer may or may not provide compression of the upgraded biogas and may or may not inject the upgraded biogas into the distribution system (e.g., the upgraded biogas may be compressed and/or injected by a separate entity (e.g., a biofuel injector). A biofuel injector may be the same or different from the owner of the local section of the DS.

In one embodiment, the biofuel producer maintains a biogas cleaning and upgrading module, an enriching module, and a gas analysis, pressure control, compression, and/or odorant injection module. In this embodiment, upgraded biogas may be injected by biofuel producer or the owner of the DS at the injection location.

In one embodiment, natural gas is withdrawn from DS 170 and used for transportation use. In this embodiment, the environmental attributes of the upgraded biogas injected into the DS may be associated with the natural gas withdrawn for transportation use in order to generate fuel credits.

Figure 9A:
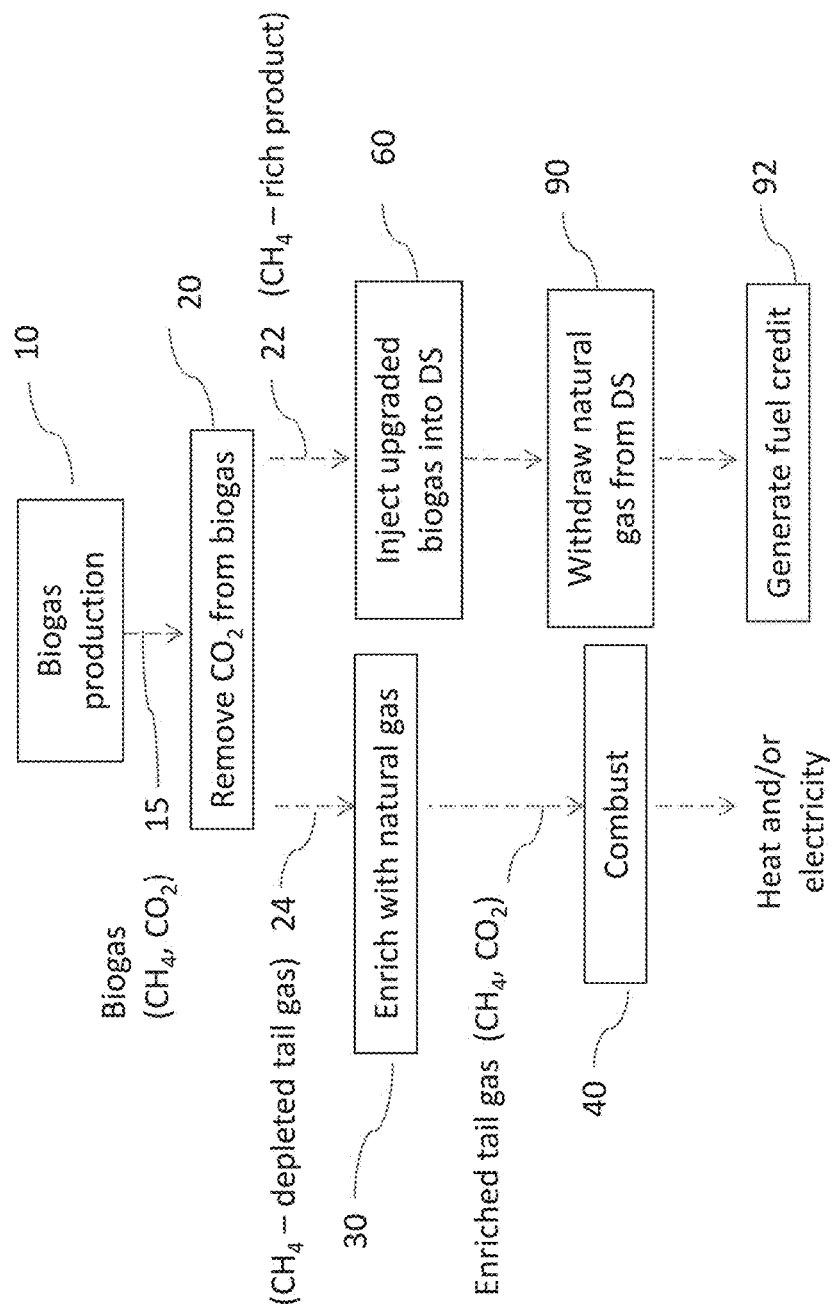
FIG. 9a is a block flow diagram of a method according to one embodiment of the invention.

Referring to FIG. 9a, there is shown a flow diagram of a method in accordance with an embodiment wherein a fuel credit is generated 92 that is associated with the natural gas withdrawn for transportation use.

In one embodiment, the environmental attributes are selected in dependence upon an allocated amount (e.g., energy delivered) of the injected upgraded biogas 90. For example, in one embodiment, 10 units of upgraded biogas (e.g., measured as energy delivered) is injected into the DS, and 25 units of natural gas is withdrawn from the DS for transportation use. Notably, the 10 units injected into the DS may have the same or different injections points. Likewise, the 25 units withdrawn from the DS may have the same or different withdrawal points. In one embodiment, one or more persons withdraw or cause the withdrawal of at least a portion of natural gas withdrawn for transportation use allocating the quantity injected to the quantity withdrawn (e.g., 10 of 25 units are allocated as renewable biogas). The term "cause" or "causing", as used herein, refers to arranging or bringing about a specific result (e.g., a withdrawal of a gas), either directly or indirectly, or playing a role in a series of activities through commercial arrangements such as a written agreement, verbal agreement, or contract. Fuel credits may be generated in association with the quantity injected.

Transfer of Title or Environmental Attributes

In one embodiment, once the upgraded biogas 22 has been injected into the DS, its environmental attributes are transferred or otherwise allocated to a different location or user in the DS. In one embodiment, the environmental attributes of the upgraded biogas are transferred or allocated to the natural gas withdrawn for transportation use. As described above, the injection point of the upgraded biogas and the withdrawal point for withdrawing natural gas for transportation use do not have to be in close proximity. Moreover, the physical gas flow direction within the DS may or may not be aligned with the direction in which the environmental attributes of the gas are transferred or allocated. The transfer is made on a displacement basis, where transactions within a DS involve a matching and balancing of inputs and outputs, and the direction of the physical flow of gas need not be considered.

In one embodiment, the transfer or allocation of environmental attributes is evidenced by a contract or other commercial arrangement (e.g., may or may not involve transfer of ownership). By transferring or allocating "environmental attributes", it is meant that the natural gas withdrawn from the DS for transportation use is considered to have the GHG emission properties of the upgraded biogas injected, as can be readily determined by those of skill in the art. Such transfer or allocation can enable the generation of fuel credits.

In one embodiment, the transfer or allocation of environmental attributes in the DS is evidenced by title transfer of the upgraded biogas fed to the DS to natural gas that is withdrawn from the DS for transportation use. In one embodiment, the transfer of environmental attributes includes transferring or causing a transfer of title of the upgraded biogas introduced to the DS to a user that withdraws or causes withdrawal of the natural gas, or to an intermediary that provides natural gas to such user. The transfer of title may be carried out via written documentation including, but not limited to, a letter, memorandum, affidavit, form, or submission to governmental authorities, or a contract that states, commits, guarantees or otherwise indicates that the environmental attributes of the upgraded biogas are transferred to the user of the natural gas or natural gas location. In one embodiment, the transfer of title may be carried out via a contract for the sale or use of a specific quantity of natural gas taken from the DS for use as a transportation fuel. Such contract may meet the standards of responsible government authorities for the generation of renewable fuel credits. The title transfer need not be a direct transfer of the upgraded biogas introduced to the DS to the user of the natural gas withdrawn. That is, the title may be transferred one or more times before its transfer to a user of the natural gas withdrawn or an upstream location.

In one embodiment, an electronic trading system is used to evidence transfer of environmental attributes, or title, to the user or location. For example, a transaction management system that tracks the introduction of the upgraded biogas and the withdrawal of natural gas from the DS may be used. Such transaction management system may include software that tracks ownership of gas introduced to the DS and gas withdrawn, which includes measurements of the amount of gas input and output from the DS. In one embodiment, inputs and outputs to the DS are tracked by flow meters and/or electronic recording. In one embodiment, inputs and outputs are traced using energy delivered. In one embodiment, there is one or more transfers of ownership before its ultimate transfer to an owner, and thus the transaction management system may track more than one transaction.

In one embodiment, the environmental attributes associated with the upgraded biogas are transferred to a user of the natural gas withdrawn for transportation use at the location where the natural gas is withdrawn. Without being limiting, natural gas withdrawn from a DS may be considered renewably derived, taking into account the displacement of fossil derived natural gas in the DS by the upgraded biogas, regardless of the location where the displacement actually occurs.

In one embodiment, one or more fuel credits are generated or caused to be generated, which are associated with the fuel withdrawn for transportation use. In one embodiment, the withdrawn natural gas is used or processed to make transportation fuel. In one embodiment, the transportation fuel includes liquid or compressed natural gas (also referred to as "LNG" and "CNG", respectively) for combustion in transportation vehicles. In one embodiment, the generation of fuel credits is associated with the quantity of upgraded biogas injected into the DS.

The value of the fuel credit(s) may be due at least in part to a transfer or allocation of environmental attributes from the upgraded biogas to the natural gas withdrawn for transportation use by calculating the value of the energy delivered for the upgraded biogas injected and the value of the energy delivered for the natural gas withdrawn for transportation use, and selecting the lower value.

In one embodiment, the natural gas withdrawn for transportation use is used as an intermediate or a feedstock to produce the transportation fuel. For example, the natural gas to which the environmental attributes have been transferred may be chemically reacted to produce renewable hydrogen, which in turn is used in a process to produce a renewable or partially renewable liquid transportation fuel. In certain embodiments, the renewable hydrogen may be combined with a crude oil derived liquid hydrocarbon so that it becomes incorporated into the hydrocarbon and ultimately becomes part of the liquid transportation fuel that is the product of the fuel production facility. (See, e.g., U.S. Pat. Nos. 8,753,843, 8,658,026 and 8,945,373).

In one embodiment, the natural gas withdrawn for transportation use is used as a transportation fuel that has life cycle GHG emissions that are at least 20% less than the life cycle GHG emissions of a gasoline baseline using EPA methodology, preferably at least 50% or 60% less.

In one embodiment, the natural gas withdrawn for transportation use is used as a fuel intermediate or a feedstock to produce a transportation fuel, where the resulting transportation fuel has life cycle GHG emissions that are at least 20% less than the life cycle GHG emissions of a gasoline baseline, preferably at least 50% or 60% less, using EPA methodology.

In one embodiment, the fuel credits generated are used to show compliance with a methodology for meeting renewable fuel targets or mandates established by governments, including legislation and regulations for transportation fuel sold or introduced into commerce in the United States. Examples of such legislation include the Energy Independence and Security Act ("EISA") and California AB 32—The Global Warming Solutions Act, which respectively established an RFS and a Low Carbon Fuel Standard (LCFS). For example, under EISA, the mandated annual targets of renewable content in fuel are implemented through an RFS that uses tradable credits (called Renewable Identification Numbers, referred to herein as "RINs") to track and manage the production, distribution, and use of renewable fuels for transportation or other purposes. Targets under the LCFS can be met by trading of credits generated from the use of fuels with a lower GHG emission value than the gasoline baseline.

In general, the environmental attributes of the upgraded biogas that are transferred or allocated to the natural gas withdrawn for transportation use may be related to the life cycle GHG emission emissions of the fuel. To determine life cycle GHG emissions associated with a fuel, analyses are conducted to calculate the GHG emissions related to the production and use of the fuel throughout its life cycle. Life cycle GHG emissions include the aggregate quantity of GHG emissions related to the full life cycle of the transportation fuel, including all stages of fuel and feedstock production and distribution, from feedstock generation or extraction, through the distribution and delivery, and use of the finished fuel to the ultimate consumer. GHG emissions typically account for total net GHG emissions, both direct and indirect, associated with feedstock production and distribution, the fuel production, and distribution and use.

Since many of the laws adopted differentiate the requirements for fuels based upon their net GHG emissions impacts, it is known to those skilled in the art that regulators have developed and/or adopted methods to analyze and characterize the expected net GHG emissions of fuel pathways. Thus, the life cycle GHG emissions are determined in accordance with prevailing rules and regulations.

Life cycle GHG emissions evaluations generally consider GHG emissions associated with each of:

feedstock production and recovery, including the source of carbon in the feedstock, direct impacts such as chemical inputs, energy inputs, and emissions from the collection and recovery operations, and indirect impacts such as the impact of land use changes from incremental feedstock production;

feedstock transport, including feedstock production and recovery and GHG emissions from feedstock transport including energy inputs and emissions from transport;

fuel production, including chemical and energy inputs, emissions and byproducts from fuel production (including direct and indirect impacts); and transport and storage of the fuel prior to use as a transportation or heating fuel, including chemical and energy inputs and emissions from transport and storage.

Examples of models to measure life cycle GHG emissions associated with the one or more products, include, but are not limited to:

GREET Model—GHGs, Regulated Emissions, and Energy Use in Transportation, the spread-sheet analysis tool developed by Argonne National Laboratories;

FASOM Model—a partial equilibrium economic model of the U.S. forest and agricultural sectors developed by Texas A&M University;

FAPRI International Model—a worldwide agricultural sector economic model that was run by the Center for Agricultural and Rural Development ("CARD") at Iowa State University;

GTAP Model—the Global Trade Analysis Project model, a multi-region, multi-sector computable general equilibrium model that estimates changes in world agricultural production as well as multiple additional models; and ISO (International Organization for Standardization) standards for GHG emissions accounting and verification—provides guidance for quantification, monitoring and reporting of activities intended to cause greenhouse gas (GHG) emission reductions or removal enhancements.

The life cycle GHG emissions or carbon intensity of the transportation fuel may be measured in carbon dioxide equivalents ($CO_2$eq). As would be understood by those of skill in the art, carbon dioxide equivalents are used to compare the emissions from various GHGs based upon their global warming potential (GWP), which is a conversion factor that varies depending on the gas. The carbon dioxide equivalent for a gas is derived by multiplying the amount of the gas by the associated GWP: grams of $CO_2$eq=((grams of a gas)*(GWP of the gas)).

The GWP conversion value used to determine g $CO_2$eq will depend on applicable regulations for calculating life cycle GHG emissions reductions. The GWP under EISA is 1, 21 and 310, respectively, for carbon dioxide, methane and nitrous oxide as set forth in Renewable Fuel Standard Program (RFS2) Regulatory Impact Analysis, February 2010, United States Environmental Protection Agency, EPA-420-R-10-006, pg. 13, of which the entire contents are incorporated herein by reference. Under California's LCFS, the GWP is 1, 25 and 298, respectively, for carbon dioxide, methane and nitrous oxide, as measured by the GREET model. It should be appreciated that GWP values can be readily calculated by those of skill in the art in accordance with regulations. GWP values may be changed by governing agencies over time.

The unit of measure for carbon intensity or life cycle GHG emissions that may be used to quantify GHG emissions of the transportation fuel is grams $CO_2$eq per MJ of energy in the fuel or grams $CO_2$eq per million British thermal units of energy in the fuel (MMBTU). The units used to measure life cycle GHG emissions will generally depend on applicable regulations. For example, under the EPA regulations, GHG emissions are measured in units of grams $CO_2$eq per million BTUs (MMBTU) of energy in the fuel. Under LCFS, GHG emissions are measured in units of grams $CO_2$eq per MJ of energy in the fuel and are referred to as carbon intensity or CI.

The term "credit", "renewable fuel credit" or "fuel credit", as used herein, refers to any rights, credits, revenues, offsets, greenhouse gas rights, or similar rights related to carbon credits, rights to any greenhouse gas emission reductions, carbon-related credits or equivalent arising from emission reduction trading or any quantifiable benefits (including recognition, award or allocation of credits, allowances, permits or other tangible rights), whether created from or through a governmental authority, a private contract, or otherwise. According to one embodiment, the renewable fuel credit is a certificate, record, serial number or guarantee, in any form, including electronic, which evidences production of a quantity of fuel meeting certain life cycle GHG emission reductions relative to a baseline set by a government authority. Preferably, the baseline is a gasoline baseline. Non-limiting examples of credits include RINs and LCFS credits. In one embodiment, the fuel credit is a RIN.

For example, a product may qualify for an advanced biofuel RIN under EISA having a D code of 3, 4, 5 or 7. In another embodiment, the product is eligible for a RIN having a D code of 3 or 5. Under the LCFS, products for use as fuels with greater reductions in life cycle GHG emissions qualify for a greater number of credits having higher market value than fuels with lower reductions.

In one embodiment, the natural gas withdrawn for transportation use is or produces a fuel that meets renewable fuel targets.

Meeting Renewable Fuel Targets Under EISA

U.S. policymakers have introduced a combination of policies to support the production and consumption of biofuels, one of which includes the Renewable Fuel Standard (RFS). The RFS originated with the Energy Policy Act of 2005 (known as RFS1) and was expanded and extended by the EISA of 2007. The RFS expanded and extended under EISA is sometimes referred to as RFS2 or RFS as used herein.

Under the EISA, the RFS sets annual mandates for renewable fuels sold or introduced into commerce in the United States through 2022 for different categories of biofuels (see Table 4 below). There is an annually increasing schedule for minimum aggregate use of total renewable biofuel (comprised of conventional biofuels and advanced biofuels), total advanced biofuel (comprised of cellulosic biofuels, biomass-based diesel, and other advanced biofuels), cellulosic biofuel, and bio-based diesel. The RFS mandates are prorated down to "obligated parties", including individual gasoline and diesel producers and/or importers, based on their annual production and/or imports.

Each year, obligated parties are required to meet their prorated share of the RFS mandates by accumulating credits known as RINs, either through blending designated quantities of different categories of biofuels, or by purchasing from others the RINs of the required biofuel categories. The RIN system was created by the Environmental Protection Agency (EPA) to facilitate compliance with the RFS. Fuel credits called RINs are used as a currency for credit trading and compliance. RINs are generated by producers and importers of renewable fuels and assigned to the volumes of renewable fuels transferred into the fuel pool. RINs are transferred with a fuel through the distribution system until they are separated from the fuel by parties who are entitled to make such separation (generally refiners, importers, or parties that blend renewable fuels into finished fuels). After separation, RINs may be used for RFS compliance, held for future compliance, or traded. There is a centralized trading system administered by the EPA to manage the recording and transfer of all RINs.

In one embodiment, a RIN is characterized as numerical information. The RIN numbering system was in the format KYYYYCCCCFFFFFBBBBBRRDSSSSSSSSEEEEEEEE where numbers are used to designate a code representing whether the RIN is separated from or attached to a specific volume (K), the calendar year of production or import (YYYY), Company ID (CCCC), Facility ID (FFFFF), Batch Number (BBBBB), a code for fuel equivalence value of the fuel (RR), a code for the renewable fuel category (D), the start of the RIN block (SSSSSSSS) and the end of the RIN block (EEEEEEEE) Under current regulations, a RIN contains much of the foregoing information and other information in the form of data elements that are introduced into a web-based system administered by the EPA known as the EPA Moderated Transaction System, or "EMTS". It should be appreciated, however, that the information required for RIN generation and/or the format of the information may change depending on prevailing regulations.

The D code of a RIN specifies the fuel type, feedstock and production process requirements and thus the D code may be used to characterize the type of RIN, as described hereinafter. The D code of a RIN is assigned a value between 3 and 7, under current regulations. The value assigned depends on the fuel type, feedstock and production process requirements as described in Table 3 to 40 C.F.R. § 80.1426. Examples of fuels assigned a D code of 3 to 7 under current regulations are provided below. These examples are for illustration purposes only and are not to be considered limiting to the invention.

TABLE 3

RIN D code examples

| D code | Category | Example of Fuel type |
|---|---|---|
| 3 | Cellulosic biofuel | Ethanol from cellulosic biomass from agricultural residues or CNG/LNG from RNG |
| 4 | Biomass-based diesel | Biodiesel and renewable diesel from soy bean oil |
| 5 | Advanced biofuel | Ethanol from sugarcane |
| 6 | Renewable fuel (conventional biofuel) | Ethanol from corn starch |
| 7 | Cellulosic diesel | Diesel from cellulosic biomass from agricultural residues |

As described previously, the RFS2 mandate volumes are set by four separate but nested category groups, namely renewable biofuel, advanced biofuel, cellulosic biofuel and biomass-based diesel. The requirements for each of the nested category groups are provided in Table 4. Renewable transportation fuels category can be satisfied with many fuel types including CNG and LNG from RNG.

The nested category groups are differentiated by the D code of a RIN. To qualify as a total advanced biofuel, the D code assigned to the fuel is 3, 4, 5 or 7, while to qualify as cellulosic biofuel the D code assigned to the fuel is 3 or 7 (Table 4).

According to current regulations, each of the four nested category groups requires a performance threshold in terms of GHG reduction for the fuel type. In order to qualify as a renewable biofuel, a fuel is required to meet at least a 20% life cycle GHG emission reduction (or be exempt from this requirement), while advanced biofuel and biomass-based diesel are required to meet at least a 50% life cycle GHG emission reduction and cellulosic biofuels are required to meet at least a 60% life cycle GHG emission reduction, relative to a gasoline baseline. As well, each nested category group is subject to meeting certain feedstock criteria.

TABLE 4

Nested category groups under RFS2

| Nested category group | Fuel type | Life cycle GHG threshold reduction relative to gasoline baseline |
|---|---|---|
| Renewable biofuel | Conventional biofuels (D code 6) and advanced biofuels (D code 3, 4, 5 or 7) | 20% |
| Advanced biofuel | Cellulosic biofuels (D code 3 or 7), biomass-based diesel (D code 4 or 7), and other advanced biofuels (D code 5) | 50% |
| Cellulosic biofuels | Biofuel derived from cellulosic material (D code 3) and bio-diesel derived cellulosic material (D code 7). | 60% |
| Biomass-based diesel | Conventional biodiesel (D code 4) or cellulosic diesel (D code 7) | 50% |

The RIN associated with one or more products obtained or derived from the process may be assigned a D code of 3, 4, 5 or 7, also referred to herein as a D3, D4, D5 and D7 RIN, respectively. In one embodiment, the RIN associated with the one or more products may be assigned a D code of 3 or 5. Under current regulations, this corresponds to cellulosic biofuel and advanced biofuel fuel types, which meet GHG emissions reductions of 60% and 50%, respectively, relative to a gasoline baseline.

In one embodiment, the fuel credit is characterized as containing numerical information associated with methane withdrawn for transportation use. In one embodiment, the fuel credit includes numerical information relating to one or more products of the process representing at least one parameter selected from (i) the type of transportation fuel; (ii) the year in which the product was produced; (iii) a registration number associated with the producer or importer; and (iv) serial number associated with a batch. In a further embodiment, at least two parameters or at least three parameters are selected from the foregoing list. These parameters relate to RIN generation, but a Low Carbon Fuel Standard (LCFS) credit may also require generation of numerical information pertaining to one or more of these parameters. The numerical information may also include one or more of the following parameters selected from: (i') a number identifying that the numerical information is assigned to a volume of the product, or separated; (ii') a registration number associated with the facility at which the product was produced or imported; (iii') a number representing a value related to an equivalence value of the product; (iv') a number representing a first-volume numerical information associated with a batch of the product; and (v') a number representing a last-volume numerical information associated with a batch of the product.

In one embodiment, the RIN or numerical information or portion thereof is provided to a government regulatory agency, including the EPA, in connection with generating a RIN. In one embodiment, the numerical information is also provided to a purchaser of the product. The numerical information described herein or portions thereof may be stored electronically in computer readable format.

The purchaser of the natural gas for use as a transportation fuel may separate the RIN. As described above, separation of a RIN from a volume of the product for use as a transportation fuel, means termination of the assignment of the RIN to a volume of fuel. RIN separation is typically carried out by a fuel blender, importer, or other obligated party. According to pre-2010 regulations, when a RIN is separated, the K code of the RIN is changed to 2. Separation of RINs may be conducted in accordance with prevailing rules and regulations, as currently provided in 40 C.F.R. § 80.1129 and 40 C.F.R. § 80.1429. In one embodiment, one or more RINs are generated, separated, and subsequently traded.

In one embodiment, the natural gas withdrawn for transportation use is provided as a liquid transportation fuel that qualifies for renewable fuel credits. In one embodiment, certain information is submitted to regulators by entities that produce the transportation fuel from the natural gas withdrawn for transportation use, or other entities as required. Such information may include contracts and/or affidavits that track the upgraded biogas from its source to the natural gas withdrawn for use as a transportation fuel. Other information such as a specific quantity of the natural gas used for transportation purposes, its heat content, percent efficiency of transfer, and/or conversion factors may be submitted to a regulator as well. Records that are kept for regulatory purposes may include: (i) documentation pertaining to the sale of the natural gas for use as transportation fuel or to make process heat for producing a renewable fuel and transfer of title; (ii) documentation showing the volume and energy content of the natural gas for use as a transportation fuel that was delivered to a facility; (iii) documentation showing the volume and energy content of biogas; (iv) information showing that the natural gas was used for transportation purposes; and/or (v) certification such as compliance certification required under Title V of the Clean Air Act.

It should be understood that the regulations under EISA, including RIN requirements and the criteria for categorization of a fuel under a particular fuel category, such as life cycle GHG emission thresholds, are described herein in accordance with current regulations. By the term "EPA methodology" with reference to determining life cycle GHG emissions relative to a gasoline baseline, it is meant using life cycle GHG calculations using methods according to prevailing regulations as required by the EPA. Such calculations can be readily determined by those of skill in the art.

(ii) Low Carbon Fuel Standard (LCFS)

In one embodiment, a credit is generated showing compliance with low carbon fuel standards established by jurisdictions within the United States or other government authorities. The credit, which includes a certificate, may be associated with one or more products from the process, and represents or is proportional to the amount of life cycle GHG emissions reduced measured relative to a gasoline baseline. The life cycle GHG emissions under low carbon fuel standards are often referred to as carbon intensity or CI.

California's LCFS currently requires that all mixes of fuel that oil refineries and distributors sell in the Californian market meet in aggregate the established targets for GHG emissions reductions. California's LCFS requires increasing annual reductions in the average life cycle emissions of most transportation fuels, up to a reduction of at least 10% in the carbon intensity, which is a measure of the life cycle GHG emissions, by 2020. Targets can be met by trading of credits generated from the use of fuels with a lower GHG emission value than gasoline baseline. Similar legislation has been implemented by the province of British Columbia, Canada, the United Kingdom and by the European Union.

According to one embodiment, a LCFS fuel credit is generated for the fuel for transportation use. In one embodiment, generating the LCFS fuel credit includes generating information associated with the fuel for transportation use. A party may generate information relating to at least one parameter selected from: (i) a reporting period; (ii) a fuel pathway code; (iii) transaction information, including type or date of a transaction; (iv) fuel production facility information; (v) fuel delivery methods; (vi) an amount of fuel used as a fossil fuel replacement, such as gasoline or diesel; and (vii) credits or deficits generated. In a further embodiment, information regarding at least two parameters, at least three parameters or at least four parameters is generated from the foregoing list.

British Columbia approved a Renewable and Low Carbon Fuel Requirements Act, which requires parties who manufacture or import the fuel into the province ensure that the renewable content and the average carbon intensity of the fuel they supply meets levels set by regulations. Fuel suppliers are required to submit annual reports regarding the renewable fuel content and carbon intensity of the transportation fuels they supply. The province allows transfers of GHG credits between fuel suppliers to provide flexibility in meeting the requirements of the regulation.

In the European Union, GHG emissions are regulated by a Fuel Quality Directive, 98/70/EC. In April 2009, Directive 2009/30/EC was adopted which revises the Fuel Quality Directive 98/70/EC. The revisions include a new element of legislation under Article 7a that requires fuel suppliers to reduce the GHG intensity of energy supplied for road transport (Low Carbon Fuel Standard). In particular, Article 7a specifies that this reduction should amount to at least 6% by 31 Dec. 2020, compared to the EU-average level of life cycle GHG emissions per unit of energy from fossil fuels in 2010. According to the Fuel Quality Directive, fuel/energy suppliers designated by member states of the European Union are required to report to designated authorities on: (a) the total volume of each type of fuel/energy supplied, indicating where the fuel/energy was purchased and its origin; and (b) the life cycle GHG emissions per unit of energy. The European Union has also promoted the use of biofuels through a Biofuel Directive (2003/30/EC), which mandates countries across the EU to displace certain percentages of transportation fuel with biofuels by target dates.

The United Kingdom has a Renewable Transport Fuel Obligation in which biofuel suppliers are required to report on the level of carbon savings and sustainability of the biofuels they supplied in order to receive Renewable Transport Fuel Certificates (RTFCs). Suppliers report on both the net GHG savings and the sustainability of the biofuels they supply according to the appropriate sustainability standards of the feedstocks from which they are produced and any potential indirect impacts of biofuel production, such as indirect land-use change or changes to food and other commodity prices that are beyond the control of individual suppliers. Suppliers that do not submit a report will not be eligible for RTFCs.

Certificates can be claimed when renewable fuels are supplied and fuel duty is paid on them. At the end of the obligation period, these certificates may be redeemed to the RTFO Administrator to demonstrate compliance. Certificates can be traded, therefore, if obligated suppliers do not have enough certificates at the end of an obligation period they have to "buy-out" the balance of their obligation by paying a buy-out price.

In one embodiment, at least one fuel credit is generated for the natural gas withdrawn from the distribution system 170 for transportation use. In one embodiment, the natural gas withdrawn from the distribution system for transportation use qualifies for the fuel credit(s) because the environmental attributes of the upgraded biogas injected into the distribution are transferred to the natural gas withdrawn for transportation use. In one embodiment, the transfer of environmental attributes includes assuming the lifecycle GHG emissions of the natural gas withdrawn from the distribution system are the same as the lifecycle GHG emissions of the upgraded biogas injected into the distribution system.

Description of an Embodiment of the Invention

Figure 9B:
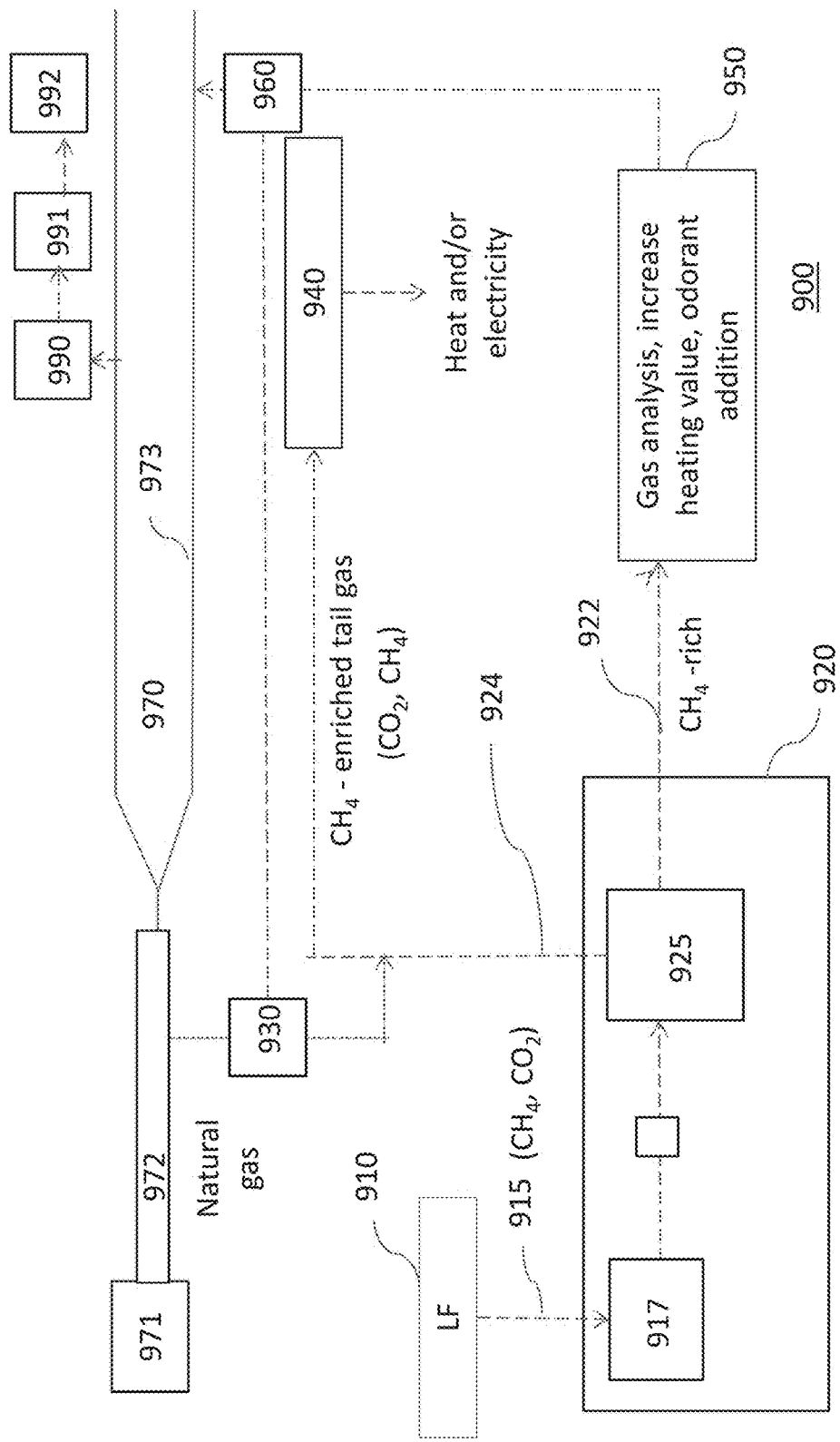
FIG. 9b is a schematic diagram showing an example of a system for providing upgraded biogas in accordance with one embodiment of the invention.

FIG. 9b shows an embodiment of a system in accordance with one embodiment of the invention. The system 900 includes a distribution system (DS) 970 having a natural gas source 971, transmission line 972, and distribution line 973. The DS 970 may also include one or more other natural gas sources, transmission lines, and/or distribution lines. The natural gas source 971 provides natural gas from fossil sources. The natural gas transported within the distribution system typically has a minimum heating value between about 950 BTU/cubic foot and 1100 BTU/cubic foot, or higher, as required by pipeline specifications.

In this embodiment, biogas 915 is produced by a landfill (LF) 910. The biogas has a heating value of about 500 BTU/cubic foot. The biogas 915 is cleaned in cleaning module 917 to remove $H_2S$ and water and is then compressed (e.g., to about 100 psi). The cleaning module 917 and separation system 925 are part of the biogas upgrading system 920. The separating system 925 includes a membrane module designed to remove $CO_2$ from the biogas (i.e., which is about 50% $CO_2$ and 50% $CH_4$). The biogas upgrading system 920 has a first outlet that provides a stream of RNG 922, and a second outlet that provides the tail gas 924 (e.g., which contains at least 80% of the $CO_2$ from the biogas fed into the upgrading system, and has a $CO_2$ content greater than about 80%).

A withdrawal system 930 is disposed between the high pressure and low pressure pipelines. The withdrawal system 930 includes, for example, a pressure control valve, a meter, and/or a turbogenerator. The pressure control valve may control the flow of a stream of natural gas withdrawn from the DS such that when the stream of natural gas mixes with the tail gas 924, the heating value of the resulting natural gas enriched tail gas is restored to about the same heating value of the biogas (e.g., within 25%, which is between about 375 and 625 BTU/cubic foot). The meter may measure the energy content in BTU/cubic foot and/or the volume of flow in cubic foot/time. The product of these two values represents the energy delivered rate in BTU per time. These values may also be measured in MJ/m$^3$ and m$^3$/time in countries outside the United States. The turbogenerator captures the energy released with the pressure letdown for use in compressing the upgraded biogas.

The natural gas enriched tail gas is fed to a combustion system 940. In one embodiment, the combustion system is a medium BTU combustion system. In one embodiment, the combustion system includes a boiler, engine, and/or turbine. In one embodiment, the combustion system is based on a technology described with regard to combustion system 140.

The upgraded biogas 922 is fed to module 950 that analyses the upgraded biogas composition and/or heating value, adds propane to the upgraded biogas in dependence upon the measured heating value, if necessary, odorizes the upgraded biogas in dependence upon pipeline requirements, and provides the resulting RNG to an injection module 960.

The injection module 960 may include, for example, a pressure control valve, a meter, an additional analyzer, and/or a compressor. In this example, the modules 950 and 960 are separate, and thus may be controlled by different parties. However, it is also within the scope of the instant invention for the two modules to be integrated.

Once the RNG has been compressed and injected into the DS at a first location 960, the environmental attributes of the RNG injected at 960 may be transferred to an equivalent amount of natural gas that is withdrawn for transportation use at 990. Alternatively, the environmental attributes of the RGN injected at 960 is transferred to natural gas withdrawn at a plurality of different locations for transportation use. Alternatively, the environmental attributes of the upgraded biogas 922 are transferred or allocated to gas used as transportation fuel at 990. Accordingly, when another party withdraws an amount of natural gas from the DS for transportation use at a second location 990, to which to the environmental attributes have been transferred, the natural gas withdrawn may be considered to be a renewable fuel. In this embodiment, the natural gas withdrawn for transportation use is compressed 991 and provided as compressed natural gas (CNG) for use in CNG vehicles. A fuel credit is generated 992 for the CNG.

If the amount of natural gas withdrawn at 990 is greater than an allotted amount of RNG injected 960 or upgraded biogas produced 922, then the fuel credit is generated only for a portion of the withdrawn amount.

Advantageously, feeding a stream of biogas to an upgrading system that provides upgraded biogas and a tail gas stream, and using each stream for a different purpose, can decrease the capital cost per MMBTU of upgraded biogas relative to the capital cost of converting the whole stream to purified biogas only (e.g., particularly when the upgrading system is based on membranes or PSA). In particular, the capital cost per unit of upgraded biogas for fuel credit generation may be lower. Moreover, it allows all or most of the biogas produced to be used for fuel credit generation, rather than at the direct use location, where the commercial value of the biogas may be lower.

Further advantageously, by enriching the tail gas stream to a suitable level any equipment previously used for combusting the biogas may continue to be used, thus obviating concerns of stranding equipment/projects. Further advantageously, by including a turboexpander in the withdrawing system 930, the energy generated from the pressure letdown may be used to power the compressor used to compress the RNG prior to injection, thereby further reducing costs.

Further advantageously, since the methane in the tail gas that originates from the biogas may be used in the medium BTU equipment (e.g., is combusted) most of the biogas is used (e.g., little to none is wasted) and little to no modification of the medium-BTU equipment is required.

EXAMPLES

Figure 10A:
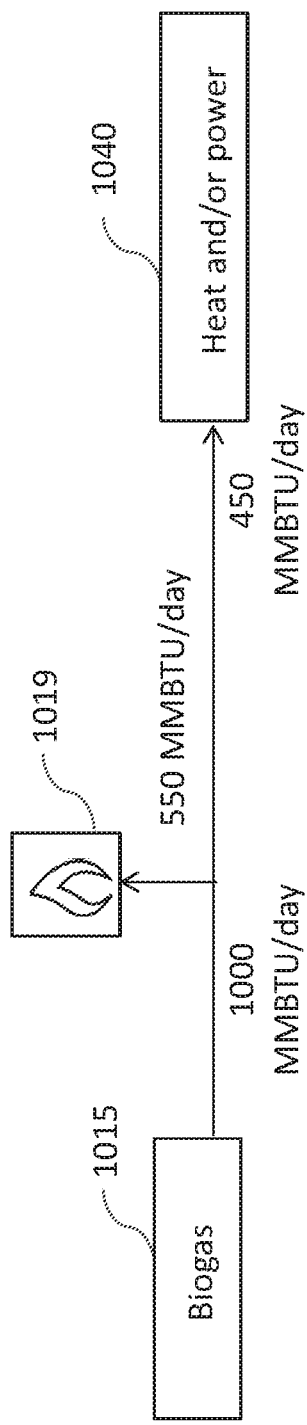
FIG. 10a is a schematic diagram showing an example where biogas is provided to a combustion system.

Comparative Examples for Producing Upgraded Biogas and/or for Producing Heat and/or Power Consider the case illustrated in FIG. 10a, where biogas produced and collected at a first location 1015 is provided for use in combustion equipment 1040 that is designed and/or configured to produce heat and/or electricity from biogas having a methane content of 49% and a heating value of 494 BTU/scf.

In this case, biogas having an average methane content of 49% and an average heating value of 494 BTU/scf is provided at a rate of 1000 MMBTU/day and is transported to the combustion equipment 1040 via a dedicated pipeline. In one embodiment, the combustion equipment 1040 is a combined heat and power (CHP) system (e.g., also referred to as a cogeneration power plant) that uses a gas turbine to produce electricity and wherein exhaust energy from the gas turbine is used to generate steam. In one embodiment, the combustion equipment 1040 is a boiler for producing steam. In either embodiment, the combustion equipment 1040 is relatively large, may have been expensive, may be difficult to move, and/or may have been selected and/or customized for the average methane content of the biogas produced at 1015. In particular, the combustion equipment 1040 is designed and/or configured to produce heat and/or electricity from biogas having a methane content of 49% and a heating value of 494 BTU/scf, and more specifically has a minimum recommended heating value of 450 BTU/scf and a minimum recommended methane content of 44.5%. In this embodiment, the combustion equipment 1040 can only accept biogas at a rate of 450 MMBTU/day. The remaining biogas is flared 1019 at a rate of 550 MMBTU/day.

While the case illustrated in FIG. 10a provides a relatively simple approach for using biogas, a lot of the biogas is wasted to the flare (e.g., does not provide a valuable product). For example, although about 45% of the available energy may be used to generate Renewable Energy Certificates (RECs), about 55% is wasted.

Figure 10B:
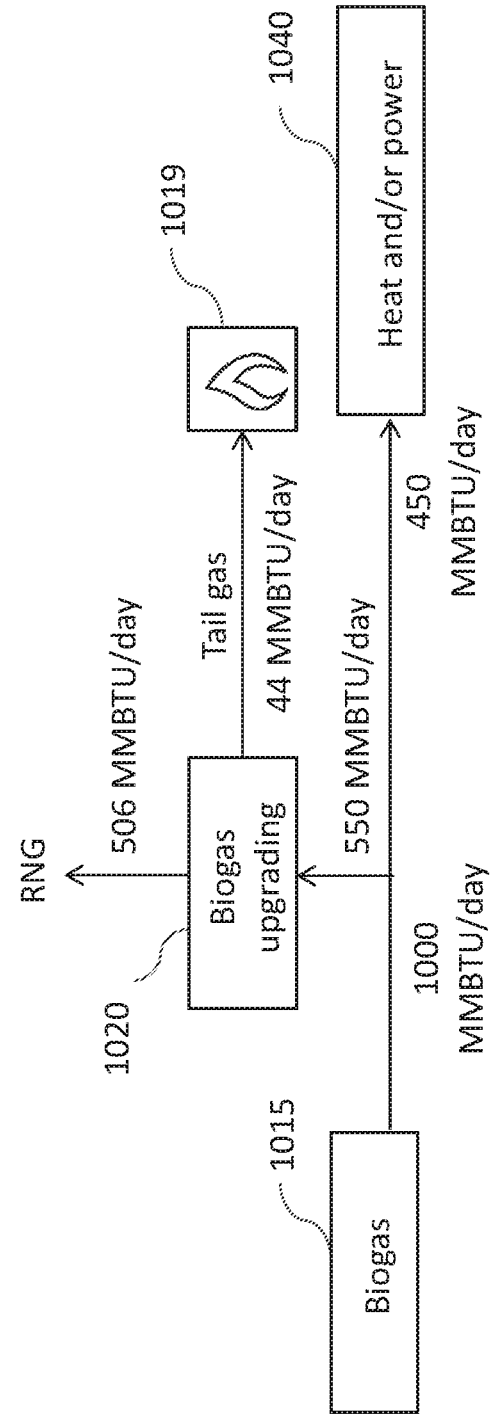
FIG. 10b is a schematic diagram showing an example where biogas is provided to a combustion system and upgraded to RNG.

Referring to FIG. 10b, the excess biogas may be provided to a biogas upgrading system 1020 (e.g., a biogas upgrading system as discussed with reference to 120). In particular, the biogas may be provided to the combustion equipment 1040 at of a rate of 450 MMBTU/day and to the biogas upgrading system 1020 at a rate of 550 MMBTU/day. In this case, the biogas upgrading system 1020 has a methane recovery rate of 92% such that RNG is produced at a rate of 506 MMBTU/day and tail gas is produced at a rate of 44 MMBTU/day. The RNG has a methane content of 96% and a heating value of 970 BTU/scf. The tail gas has a $CH_4$ content of 7% and a combined $CO_2$ and $N_2$ content of 93%. Since the minimum $CH_4$ content required to flare may be about 15%, natural gas may be added (not shown) for flaring 1019. Alternatively, the tail gas may be fed to a lean gas burner.

In this comparative case, the biogas (e.g., provided at a rate of 1000 MMBTU/day) is used to generate RNG at a rate of 506 MMBTU/day, and the balance is fed to combustion equipment 1040 at a rate of 450 MMBTU/day. Accordingly, while the same amount of renewable heat and/or power is produced using the combustion equipment 1040 (e.g., relative to the case in FIG. 10*a*), an additional amount of RNG is produced and may be injected into a distribution system/ and or used for transportation use. For example, in addition to RECs generated by combusting a portion of the biogas, fuel credits (e.g., RINs and/or LCSFs) may be generated for the upgraded portion of the biogas. Moreover, lower amounts of methane from the biogas are wasted through flaring (e.g., 550 versus 44 MMBTU/day). However, biogas upgrading systems generally benefit from economies of scale, with cost per unit of output generally decreasing with increasing scale. In particular, the capital cost of biogas upgrading systems are subject to economies of scale, where smaller plants are less capital efficient than larger plants.

Figure 10C:
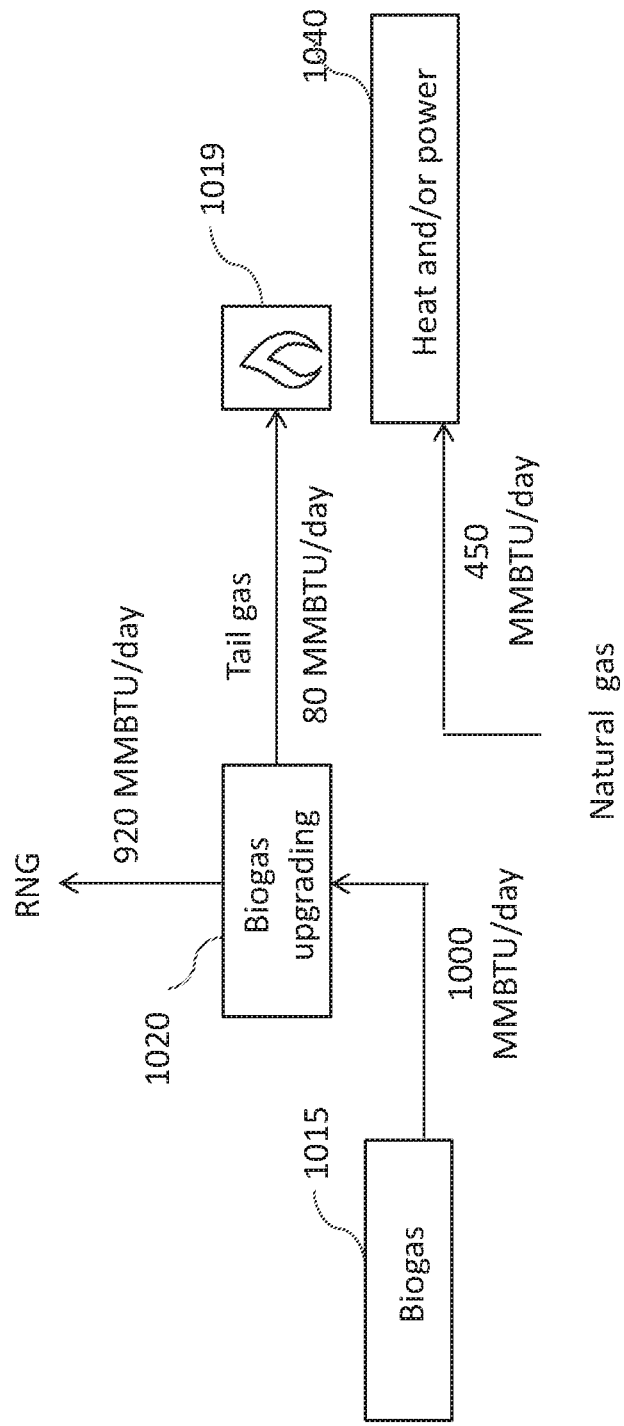
FIG. 10c is a schematic diagram showing an example where biogas is upgraded to RNG.

Referring to FIG. 10*c*, the capital cost of upgrading the biogas (e.g., per unit) is reduced by diverting all of the biogas to the biogas upgrading unit 1020, thus providing a configuration that benefits from economies of scale. Accordingly, this configuration provides more RNG and/or a more efficient upgrading system. Referring to FIG. 10*c*, the biogas is provided to the biogas upgrading system 1020 at a rate of 1000 MMBTU/day. In this case, the biogas upgrading system 1020 has a methane recovery rate of 92% such that RNG is produced at a rate of 920 MMBTU/day and tail gas is produced at a rate of 80 MMBTU/day. The RNG has a methane content of 96% and a heating value of 970 BTU/scf. The tail gas has a methane content of 7% and a combined $CO_2$ and $N_2$ content of 93%. Since the minimum $CH_4$ content required to flare may be about 15%, natural gas may be added (not shown) for flaring 1019. Alternatively, the tail gas may be fed to a lean gas burner.

In this comparative example, the amount of RNG produced is increased (e.g., 920 relative to 506). Moreover, the unit cost of upgrading is decreased (i.e., per volume of fuel as a result of economies of scale). Since the RNG may be injected into a natural gas distribution system (e.g., a commercial distribution system), the product may be available to different markets and/or may take advantage of different fuel credits. Unfortunately, in this case, no renewable heat and/or power is produced by the combustion equipment 1040. Since the biogas is diverted away from the combustion equipment 1040, and since the combustion equipment 1040 may be large and/or difficult to move, there is a risk that the combustion equipment 1040 may remained unused. This stranding of biogas combustion equipment may provide a poor return on investment.

Referring to FIG. 10*c*, stranding of the biogas combustion equipment 1040 is avoided by importing natural gas in order to replace the heat and/or power that would have been generated without a configuration change. Unfortunately, this involves replacing a relatively cheap, raw biogas, with more expensive natural gas. Moreover, no RECs can generated for the electricity generated. Furthermore, since the methane content of natural gas is generally different from the methane content of biogas, modifications to the combustion equipment and/or new permits will likely be required.

Figure 10D:
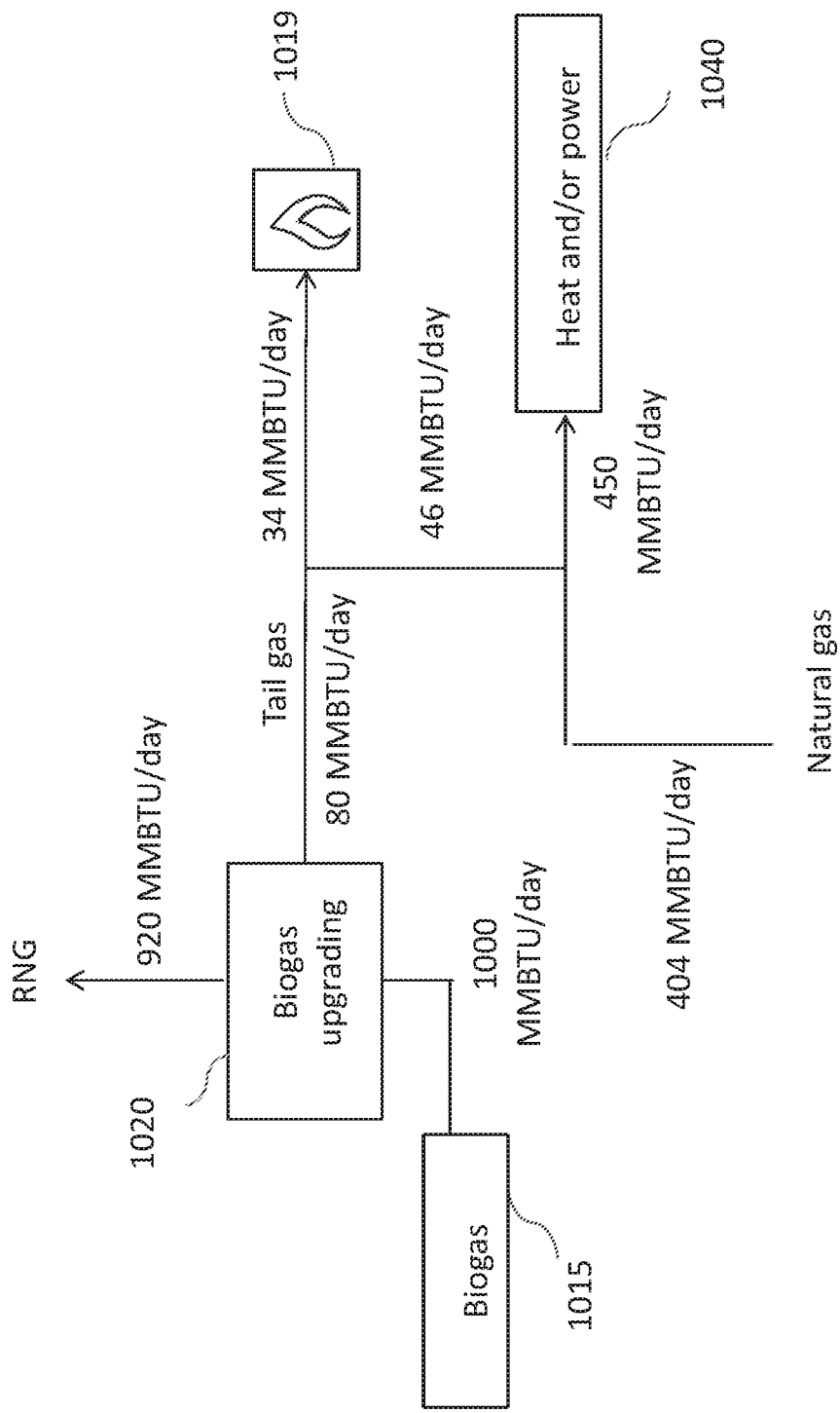
FIG. 10d is a schematic diagram showing an example where biogas is upgraded to RNG and enriched tail gas is provided to a combustion system.

Referring to FIG. 10*d*, there is shown a system in accordance with one embodiment of the instant invention. In this embodiment, the unit cost of upgrading the biogas is reduced by diverting all of the biogas to a biogas upgrading unit 1020, thus providing more RNG and/or a more efficient upgrading system. In particular, the biogas is provided to the biogas upgrading system 1020 at of a rate of 1000 MMBTU/day. In this case, the biogas upgrading system 1020 has a methane recovery rate of 92% such that RNG is produced at a rate of 920 MMBTU/day and tail gas is produced at a rate of 80 MMBTU/day. The RNG has a methane content of 96% and a heating value of 970 BTU/scf.

In this embodiment, the tail gas is enriched with natural gas to provide an enriched tail gas that is fed to the combustion system 1040 at a rate of 450 MMBTU/day. In particular, the tail gas is enriched after a portion thereof has been tapped off to be flared 1019 at a rate of 34 MMBTU/day. The enriched tail gas has a methane content of 44.5% (e.g., sufficient to meet the minimum recommended methane content of 44.5% of the combustion system 1040 and approximately 91% of the methane content of the biogas fed to the biogas upgrading system). The tail gas (before enriching) has a methane content of 7% and a combined $CO_2$ and $N_2$ content of 93%. Since the minimum $CH_4$ content required to flare may be about 15%, natural gas may be added (not shown) for flaring 1019. Alternatively, the excess tail gas may be fed to a lean gas burner.

In comparison to the examples in FIGS. 10*a* and 10*b*, the amount of RNG produced by the configuration illustrated in FIG. 10*d* is higher (e.g., 920 MMBTU/day compared to 0 MMBTU/day and 506 MMBTU/day, respectively). Since RNG may be injected into a natural gas distribution system and withdrawn at a different time and/or location, more RNG is available to the larger market.

In comparison to the example in FIG. 10*c*, the configuration illustrated in FIG. 10*d* uses less natural gas to generate the same amount of heat and/or power with the combustion equipment 1040 (e.g., 404 MMBTU/day compared to 450 MMBTU/day). Accordingly, the operating costs and/or GHG emissions for the overall process are lower.

In comparison to the examples in FIGS. 10*b* and 10*c*, the configuration illustrated in FIG. 10*d* wastes less renewable $CH_4$ by flaring. In particular, only 34 MMBTU/day is wasted compared to the 80 MMBTU/day flared in FIG. 10*c* and the 44 MMBTU/day flared in FIG. 10*b*. In other words, the configuration illustrated in FIG. 10*d* provides an extra 46 MMBTU/day of renewable fuel compared to the configuration illustrated in FIG. 10*c*. In embodiments wherein the combustion equipment produces electricity, this extra 46 MMBTU/day may be used to generate RECs.

Advantageously, the configuration illustrated in FIG. 10*d* allows the renewable $CH_4$ from the biogas to be used in different applications, thus increasing the GHG reductions. For example, the upgraded biogas may displace fossil fuels that would have been used in transportation applications, whereas the renewable $CH_4$ in the tail gas may displace natural gas used to produce heat and/or electricity using combustion equipment 1040.

Energy and/or GHG Savings from Using Turboexpander

In conventional biogas upgrading, one step that increases the cost of the process is compressing the upgraded biogas to a pressure selected in dependence upon the pipeline pressure (e.g., for injection into the distribution system). For example, if the pipeline pressure is about 800 psi, then the upgraded biogas is typically compressed to increase its pressure to about 800 psi. The energy required for this compression may represent a large operating cost of the biogas upgrading. Furthermore, the compression may require relatively large and/or expensive multi-stage compression system.

In contrast, gas withdrawn from the distribution system may be subject to a pressure let-down wherein the pressure is reduced to a level selected for a particular application. For example, the pressure may be reduced in a pressure let down station that uses one or more throttle valves. Alternatively, one or more turboexpanders may be used to capture the energy otherwise lost in the gas pressure letdown process (e.g., as natural gas is withdrawn from the distribution system).

Figure 11:
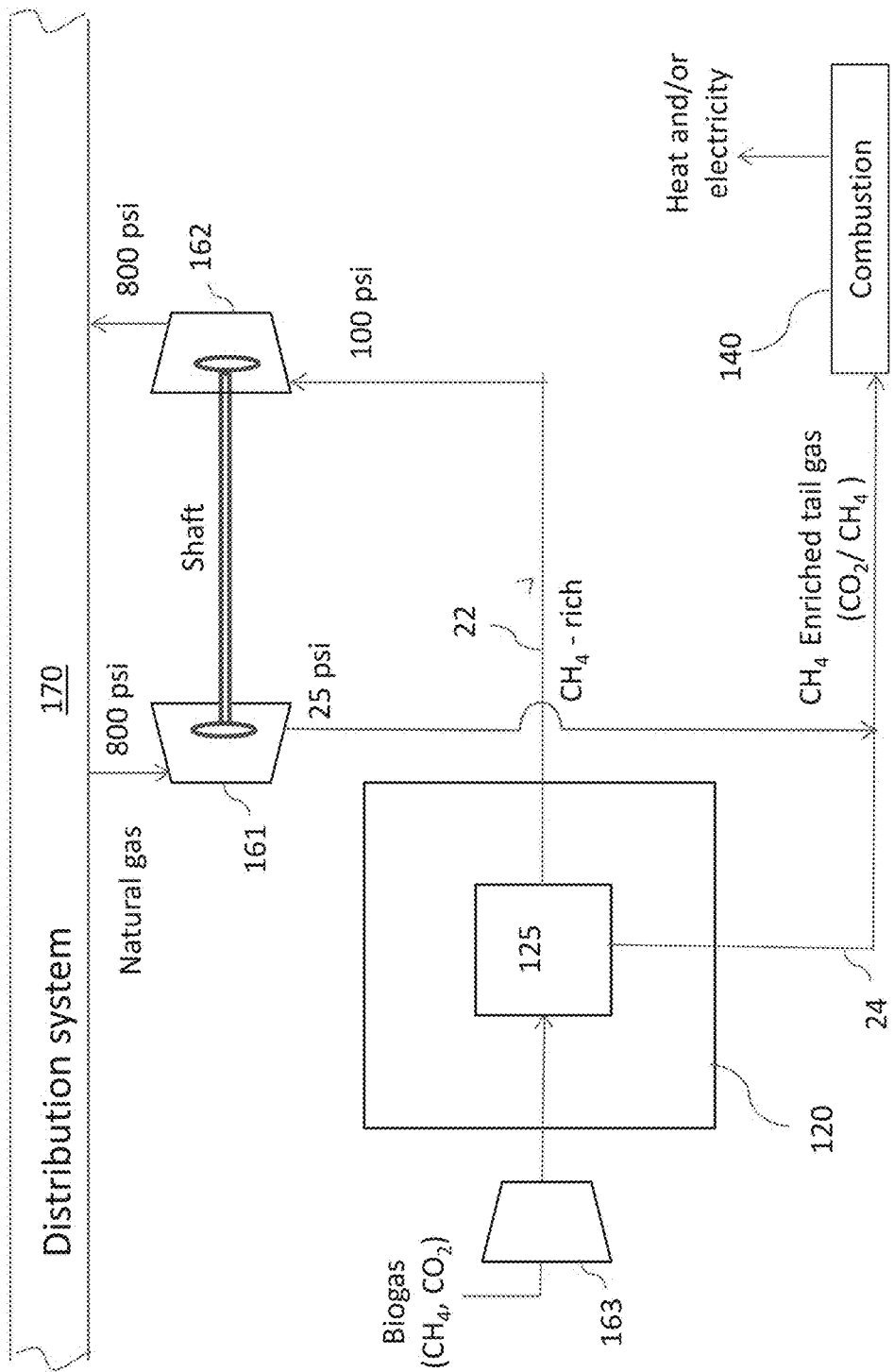
FIG. 11 is a schematic diagram showing an embodiment of a system for providing upgraded biogas that includes a turboexpander.

Referring to FIG. 11, there is shown an embodiment of the instant invention wherein the separating system 125 includes a membrane that provides a $CH_4$-rich retentate 22 at a pressure of about 100 psi. The $CH_4$-depleted permeate 24 is enriched with natural gas withdrawn from the distribution system 170. A turboexpander 161/162 is provided to reduce the pressure of the natural gas withdrawn from the distribution system 170 (e.g., from about 800 psi to about 25 psi) before it is mixed with a tail gas obtained and/or derived from the $CH_4$-depleted permeate 24. The turboexpander 161/162 is formed from a turbine 161 and a compressor 162 connected by a shaft. As the relatively high pressure natural gas flows from the high pressure pipe and into the turbine 161, it spins the turbine 161 and drives the shaft connecting the turbine 161 and compressor 162. Since the rotating shaft provides at least some of the energy for compressing the upgraded biogas (e.g., turns the centrifugal impeller of the compressor 162), the amount of energy needed to be imported for compression of the upgraded biogas may be reduced. Alternatively, and/or additionally, the energy captured from the turbine 161 is used to reduce compression costs of compressing the raw biogas prior to feeding it to the separating system 125 (e.g., in an alternate embodiment the shaft may instead couple to and/or drive the compressor 163).

In one embodiment, the relatively low pressure gas (e.g., at about 25 psi), which has been cooled by the expansion of the gas, is optionally warmed by a heater or heat exchanger (not shown). For example, in one embodiment, the waste heat generated by the compressor 162 is used to at least partially offset the cooling effect of the expansion turbine 161 and/or the cooling effect provided by the expansion turbine 161 is used to at least partially offset the heat generated by the compressor 162. Advantageously, this symbiosis between the expansion turbine 161 and the compressor 162 increases the net efficiency of the entire system. Moreover, this symbiosis may significantly reduce operating costs. For example, one disadvantage of using an expansion turbine rather than a throttle valve for pressure letdown is that the expansion of the gas in the expansion turbine typically is associated with a temperature drop that requires pre- and/or post heaters. Use of pre- and/or post heaters increases the operating costs relative to regular let down stations. However, when the waste heat generated by the compressor 162 is used to pre- and/or post heat the gas flowing through the expansion turbine 161, this operating cost is reduced.

In the embodiment illustrated in FIG. 11, the expansion turbine 161 and compressor 162 are provided as an integrated turbine-compressor system (e.g., turboexpander 161/162). In another embodiment, the expansion turbine 161 is coupled to a generator (not shown) and electricity generated therefrom is used to drive the compressor 162. Advantageously, providing an integrated turboexpander 161/162 reduces energy losses.

In one embodiment, the turboexpander 161/162 includes a radial inflow expansion turbine and a centrifugal (booster) compressor combined as an assembly. In one embodiment, the expansion turbine 161 is an axial turbine. In one embodiment, the expansion turbine 161 is a radial turbine. In one embodiment, the expansion turbine 161 and compressor 126 are coupled with a shaft and gearbox. In one embodiment, the turboexpander 161/162 includes a multi-stage turbine, a multi-stage compressor, and/or a plurality of turbines and/or compressor units (e.g., arranged in parallel or series). For example, in one embodiment, the compressor 162 is a compressor system including a plurality of compressor units. In one embodiment, the turboexpander 161/162 replaces a conventional control valve (e.g., throttle valve) or regulator. In one embodiment, the turboexpander 161/162 is mounted on one or more skids.

As discussed above, using the turboexpander 161/162 reduces the amount of energy to be imported, and thus operation costs, related to compressing the upgraded biogas (e.g., relative to a system that does not withdraw natural gas for enriching the tail gas). In general, the Horsepower available to the compressor 162 may be related to the Horsepower generated by the expander turbine 161 as follows:

$$HP_{Compressor} = HP_{Expander} - HP_{Bearings}$$

Since the power recovery potential of the expander 161 is at least partially related to the pressure ratio (i.e., ratio of inlet pressure to outlet pressure, where higher pressure ratios result in higher power production) and/or the flow rate (e.g., where higher flow rates result in higher power production), withdrawing larger volumes of natural gas from the distribution system 170 and feeding them to the turbo generator 161 may generate more Horsepower for the compressor 162, thus reducing compression costs. In embodiments where for every BTU/day of upgraded biogas fed to the distribution system at least half a BTU/day of natural gas is withdrawn from the distribution system, these cost savings may be significant. For example, if it takes 140 horsepower (HP) to compress 1 MMSCFD of RNG at 100 psi to 800 psi, and assuming that ¼ of this power may be provided by the expander 161, then only 105 additional Horsepower is required for compression. In other words, there is a savings of 35 HP, or about 27 kW (e.g., 648 kWh per day, or about $65 day, or $23,652 per year, assuming electricity is imported at rate of about 10 c/kWh). In embodiments where the expander 161 provides more than ½ of the power required for compression, the savings are increased.

Although in embodiments wherein for every BTU/day of upgraded biogas fed to the distribution system only half a BTU/day of natural gas is withdrawn from the distribution system the expander 161 is likely to generate less power than is required by the compressor 162, there are a number of synergies and/or advantages provided by the configuration illustrated in FIG. 11 that increase the ratio of the amount of power generated by expansion to the amount of power required for compression. For example, in the embodiment illustrated in FIG. 11, the pressure difference for compression (e.g., 800 psi−100 psi=700 psi) is less than the pressure difference for expansion (e.g., 800 psi−25 psi=775 psi). Moreover, the pressure ratio for compression (e.g., 800 psi/100 psi=8) is less than the expansion ratio across the expander turbine (e.g., 800 psi/25 psi=32). Providing a system where the pressure ratio for compressing gas to be injected into the DS is smaller than the expansion ratio of gas withdrawn from the DS may further decrease operating costs of compression. Furthermore, since it takes more energy to compress the upgraded biogas to 100 psi, than for each subsequent 100 psi increment, significant energy savings are provided by this configuration. In addition, there may be a difference in efficiency between the expansion and the compression. For example, typical expansion turbine efficiencies may be in the 85% to 90% range, whereas typical compressor efficiencies may be in the 75% to 85% range.

Figure 12A:
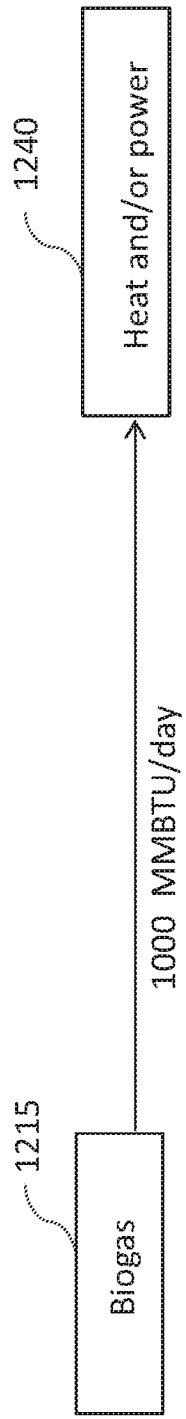
FIG. 12a is a schematic diagram showing an embodiment of a system including the combustion of raw biogas.

Comparative Example Wherein Producing Upgraded Biogas Reduces Problems from Siloxanes Consider the case illustrated in FIG. 12a, where biogas produced and collected at a landfill site 1215 is provided for use in combustion equipment 1240 that is designed and/or configured to produce heat and/or electricity from landfill gas.

In this embodiment, the raw biogas has a $CH_4$ content between about 47% and about 57%, a $CO_2$ content between about 37% and about 43%, an $O_2$ content that is less than about 1%, and a $N_2$ content that is between about 1% and about 17%. The raw biogas also has an average siloxane concentration that is between about 20 mg/m$^3$ and about 100 mg/m$^3$. Notably, these concentrations are provided for exemplary purposes only. In practice, the amount of each component and/or concentration of siloxanes will be dependent on the specific landfill. In this embodiment, the raw biogas is provided at a rate of 1000 MMBTU/day and is transported to the combustion equipment 1240 via a dedicated pipeline. In this embodiment, the combustion equipment 1240 includes an internal combustion engine (e.g., a Caterpillar Engine) for producing heat and/or electricity. Electricity generated by the engine can be used to supplement electricity requirements and/or may be sold to the electrical grid. Heat generated by the engine may be recovered and used for heating.

In this embodiment, the raw biogas is fed to the combustion equipment 1240 as is. Accordingly, any siloxanes present in the biogas may have negative effects on the engine, performance, and cost of operation. For example, the combustion of siloxanes in the engine may result in $SiO_2$ deposits on the spark plugs, pistons, cylinder heads, and/or engine valves. In fact, since $SiO_2$ deposits can be damaging, difficult to remove, and/or result in costly engine overhauls, many manufacturers set maximum siloxane limits, with warranty provisions linked to the siloxane limits. For example, the manufacturer siloxane limit for one engine is 28 mg/m$^3$ (e.g., 1.85 ppmV, based on D5). However, since the cost of siloxane removal may be large (e.g., increasing the total plant operation/maintenance costs), and in particular, may be larger than the increased engine maintenance costs resulting from $SiO_2$ deposits, this configuration (e.g., FIG. 12a) may be selected over other configurations wherein the raw biogas is subject to siloxane removal prior to combustion.

Figure 12B:
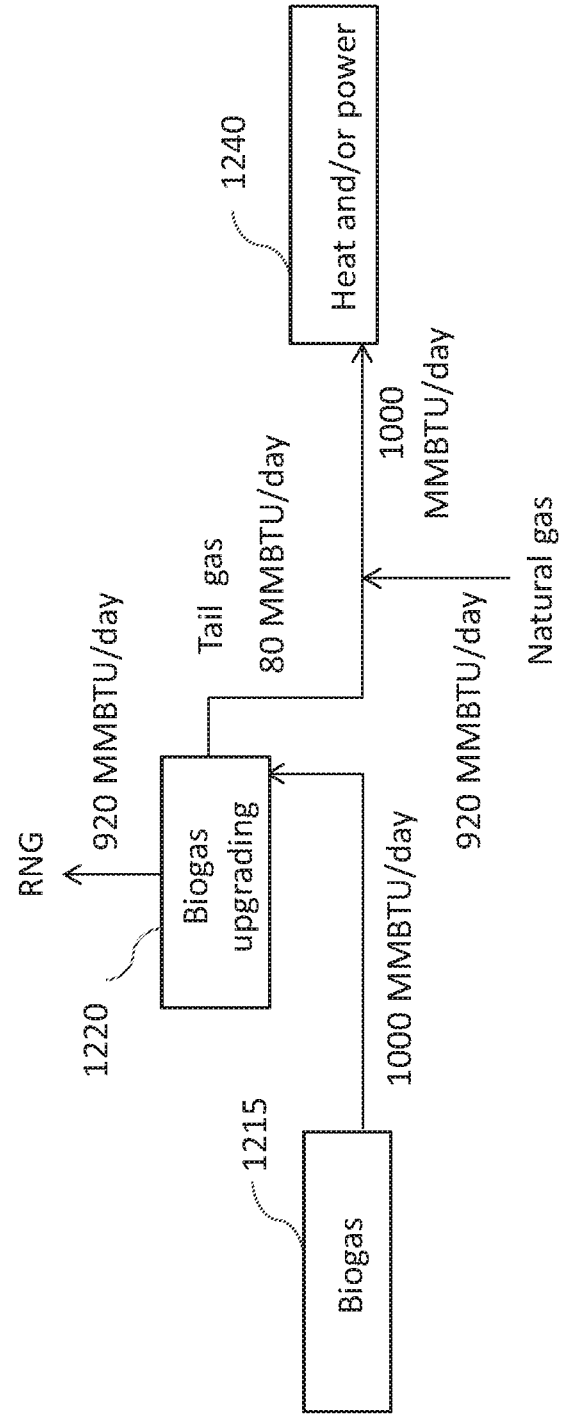
FIG. 12b is a schematic diagram showing an embodiment in accordance with an embodiment of the invention including the combustion of enriched tail gas having a siloxane concentration that is less than the raw biogas.

Referring to FIG. 12b, there is shown a configuration wherein the system illustrated in FIG. 12a is retrofitted with a biogas upgrading system (e.g., a biogas upgrading system as discussed with reference to 120, including a tail gas enriching system). More specifically, raw biogas from a landfill site 1215 is fed to a biogas upgrading system 1220 (e.g., a biogas upgrading system as discussed with reference to 120) at a rate of 1000 MMBTU/day. In this case, the biogas upgrading system 1220 has a methane recovery rate of 92% such that RNG is produced at a rate of 920 MMBTU/day and tail gas is produced at a rate of 80 MMBTU/day. The RNG has a methane content of 96% and a heating value of 970 BTU/scf.

The tail gas is enriched with natural gas to provide an enriched tail gas that is fed to the combustion system 1240 at a rate of 1000 MMBTU/day. In particular, the tail gas (e.g., provided at a rate of 80 MMBTU/day) is mixed with natural gas (e.g., provided at a rate of 920 MMBTU/day) before being fed to the combustion system 1240. Since the biogas upgrading system 1220 is configured to produce a tail gas containing most of the $CO_2$ and $N_2$ separated from the bulk of the $CH_4$, the enriched tail gas has a $CH_4$ content between about 47% and about 57% and a $CO_2$ content between about 37% and about 43%, and thus is substantially interchangeable with the raw biogas from landfill 1215. Notably, the $CH_4$ content of the enriched tail gas (e.g., in the range from 47% and 57%) includes both a renewable content (e.g., from methane slip) and a fossil-based content (e.g., the natural gas withdrawn from a distribution system).

Advantageously, since the combustion system 1240 in FIG. 12b is fed a fuel having substantially the same $CH_4$ and $CO_2$ content as the raw biogas, emissions from the combustion system 1240 should not change relative to emissions from the combustion system 1240 of FIG. 12a. Although not all of the electricity produced by combustion system 1240 in FIG. 12b will be eligible for RECs, there may be a portion that does qualify. In any case, the RNG produced by the biogas upgrading system 1220 may qualify for fuel credits.

In this embodiment, the biogas upgrading system 1220 includes a siloxane removal system, which reduces the amount of siloxanes in the biogas prior to the $CH_4/CO_2$ separation. Accordingly, neither the upgraded biogas (i.e., the RNG) nor the enriched tail gas (i.e., fed to combustion system 1240) contains a significant amount of siloxanes. Accordingly, the combustion system 1240 may be operated with a lower risk of siloxane related damages and/or increased maintenance related to relatively high levels of siloxanes. Moreover, since the cost of both siloxane removal and/or the cost of natural gas for enriching the tail gas may be associated with the biogas upgrading system 1220, overall operation/maintenance costs associated with the combustion system 1240 may be reduced (e.g., as a result of relatively low siloxane levels).

In one embodiment the siloxane concentration is reduced such that the collective amount of siloxane in the upgraded biogas and in the enriched tail gas is less than 15% of the amount of siloxane in the raw biogas. In one embodiment the siloxane concentration is reduced such that the collective amount of siloxane in the upgraded biogas and in the enriched tail gas is less than 25% of the amount of siloxane in the raw biogas. In one embodiment the siloxane concentration is reduced such that the collective amount of siloxane in the upgraded biogas and in the enriched tail gas is less than 50% of the amount of siloxane in the raw biogas. In one embodiment the siloxane concentration is reduced such that the collective amount of siloxane in the upgraded biogas and in the enriched tail gas is less than 75% of the amount of siloxane in the raw biogas.

In one embodiment the siloxane concentration of the enriched tail gas fed to the combustion system 1240 is reduced such that it is less than 15% of the siloxane concentration of the raw biogas. For example, in one embodiment, if the raw biogas would have been fed to the combustion system with a siloxane concentration of 20 mg/m$^3$, then siloxane removal results in the siloxane concentration of the enriched tail gas fed to the combustion system being reduced to less than about 3 mg/m$^3$. In one embodiment the siloxane concentration of the enriched tail gas fed to the combustion system 1240 is reduced such that it is less than 25% of the siloxane concentration of the raw biogas.

Comparative Example Wherein Natural Gas is Used as a Sweep Gas

Figure 13A:
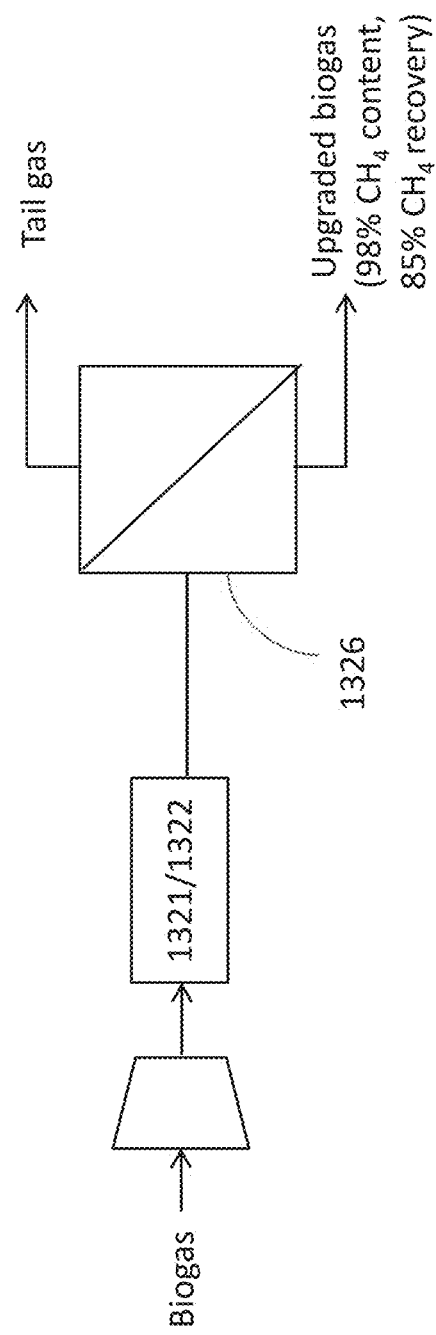
FIG. 13a is a schematic diagram showing an embodiment wherein biogas is upgraded using a single stage membrane system.

Consider the case illustrated in FIG. 13a, where biogas is compressed (e.g., to about 200 psi), is subject to a $H_2S$ 1321 and/or $H_2O$ 1322 removal process, and is fed to a membrane system 1326. The membrane system 1326 removes $CO_2$ from the biogas to produce upgraded biogas, which has a higher $CH_4$ content than the biogas fed to the membrane system 1326, and tail gas, which has a lower $CH_4$ content than the biogas fed to the membrane system 1326. In this embodiment, the membrane system 1326 is a single stage membrane. However, single stage membranes typically cannot meet methane purity (e.g., greater than 98%) and methane recovery (e.g., greater than 98%) requirements. For example, in this embodiment, the membrane system has been calculated to provide upgraded biogas having a methane content greater than >98%, but only with a methane recovery of 85%. About 15% of the methane remains in the tail gas.

Figure 13B:
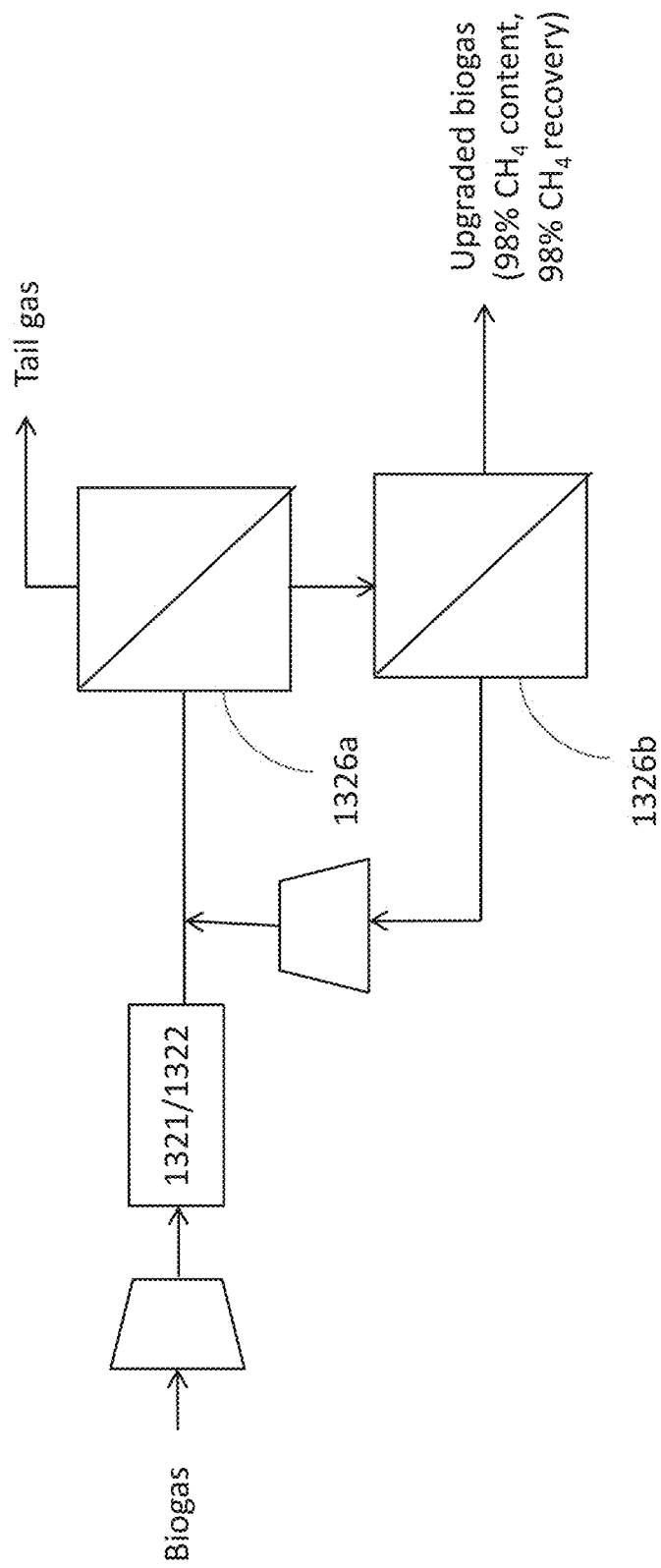
FIG. 13b is a schematic diagram showing an embodiment wherein biogas is upgraded using a 2-stage membrane system; and, FIG. 13c is a schematic diagram showing an embodiment in accordance with one embodiment of the invention wherein biogas is upgraded using a single stage membrane system with a natural gas sweep.

In order to improve methane recovery, a 2-stage membrane system, as illustrated in FIG. 13b, may be used. In this embodiment, biogas is compressed (e.g., to about 200 psi), is subject to a $H_2S$ 1321 and/or $H_2O$ 1322 removal process, and is fed to a first membrane 1326a. The first membrane 1326a removes $CO_2$ from the biogas to produce a $CH_4$-rich stream and a $CH_4$-depleted stream (e.g., tail gas). The $CH_4$-rich stream, which in this embodiment includes some $CO_2$, is fed to a second membrane 1326b, which further reduces the amount of $CO_2$, to provide the upgraded biogas. The permeate from the second membrane 1326b is recycled back to the first membrane 1326a. In general, this type of 2-stage membrane system can meet typical methane purity (e.g., greater than 98%) and methane recovery (e.g., greater than 98%) requirements. For example, in this embodiment, the membrane system has been calculated to provide upgraded biogas having a methane content of about 98%, with a methane recovery of about 98%. About 2% of the methane remains in the tail gas. Although this configuration can achieve a higher methane recovery, it requires an additional compressor, and associated cooler system (now shown), for compressing the recycle stream.

Figure 13C:
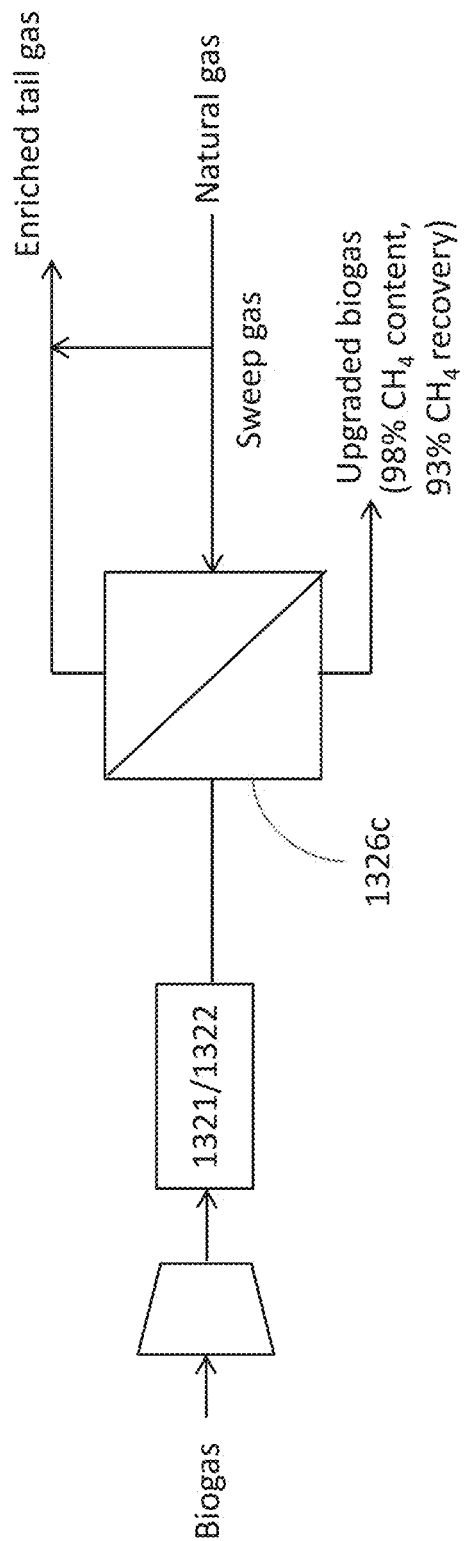

Alternatively, in order to improve methane recovery, a single stage membrane system with a natural gas sweep, as illustrated in FIG. 13c, may be used. In this embodiment, biogas is compressed (e.g., to about 200 psi), is subject to a $H_2S$ 1321 and/or $H_2O$ 1322 removal process, and is fed to a membrane system 1326c. The membrane system 1326c removes $CO_2$ from the biogas to produce a $CH_4$-rich stream (e.g., upgraded biogas) and a $CH_4$-depleted stream.

When a sweep gas is introduced into the membrane system 1326c on the permeate side, it can improve the effectiveness of the membrane by making a larger partial pressure difference over the membrane. In one embodiment, the sweep gas is provided on the permeate side of the membrane in a counterflow configuration. In one embodiment, the sweep gas is provided co-current configuration.

As discussed above, providing a sweep gas can improve the effectiveness of the membrane. In particular, using a natural gas sweep gas may reduce the required membrane area and/or may reduce methane slip. For example, the configuration illustrated in FIG. 13c has been modeled to provide a methane purity of about 98%, with a methane recovery of about 93%. About 7% of the renewable methane remains in the tail gas with less than half of the total membrane area. Accordingly, the configuration illustrated in FIG. 13c can achieve a higher methane recovery than the configuration illustrated in FIG. 13a, without the additional compressor and cooler system required for the configuration illustrated in FIG. 13b and can do so with less than half the membrane area. Since compressors can be associated with relatively high capital and/or operating costs, this is a significant advantage. The required membrane area for the configuration illustrated in FIG. 13c has been modeled to be reduced by 60%, relative to the membrane area required for the configuration illustrated in FIG. 13b. Since the membrane systems discussed above may include a plurality of membrane modules, this reduction in membrane area may advantageously result in fewer membrane modules being used, and thus a much lower system capital cost.

Referring again to FIG. 13c, the sweep gas in this embodiment contains natural gas. Since the sweep gas provides at least some of the natural gas for enriching the tail gas, the tail gas heat content is high enough so that it may be used for producing heat and/or electricity, and does not need to be treated to remove residual methane (e.g., flared). In one embodiment, all of the natural gas used to enrich the tail gas is provided via the sweep gas. In another embodiment, the sweep gas provides only some of the gas used to enrich the tail gas (e.g., 50%), while an additional amount of natural gas is added further downstream.

Of course, the above embodiments have been provided as examples only. It will be appreciated by those of ordinary skill in the art that various modifications, alternate configurations, and/or equivalents will be employed without departing from the spirit and scope of the invention. Accordingly, the scope of the invention is therefore intended to be limited solely by the scope of the appended claims.

What is claimed is:

1. A method of providing upgraded biogas comprising:
feeding biogas into a biogas upgrading system, said biogas upgrading system comprising a membrane having a feed side and a permeate side;
passing biogas across the feed side of the membrane;
passing natural gas across the permeate side of the membrane as a sweep stream such that permeate comprising carbon dioxide is conveyed with natural gas to an outlet of the biogas upgrading system as an enriched tail gas;
feeding upgraded biogas provided by the biogas upgrading system into a distribution system; and
withdrawing natural gas from the distribution system to enrich the tail gas,
wherein passing natural gas across the permeate side of the membrane as a sweep stream comprises passing at least a portion of the natural gas withdrawn from the distribution system across the permeate side of the membrane.

2. The method according to claim 1, wherein withdrawing natural gas from the distribution system comprises withdrawing an amount of natural gas sufficient to provide the enriched tail gas with a methane content that is at least 70% of the methane content of the biogas fed to the biogas upgrading system.

3. The method according to claim 2, further comprising feeding the enriched tail gas to a combustion system, said combustion system configured to produce at least one of heat and electricity.

4. The method according to claim 1, wherein withdrawing natural gas from the distribution system comprises withdrawing an amount of natural gas selected such that for every unit of biogas fed to the biogas upgrading system at least 0.5 unit of natural gas is withdrawn from the distribution system.

5. The method according to claim 1, wherein withdrawing natural gas from the distribution system comprises withdrawing an amount of natural gas sufficient to provide the enriched tail gas with a methane content of at least 30%.

6. The method according to claim 1, wherein a rate of energy delivered of natural gas withdrawn from the distribution system for enriching the tail gas is equal to at least half of a rate of energy delivered of upgraded biogas fed to the distribution system.

7. The method according to claim 1, wherein passing natural gas across the permeate side of the membrane comprises providing the natural gas in a counterflow configuration with the biogas passed across the feed side of the membrane.

8. The method according to claim 1, wherein passing natural gas across the permeate side of the membrane comprises providing the natural gas in a co-current configuration with the biogas passed across the feed side of the membrane.

9. The method according to claim 1, further comprising feeding the enriched tail gas to a combustion system.

10. The method according to claim 1, wherein the biogas upgrading system comprises:
a separating unit for removing carbon dioxide from biogas to provide upgraded biogas and tail gas, said separating unit including a first inlet configured to receive the biogas, a second inlet configured to receive natural gas; a first outlet configured to provide the upgraded biogas, and a second outlet configured to provide the tail gas, said separating unit comprising the membrane having a feed side and a permeate side,
wherein passing biogas across the feed side of the membrane comprises passing biogas received at the first inlet across said feed side of the membrane such that upgraded biogas is provided at the first outlet, and
wherein passing natural gas across the permeate side of the membrane as a sweep stream comprises passing natural gas received at the second inlet across the permeate side of the membrane such that the permeate comprising carbon dioxide is conveyed with the natural gas to the second outlet.

11. The method according to claim 10, comprising adding at least a portion of the withdrawn natural gas to a gas provided by the second outlet.

12. The method according to claim 10, wherein the separating unit comprises a single-stage membrane system.

13. The method according to claim 1, wherein feeding biogas into the biogas upgrading system comprises feeding biogas having a methane content greater than 35% into the biogas upgrading system, wherein feeding upgraded biogas provided by the biogas upgrading system into the distribution system comprises feeding upgraded biogas having a methane content greater than 95% into the distribution system, wherein withdrawing natural gas from the distribution system to enrich the tail gas comprises withdrawing natural gas having a methane content greater than 95%, and wherein the enriched tail gas has a methane content greater than 30%.

14. A process for providing upgraded biogas comprising:
i) obtaining biogas;
ii) feeding the biogas into a biogas upgrading system, said biogas upgrading system comprising a separating unit, said separating unit comprising a membrane having a feed side and a permeate side and having a first inlet configured to receive the biogas, a second inlet configured to receive natural gas; a first outlet configured to provide upgraded biogas, and a second outlet configured to provide tail gas;
iii) passing biogas received at the first inlet across the feed side of the membrane such that some of the carbon dioxide in the biogas permeates through the membrane to the permeate side and such that some methane in the biogas is retained on the feed side and passes to the first outlet;
iv) injecting methane from the biogas provided by the first outlet into a distribution system;
v) withdrawing natural gas from the distribution system;
vi) passing at least a portion of the withdrawn natural gas across the permeate side of the membrane such that the natural gas is conveyed with carbon dioxide permeate to the second outlet; and,
vii) feeding carbon dioxide and natural gas provided by the second outlet to a combustion system.

15. The process according to claim 14, wherein the biogas upgrading system comprises a single-stage membrane system.

16. The process according to claim 14, further comprising producing heat, power, or a combination thereof, using the combustion system.

17. The process according to claim 9, further comprising producing heat, power, or a combination thereof, using the combustion system.

18. The process according to claim 9, comprising removing water, hydrogen sulfide, or a combination thereof from the biogas prior to passing the biogas across the feed side of the membrane.

19. The process according to claim 14, comprising removing water, hydrogen sulfide, or a combination thereof from the biogas prior to passing the biogas across the feed side of the membrane.

20. The process according to claim 9, wherein the enriched tail gas has a heating value of at least 350 BTU/cubic foot.

* * * * *

UNITED STATES PATENT AND TRADEMARK OFFICE
CERTIFICATE OF CORRECTION

PATENT NO. : 10,487,282 B2
APPLICATION NO. : 15/970591
DATED : November 26, 2019
INVENTOR(S) : Brian E. Foody et al.

Page 1 of 2

It is certified that error appears in the above-identified patent and that said Letters Patent is hereby corrected as shown below:

On the Title Page

Column 2, Item (56), Line 2, under Other Publications, delete "biogaz" and insert --biogas--.

On Page 2, Column 2, Item (56), Line 3, under Other Publications, delete "Biogaz" and insert --Biogas--.

On Page 2, Column 2, Item (56), Line 18, under Other Publications, delete "CO2" and insert --$CO_2$--.

In the Specification

In Column 3, Line 10, delete "DSs" and insert --DS--.

In Column 13, Line 58, after "and/or" insert --(iii)--.

In Column 13, Line 65, after "and/or" insert --(ii)--.

In Column 20, Line 38, delete "$CO_2$ rich" and insert --$CO_2$-rich--.

In Column 24, Line 49, delete "$CH_4$ rich" and insert --$CH_4$-rich--.

In Column 24, Line 51, delete "$CH_4$ rich" and insert --$CH_4$-rich--.

In Column 24, Line 52, delete "$CH_4$ rich" and insert --$CH_4$-rich--.

In Column 32, Line 11, delete "Cryo Pur" and insert --Cryo Pur™--.

In Column 33, Line 20, after "levels" insert --of--.

In Column 33, Line 21, delete "burner" and insert --burner),--.

Signed and Sealed this
Twenty-fourth Day of March, 2020

Andrei Iancu
*Director of the United States Patent and Trademark Office*

CERTIFICATE OF CORRECTION (continued)
U.S. Pat. No. 10,487,282 B2

In Column 33, Line 27, delete "(e" and insert --(i.e.,--.

In Column 33, Line 43, after "present" insert --(i.e.,--.

In Column 33, Line 46, delete "BTU/a),"  and insert --BTU/cf),--.

In Column 34, Line 41, delete "(CNG)" and insert --(CNG))--.

In Column 36, Line 22, delete "beneficial used" and insert --beneficial use--.

In Column 43, Lines 18-19, delete "incinerator)." and insert --incinerator.--.

In Column 43, Line 60, delete "(Catepillar™)" and insert --(Caterpillar™)--.

In Column 44, Line 39, delete "(-450° C.)" and insert --(~450° C.)--.

In Column 46, Line 33, delete "((energy" and insert --(energy--.

In Column 49, Line 16, delete "(e.g.," and insert --e.g.,--.

In Column 54, Line 33, delete "(EEEEEEEE)" and insert --(EEEEEEEE).--.

In Column 59, Line 35, delete "RGN" and insert --RNG--.

In Column 67, Line 41, delete "(now" and insert --(not--.

In the Claims

In Column 70, Line 38, Claim 17, delete "process" and insert --method--.

In Column 70, Line 41, Claim 18, delete "process" and insert --method--.

In Column 70, Line 49, Claim 20, delete "process" and insert --method--.